US008637043B2

(12) United States Patent
Schall et al.

(10) Patent No.: US 8,637,043 B2
(45) Date of Patent: Jan. 28, 2014

(54) COMPOSITIONS USEFUL AS LIGANDS FOR THE FORMYL PEPTIDE RECEPTOR LIKE 1 RECEPTOR AND METHODS OF USE THEREOF

(75) Inventors: Thomas J. Schall, Palo Alto, CA (US); Zhenhua Miao, San Jose, CA (US); Robert Berahovich, Berkeley, CA (US); Zheng Wei, Union City, CA (US); Maureen Howard, Los Altos, CA (US); Brett Premack, San Francisco, CA (US)

(73) Assignee: Chemocentryx, Inc., Mt. View, CA (US)

( * ) Notice: Subject to any disclaimer, the term of this patent is extended or adjusted under 35 U.S.C. 154(b) by 1779 days.

(21) Appl. No.: 11/175,003

(22) Filed: Jul. 5, 2005

(65) Prior Publication Data

US 2006/0034863 A1     Feb. 16, 2006

Related U.S. Application Data

(63) Continuation of application No. 10/141,508, filed on May 7, 2002, now abandoned, and a continuation of application No. 10/141,620, filed on May 7, 2002.

(60) Provisional application No. 60/328,241, filed on Oct. 9, 2001.

(51) Int. Cl.
*A61K 39/02* (2006.01)

(52) U.S. Cl.
USPC ....................................................... 424/190.1

(58) Field of Classification Search
None
See application file for complete search history.

(56) References Cited

U.S. PATENT DOCUMENTS

| 4,522,811 | A |   | 6/1985  | Eppstein et al. |
|-----------|---|---|---------|-----------------|
| 4,877,611 | A | * | 10/1989 | Cantrell ...................... 424/277.1 |
| 5,223,409 | A |   | 6/1993  | Ladner et al. |
| 5,284,753 | A |   | 2/1994  | Goodwin, Jr. |
| 5,328,470 | A |   | 7/1994  | Nabel et al. |
| 5,772,981 | A |   | 6/1998  | Govindan et al. |
| 5,874,211 | A |   | 2/1999  | Bandman et al. |
| 5,942,252 | A |   | 8/1999  | Tice et al. |
| 5,994,126 | A |   | 11/1999 | Steinman et al. |
| 6,001,606 | A |   | 12/1999 | Ruben et al. |
| 6,881,408 | B1| * | 4/2005  | Heinrich et al. ........... 424/140.1 |

FOREIGN PATENT DOCUMENTS

| JP | 2001-500382 A   | 1/2001  |
| WO | WO 96/32481 A1  | 10/1996 |
| WO | WO 98/14582     | 4/1998  |
| WO | WO 01/26676     | 4/2001  |

OTHER PUBLICATIONS

Harlow et al. Antibodies, A Laboratory Manual. Cold Spring Harbor Laboratory Press. Cold Spring Harbor, New York, 1998, p. 76.*
Bacon, K.B. et al., Contrasting in vitro lymphocyte chemotactic activity of the hydroxyl enantiomers of 12-hydroxy-5,8,10,14-eicosatetraenoic acid, Br. J. Pharmacol., 1988, vol. 95, pp. 966-74.
Bender, A.M. et al., Improved methods for the generation of dendritic cells from nonproliferating progenitors in human blood, J. Immunol. Methods, 1996, vol. 196, pp. 121-135.
Chen, S.H. et al., Gene therapy for brain tumors: regression of experimental gliomas by adenovirus-mediated gene transfer in vivo, Proc. Natl. Acad. Sci. USA, 1994, vol. 91, pp. 3054-3057.
Kaufman, R.J., Vectors used for expression in mammalian cells, Methods Enzymol., 1990, vol. 185, pp. 487-511.
Kraal, G. et al., Langerhans' cells, veiled cells, and interdigitating cells in the mouse recognized by a monoclonal antibody, J. Exp. Med., 1986, vol. 163, pp. 981-997.
Penfold, M.E. et al., Cytomegalovirus encodes a potent alpha chemokine, Proc. Natl. Acad. Sci. USA, 1999, vol. 96, pp. 9839-9844.
Elagoz, Aram, et al. "A Truncated Form of CKbeta8-1 Is a Potent Agonist for Human Formyl Peptide-Receptor-Like 1 Receptor" British Journal of Pharmacology, vol. 141, No. 1, pp. 37-46, Jan. 2004.
"hmrp-2a mRNA, complete cds" Database EMBL, Jul. 1999.
Baek, S.H. et al., "Identification of the peptides that stimulate the phosphoinositide hydrolysis in lymphocyte cell lines from peptide libraries," J. Biol. Chem., 1996, vol. 271, pp. 8170-8175.
Baggiolini, M. et al., "CC chemokines in allergic inflammation," Immunol. Today, 1994, vol. 15, p. 127-133.
Berkhout, T.A. et al., "Selective binding of the truncated form of the chemokine CKbeta8 (25-99) to CC chemokine receptor 1(CCR1)," Biochem.Pharmacol., 2000, vol. 59, p. 591-596.
Bonecchi, R. et al., "Up-regulation of CCR1 and CCR3 and induction of chemotaxis to CC chemokines by IFN-gamma in human neutrophils," J.Immunol, 1999, vol. 162, p. 474-479.
Bao L. et al., "Mapping of genes for the human C5a receptor (C5AR), human FMLP receptor (FPR), and two FMLP receptor homologue orphan receptors (FPRH1, FPRH2) to chromosome 19," Genomics, 1992, vol. 13, pp. 437-440.
Campbell et al. "6-C-kine (SLC), a lymphocyte adhesion-triggering chemokine expressed by high endothelium, is an agonist for the MIP-3beta receptor CCR7", J. Cell Biol., 1998, vol. 141, pp. 1053-1059.

(Continued)

Primary Examiner — Gregory S Emch
(74) Attorney, Agent, or Firm — Brinks Gilson & Lione

(57) ABSTRACT

The inventors have discovered that a CKβ8-1 truncation variant, CKβ8-1 (25-116), is a bifunctional ligand for two distinct GPCRs, chemokine receptor CCR1 and formyl peptide receptor like 1 (FPRL1). Hence, the inventors have discovered that, in addition to its functional activity on CCR1, CKβ8-1(25-116) is also a functional ligand for the GPCR receptor FPRL1 that is involved in inflammatory reactions and innate immunity by recruiting monocytes and neutrophils. In addition, the inventors have discovered an alternatively spliced exon of CKβ8-1, named SHAAGtide. SHAAGtide, along with its parent chemokine CKβ8-1 (25-116), is fully functional on both monocytes and neutrophils that are known to express FPRL1.
This application relates generally to enhancing immune responses. Such immune responses may be elicited by vaccine administration. Compositions and methods for inducing or enhancing an immune response to an antigen are provided. The compositions and methods are useful for vaccine formulations for therapeutic and prophylactic use (immunization) and for production of antibodies.

11 Claims, 2 Drawing Sheets

(56) References Cited

OTHER PUBLICATIONS

Cella, M. et al. "Maturation, activation, and protection of dendritic cells induced by double-stranded RNA", *J. Exp. Med.*, 1999, vol. 189, pp. 821-829.

Chan et al., "Secondary lymphoid-tissue chemokine (SLC) is chemotactic for mature dendritic cells", Blood, 1999, vol. 93, pp. 3610-3616.

Christophe, T. et al., "The synthetic peptide Trp-Lys-Tyr-Met-Val-Met-$NH_2$ specifically activates neutrophils through FPRL1/Lipoxin $A_4$ Receptors and is an agonist for the orphan monocyte-expressed chemoattractant receptor FPRL2," *J. Biol. Chem.*, 2001, vol. 276, pp. 21585-21593.

Deng, X. et al., "A synthetic peptide derived from human immunodeficiency virus type 1 gp120 downregulates the expression and function of chemokine receptors CCR5 and CXCR4 in monocytes by activating the 7-transmembrane G-protein-coupled receptor FPRL1/LXA4R" *Blood*, 1999, vol. 94, pp. 1165-1173.

Devlin, J.J. et al., "Random peptide libraries: a source of specific protein binding molecules," *Science*, 1990, vol. 294, pp. 404-406.

Dieu, M. et al., "Selective recruitment of immature and mature dendritic cells by distinct chemokines expressed in different anatomic sites", *J.Exp.Med.*, 1998 vol. 188, p. 373-386.

Fantuzzi, L. et al., "Loss of CCR2 expression and functional response to monocyte chemotactic protein (MCP-1) during the differentiation of human monocytes: role of secreted MCP-1 in the regulation of the chemotactic response," *Blood*, 1999, vol. 94 p. 875-883.

Forssmann, U. et al., "CKbeta8, a novel CC chemokine that predominantly acts on monocytes", *FEBS Lett.*, 1997, vol. 408, p. 211-216.

Kellerman, S-A. et al., "The CC chemokine receptor-7 ligands 6Ckine and macrophage inflammatory protein-3beta are potent chemoattractants for in vitro- and in vivo-derived dendritic cells", *J. Immunol.*, 1999, vol. 162, pp. 3859-3864.

Le, Y. et al., "Survey: Pleiotropic roles of formyl peptide receptors," *Cytokine and Growth Factor Reviews*, 2001, vol. 12, pp. 91-105.

Lee, S.C. et al., "Cutaneous injection of human subjects with macrophage inflammatory protein-1 alpha induces significant recruitment of neutrophils and monocytes," *J. Immunol.*, 2000, vol. 164, p. 3392-3401.

Macphee, C.H. et al., "Identification of a truncated form of the CC chemokine CK beta-8 demonstrating greatly enhanced biological activity," *J. Immunol.*, 1998, vol. 161, p. 6273-6279.

Mantovani, A., "The chemokine system: redundancy for robust outputs," *Immunol Today*, 1999, vol. 20, pp. 254-257.

Murphy, P.M. et al., "A structural homologue of the N-formyl peptide receptor. Characterization and chromosome mapping of a peptide chemoattractant receptor family," *J. Biol. Chem.*, 1992, vol. 267, pp. 7637-7643.

Patel, V.P. et al., "Molecular and functional characterization of two novel human C-C chemokines as inhibitors of two distinct classes of myeloid progenitors", *J.Exp.Med.*, 1997, vol. 185, p. 1163-1172.

Rollins, B.J., "Chemokines", *Blood*, 1997, vol. 90, pp. 909-928.

Romani, N. et al., "Generation of mature dendritic cells from human blood. An improved method with special regard to clinical applicability", *J. Immunol. Methods*, 1996, vol. 196, pp. 137-151.

Su, S.B. et al., "T21/DP107, a synthetic leucine zipper-like domain of the HIV-1 Envelope gp41, attracts and activates human phagocytes by using G-protein-coupled formyl peptide receptors", *J. Immunol.*, 1999, vol. 162, pp. 5924-5930.

Uguccioni, M. et al., "Actions on the cemotactic cytokines MCP-1, MCP-2, MCP-3, RANTES, MIP-1 alpha and MIP-1 beta on human-monocytes", *Eur.J. Immunol.*, 1995, vol. 25, pp. 64-68.

Verdijk, R. et al., "Polyriboinosinic polyribocytidylic acid (Poly(I:C)) induces stable maturation of functionally active human dendritic cells", *J.Immunol.*, 1999, vol. 1, pp. 57-61.

Weber, C., et al., "Differential chemokine receptor expression and function in human monocyte subpopulations," J. Leukoc. Biol., 2000 vol. 67, pp. 699-704.

Ye, R.D. et al., "Isolation of a cDNA that encodes a novel granulocyte N-formyl peptide receptor," *Biochem.Biophys.Res.Commun.*;,1992, vol. 184, pp. 582-589.

Youn, B.S. et al., "Characterization of CKbeta8 and CKbeta8-1: two alternatively spliced forms of human beta-chemokine, chemoattractants for neutrophils, monocytes, and lymphocytes, and potent agonists at CC chemokine receptor 1", Blood, 1998, vol. 91, p. 3118-3126.

Zuckermann, R.N. et al., "Discovery of nanomolar ligands for 7-transmembrane G-protein-coupled receptors from a diverse N-(Substituted)glycine peptoid library," *J. Med Chem.*, 1994, vol. 37, pp. 2678-2685.

"Human MPIF-1 Splice Variant Protein Deletion Mutant No:2", Database EMBL, Oct. 1998.

"Human MIF-1 Splice Variant Protein Deletion Mutant #1", Database EMBL, Oct. 1998.

Bae, Y-S. et al., "Identification of novel chemoattractant peptide for human leukocytes," *Blood*, May 1, 2001 97(9):2854-2862.

Murphy, "The N-formylpeotide chemotactic receptors, Chemoattractant ligands and their receptors," *CRC Press*, Boca Raton, p. 269 (1996).

Prieschl EE et al. "The nomenclature of chemokines" *Int Arch Allergy Immunol* (1995) 107:475-483.

Rossi, D., et al. "The Biology of Chemokines and their Receptors" *Annu. Rev. Immunol.* (2000) 18:217-242.

Voet et al., "Biochemistry," John Wiley & Sons, Inc. 126-128 and 228-234 (1990).

Mickle, Je et al. "Genotype—phenotype relationships in cystic fibrosis," Med. Clin. North Am., 84(3):597-607 (May 2000).

Yan et al., "Two-amino acid molecular switch in an epithelial morphogen that regulates binding to two distinct receptors," Science, 290:523-527 (2000).

Youn et al., "Isolation and Characterization of LMC, a Novel Lymphocyte and Monocyte Chemoattractant Human CC Chemokine, with Myelosuppressive Activity," Biochemical and Biophysical Research Communications, 247:217-222 (1998).

* cited by examiner

Figure 1    Reported FPRL1 ligands

| Ligands | Calcium Flux (EC50) | Migration (EC50) | Binding (EC50) |
|---|---|---|---|
| *Endogenous Ligands:* | | | |
| Lipoxin A4 | ? | ? | 2-10 nM to H$^3$-LPX |
| Serum amyloid A | >0.2 uM | >0.2uM | 250 nM to I$^{125}$-SSA |
| β-Amyloid (1-42) | >2uM | 10 uM | |
| Prion Peptide PrP(106-126) | >2 uM | 25-50 uM | |
| LL-37[1] | >5 uM | 5-10 uM | |
| D2D3(88-274)[2] | ? | 0.1 nM (on 293-FPRL1)[3] | 83 nM to I$^{125}$-D2D3(88-274) |
| *Viral & Bacterial Encoded:* | | | |
| T21/DP107 (HIV gp41) | >0.5 uM | >0.5 uM | |
| HIV gp120(414-434) | 5-10 uM | 5-10 uM | |
| H. pylori peptide, Hp(2-20)[4] | 10 uM | | |
| fMLP | >5 uM | | |
| *Non-natural Ligands:* | | | |
| WKYMVm | 0.1-1 nM | 0.1-1 nM | 10 nM to I$^{125}$-W Peptide |
| WKYMVM | 1-10 nM | 1-10 nM | >10 nM to I$^{125}$-W Peptide |
| MMK-1 | low nM | low nM | |

*Notes:*

1. Human cathelicidin-derived antibacterial peptide, LL-37.
2. Urokinase plasminogen activator (uPA), D2D3(88-274).
3. In neutrophils, neither uPA nor D2D3(88-274) induce calcium flux.
4. Helicobacter pylori peptide, Hp(2-20).

```
                         1                   11                    21                    31                   41                    51
CKβ8 (1-99)                  RVTKDAETEFMMSKLPLENPVLLD- - - - - - - - - - - - - - - - -RFHATSADCCISYTPRSIP
CKβ8 (25-99)                               RVTKDAETEFMMSKLPLENPVLLDMLWRRKIGPQMTLSHAAGFHATSADCCISYTPRSIP
CKβ8-1 (1-116)                             RVTKDAETEFMMSKLPLENPVLLDMLWRRKIGPQMTLSHAAGFHATSADCCISYTPRSIP
CKβ8-1 (25-116)                                             MLWRRKIGPQMTLSHAAGFHATSADCCISYTPRSIP
MIP1δ          QFINDAETELMMSKLPLENPVVLN- - - - - - - - - - - - - - - - - - -SFHF - AADCCTSYISQSIP
Leukotactin                                                        SFHF - AADCCTSYISQSIP
MIP1α                                                        SLAADTPTACCFSYTSRQIP 61                  71                    81                    91                                #
CKβ8 (1-99)     CSLLESYFETNSECSKPGVIFLTKKGRRFCANPSDKQVQVCMRMLKLDTRIKTRKN            SEQ ID NO:13
CKβ8 (25-99)    CSLLESYFETNSECSKPGVIFLTKKGRRFCANPSDKQVQVCMRMLKLDTRIKTRKN            SEQ ID NO:14
CKβ8-1 (1-116)  CSLLESYFETNSECSKPGVIFLTKKGRRFCANPSDKQVQVCMRMLKLDTRIKTRKN            SEQ ID NO:15
CKβ8-1 (25-116) CSLLESYFETNSECSKPGVIFLTKKGRRFCANPSDKQVQVCMRMLKLDTRIKTRKN            SEQ ID NO:16
MIP1δ           CSLMKSYFETSSECSKPGVIFLTKKGRQVCAKPSGPGVQDCMKKLKPYSI                  MIP-1δ      SEQ ID NO:17
Leukotactin     CSLMKSYFETSSECSKPGVIFLTKKGRQVCAKPSGPGVQDCMKKLKPYSI                  Leukotactin SEQ ID NO:18
MIP1α           QNFIADYFETSSQCSKPGVIFLTKRSRQVCADPSEEWVQKYVSDLE                      MIP-1α      SEQ ID NO:19
```

Figure 2.

SEQUENCE LISTING

<160> NUMBER OF SEQ ID NOS: 33

<210> SEQ ID NO 1
<211> LENGTH: 18
<212> TYPE: PRT
<213> ORGANISM: Artificial Sequence
<220> FEATURE:
<223> OTHER INFORMATION: SHAAGtide

<400> SEQUENCE: 1

Met Leu Trp Arg Arg Lys Ile Gly Pro Gln Met Thr Leu Ser His Ala
1               5                   10                  15

Ala Gly

<210> SEQ ID NO 2
<211> LENGTH: 15

```
<212> TYPE: PRT
<213> ORGANISM: Artificial Sequence
<220> FEATURE:
<223> OTHER INFORMATION: SHAAGtide variant

<400> SEQUENCE: 2

Arg Arg Lys Ile Gly Pro Gln Met Thr Leu Ser His Ala Ala Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: SHAAGtide variant

<400> SEQUENCE: 3

Met Leu Trp Arg Arg Lys Ile Gly Pro Gln Met Thr Leu Ser His
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: SHAAGtide variant

<400> SEQUENCE: 4

Ile Gly Pro Gln Met Thr Leu Ser His Ala Ala Gly
1               5                   10

<210> SEQ ID NO 5
<211> LENGTH: 12
<212> TYPE: PRT
<213> ORGANISM: Artificial Sequence
<220> FEATURE:
<223> OTHER INFORMATION: SHAAGtide variant

<400> SEQUENCE: 5

Met Leu Trp Arg Arg Lys Ile Gly Pro Gln Met Thr
1               5                   10

<210> SEQ ID NO 6
<211> LENGTH: 18
<212> TYPE: PRT
<213> ORGANISM: Artificial Sequence
<220> FEATURE:
<223> OTHER INFORMATION: SHAAGtide variant

<400> SEQUENCE: 6

Met Leu Trp Arg Arg Lys Ile Gly Pro Gln Met Thr Leu Ser His Ala
1               5                   10                  15

Ala Tyr

<210> SEQ ID NO 7
<211> LENGTH: 16
<212> TYPE: PRT
<213> ORGANISM: Artificial Sequence
<220> FEATURE:
<223> OTHER INFORMATION: SHAAGtide variant

<400> SEQUENCE: 7

Trp Arg Arg Lys Ile Gly Pro Gln Met Thr Leu Ser His Ala Ala Gly
1               5                   10                  15

<210> SEQ ID NO 8
<211> LENGTH: 11
```

```
<212> TYPE: PRT
<213> ORGANISM: Artificial Sequence
<220> FEATURE:
<223> OTHER INFORMATION: SHAAGtide variant

<400> SEQUENCE: 8

Met Leu Trp Arg Arg Lys Ile Gly Pro Gln Met
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: SHAAGtide variant

<400> SEQUENCE: 9

Trp Arg Arg Lys Ile Gly Pro Gln Met
 1               5

<210> SEQ ID NO 10
<211> LENGTH: 6
<212> TYPE: PRT
<213> ORGANISM: Artificial Sequence
<220> FEATURE:
<223> OTHER INFORMATION: SHAAGtide variant

<400> SEQUENCE: 10

Trp Arg Arg Lys Ile Gly
 1               5

<210> SEQ ID NO 11
<211> LENGTH: 14
<212> TYPE: PRT
<213> ORGANISM: Artificial Sequence
<220> FEATURE:
<223> OTHER INFORMATION: SHAAGtide variant

<400> SEQUENCE: 11

Leu Trp Arg Arg Lys Ile Gly Pro Gln Met Thr Leu Ser His
 1               5                  10

<210> SEQ ID NO 12
<211> LENGTH: 279
<212> TYPE: DNA
<213> ORGANISM: Homo sapiens

<400> SEQUENCE: 12
atgctctgga ggagaaagat tggtcctcag atgacccttt ctcatgctgc aggattccat      60
gctactagtg ctgactgctg catctcctac accccacgaa gcatcccgtg ttcactcctg     120
gagagttact ttgaaacgaa cagcgagtgc tccaagccgg gtgtcatctt cctcaccaag     180 aagggcgac gtttctgtgc caaccccagt gataagcaag ttcaggtttg catgagaatg      240
ctgaagctgg acacacggat caagaccagg aagaattga                            279

<210> SEQ ID NO 13
<211> LENGTH: 99
<212> TYPE: PRT
<213> ORGANISM: Homo sapiens

<400> SEQUENCE: 13

Arg Val Thr Lys Asp Ala Glu Thr Glu Phe Met Met Ser Lys Leu Pro
 1               5                  10                  15

Leu Glu Asn Pro Val Leu Leu Asp Arg Phe His Ala Thr Ser Ala Asp
                20                  25                  30
```

Cys Cys Ile Ser Tyr Thr Pro Arg Ser Ile Pro Cys Ser Leu Leu Glu
            35                  40                  45

Ser Tyr Phe Glu Thr Asn Ser Glu Cys Ser Lys Pro Gly Val Ile Phe
 50                  55                  60

Leu Thr Lys Lys Gly Arg Arg Phe Cys Ala Asn Pro Ser Asp Lys Gln
 65                  70                  75                  80

Val Gln Val Cys Met Arg Met Leu Lys Leu Asp Thr Arg Ile Lys Thr
            85                  90                  95

Arg Lys Asn

<210> SEQ ID NO 14
<211> LENGTH: 75
<212> TYPE: PRT
<213> ORGANISM: Homo sapiens

<400> SEQUENCE: 14

Arg Phe His Ala Thr Ser Ala Asp Cys Cys Ile Ser Tyr Thr Pro Arg
 1               5                  10                  15

Ser Ile Pro Cys Ser Leu Leu Glu Ser Tyr Phe Glu Thr Asn Ser Glu
            20                  25                  30

Cys Ser Lys Pro Gly Val Ile Phe Leu Thr Lys Lys Gly Arg Arg Phe
            35                  40                  45

Cys Ala Asn Pro Ser Asp Lys Gln Val Gln Val Cys Met Arg Met Leu
 50                  55                  60

Lys Leu Asp Thr Arg Ile Lys Thr Arg Lys Asn
 65                  70                  75

<210> SEQ ID NO 15
<211> LENGTH: 116
<212> TYPE: PRT
<213> ORGANISM: Homo sapiens

<400> SEQUENCE: 15

Arg Val Thr Lys Asp Ala Glu Thr Glu Phe Met Met Ser Lys Leu Pro
 1               5                  10                  15

Leu Glu Asn Pro Val Leu Leu Asp Met Leu Trp Arg Arg Lys Ile Gly
            20                  25                  30

Pro Gln Met Thr Leu Ser His Ala Ala Gly Phe His Ala Thr Ser Ala
            35                  40                  45

Asp Cys Cys Ile Ser Tyr Thr Pro Arg Ser Ile Pro Cys Ser Leu Leu
 50                  55                  60

Glu Ser Tyr Phe Glu Thr Asn Ser Glu Cys Ser Lys Pro Gly Val Ile
 65                  70                  75                  80

Phe Leu Thr Lys Lys Gly Arg Arg Phe Cys Ala Asn Pro Ser Asp Lys
            85                  90                  95

Gln Val Gln Val Cys Met Arg Met Leu Lys Leu Asp Thr Arg Ile Lys
            100                 105                 110

Thr Arg Lys Asn
        115

<210> SEQ ID NO 16
<211> LENGTH: 92
<212> TYPE: PRT
<213> ORGANISM: Homo sapiens

<400> SEQUENCE: 16

Met Leu Trp Arg Arg Lys Ile Gly Pro Gln Met Thr Leu Ser His Ala
 1               5                  10                  15

-continued

Ala Gly Phe His Ala Thr Ser Ala Asp Cys Cys Ile Ser Tyr Thr Pro
            20                  25                  30

Arg Ser Ile Pro Cys Ser Leu Leu Glu Ser Tyr Phe Glu Thr Asn Ser
        35                  40                  45

Glu Cys Ser Lys Pro Gly Val Ile Phe Leu Thr Lys Lys Gly Arg Arg
 50                  55                  60

Phe Cys Ala Asn Pro Ser Asp Lys Gln Val Gln Val Cys Met Arg Met
65                  70                  75                  80

Leu Lys Leu Asp Thr Arg Ile Lys Thr Arg Lys Asn
                85                  90

<210> SEQ ID NO 17
<211> LENGTH: 92
<212> TYPE: PRT
<213> ORGANISM: Homo sapiens

<400> SEQUENCE: 17

Gln Phe Ile Asn Asp Ala Glu Thr Glu Leu Met Met Ser Lys Leu Pro
1               5                   10                  15

Leu Glu Asn Pro Val Val Leu Asn Ser Phe His Phe Ala Ala Asp Cys
            20                  25                  30

Cys Thr Ser Tyr Ile Ser Gln Ser Ile Pro Cys Ser Leu Met Lys Ser
        35                  40                  45

Tyr Phe Glu Thr Ser Ser Glu Cys Ser Lys Pro Gly Val Ile Phe Leu
 50                  55                  60

Thr Lys Lys Gly Arg Gln Val Cys Ala Lys Pro Ser Gly Pro Gly Val
65                  70                  75                  80

Gln Asp Cys Met Lys Lys Leu Lys Pro Tyr Ser Ile
                85                  90

<210> SEQ ID NO 18
<211> LENGTH: 68
<212> TYPE: PRT
<213> ORGANISM: Homo sapiens

<400> SEQUENCE: 18

Ser Phe His Phe Ala Ala Asp Cys Cys Thr Ser Tyr Ile Ser Gln Ser
1               5                   10                  15

Ile Pro Cys Ser Leu Met Lys Ser Tyr Phe Glu Thr Ser Ser Glu Cys
            20                  25                  30

Ser Lys Pro Gly Val Ile Phe Leu Thr Lys Lys Gly Arg Gln Val Cys
        35                  40                  45

Ala Lys Pro Ser Gly Pro Gly Val Gln Asp Cys Met Lys Lys Leu Lys
 50                  55                  60

Pro Tyr Ser Ile
65

<210> SEQ ID NO 19
<211> LENGTH: 66
<212> TYPE: PRT
<213> ORGANISM: Homo sapiens

<400> SEQUENCE: 19

Ser Leu Ala Ala Asp Thr Pro Thr Ala Cys Cys Phe Ser Tyr Thr Ser
1               5                   10                  15

Arg Gln Ile Pro Gln Asn Phe Ile Ala Asp Tyr Phe Glu Thr Ser Ser
            20                  25                  30

Gln Cys Ser Lys Pro Gly Val Ile Phe Leu Thr Lys Arg Ser Arg Gln

Val Cys Ala Asp Pro Ser Glu Glu Trp Val Gln Lys Tyr Val Ser Asp
 50                  55                  60

Leu Glu
65

<210> SEQ ID NO 20
<211> LENGTH: 54
<212> TYPE: DNA
<213> ORGANISM: Artificial Sequence
<220> FEATURE:
<223> OTHER INFORMATION: SHAAGtide polynucleotide variant

<400> SEQUENCE: 20
atgctctgga ggagaaagat tggtcctcag atgacccttt ctcatgctgc agga        54

<210> SEQ ID NO 21
<211> LENGTH: 45
<212> TYPE: DNA
<213> ORGANISM: Artificial Sequence
<220> FEATURE:
<223> OTHER INFORMATION: SHAAGtide polynucleotide variant

<400> SEQUENCE: 21
aggagaaaga ttggtcctca gatgacccct ttctcatgctg cagga               45

<210> SEQ ID NO 22
<211> LENGTH: 45
<212> TYPE: DNA
<213> ORGANISM: Artificial Sequence
<220> FEATURE:
<223> OTHER INFORMATION: SHAAGtide polynucleotide variant

<400> SEQUENCE: 22
atgctctgga ggagaaagat tggtcctcag atgacccttt ctcat                45

<210> SEQ ID NO 23
<211> LENGTH: 36
<212> TYPE: DNA
<213> ORGANISM: Artificial Sequence
<220> FEATURE:
<223> OTHER INFORMATION: SHAAGtide polynucleotide variant

<400> SEQUENCE: 23
attggtcctc agatgaccct ttctcatgct gcagga                          36

<210> SEQ ID NO 24
<211> LENGTH: 36
<212> TYPE: DNA
<213> ORGANISM: Artificial Sequence
<220> FEATURE:
<223> OTHER INFORMATION: SHAAGtide polynucleotide variant

<400> SEQUENCE: 24
atgctctgga ggagaaagat tggtcctcag atgacc                          36

<210> SEQ ID NO 25
<211> LENGTH: 54
<212> TYPE: DNA
<213> ORGANISM: Artificial Sequence
<220> FEATURE:
<223> OTHER INFORMATION: SHAAGtide polynucleotide variant

<400> SEQUENCE: 25
atgctctgga ggagaaagat tggtcctcag atgacccttt ctcatgctgc atat        54

-continued

```
<210> SEQ ID NO 26
<211> LENGTH: 48
<212> TYPE: DNA
<213> ORGANISM: Artificial Sequence
<220> FEATURE:
<223> OTHER INFORMATION: SHAAGtide polynucleotide variant

<400> SEQUENCE: 26
tggaggagaa agattggtcc tcagatgacc ctttctcatg ctgcagga          48

<210> SEQ ID NO 27
<211> LENGTH: 33
<212> TYPE: DNA
<213> ORGANISM: Artificial Sequence
<220> FEATURE:
<223> OTHER INFORMATION: SHAAGtide polynucleotide variant

<400> SEQUENCE: 27
atgctctgga ggagaaagat tggtcctcag atg                         33

<210> SEQ ID NO 28
<211> LENGTH: 27
<212> TYPE: DNA
<213> ORGANISM: Artificial Sequence
<220> FEATURE:
<223> OTHER INFORMATION: SHAAGtide polynucleotide variant

<400> SEQUENCE: 28
tggaggagaa agattggtcc tcagatg                                27

<210> SEQ ID NO 29
<211> LENGTH: 18
<212> TYPE: DNA
<213> ORGANISM: Artificial Sequence
<220> FEATURE:
<223> OTHER INFORMATION: SHAAGtide polynucleotide variant

<400> SEQUENCE: 29
tggaggagaa agattggt                                          18

<210> SEQ ID NO 30
<211> LENGTH: 42
<212> TYPE: DNA
<213> ORGANISM: Artificial Sequence
<220> FEATURE:
<223> OTHER INFORMATION: SHAAGtide polynucleotide variant

<400> SEQUENCE: 30
ctctggagga gaaagattgg tcctcagatg acccttttctc at              42

<210> SEQ ID NO 31
<211> LENGTH: 137
<212> TYPE: PRT
<213> ORGANISM: Homo sapiens

<400> SEQUENCE: 31

Met Lys Val Ser Val Ala Ala Leu Ser Cys Leu Met Leu Val Thr Ala
 1               5                  10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Met Leu Trp
        35                  40                  45

Arg Arg Lys Ile Gly Pro Gln Met Thr Leu Ser His Ala Ala Gly Phe
    50                  55                  60
```

```
His Ala Thr Ser Ala Asp Cys Cys Ile Ser Tyr Thr Pro Arg Ser Ile
 65                  70                  75                  80

Pro Cys Ser Leu Leu Glu Ser Tyr Phe Glu Thr Asn Ser Glu Cys Ser
                 85                  90                  95

Lys Pro Gly Val Ile Phe Leu Thr Lys Lys Gly Arg Arg Phe Cys Ala
            100                 105                 110

Asn Pro Ser Asp Lys Gln Val Gln Val Cys Met Arg Met Leu Lys Leu
            115                 120                 125

Asp Thr Arg Ile Lys Thr Arg Lys Asn
            130                 135

<210> SEQ ID NO 32
<211> LENGTH: 414
<212> TYPE: DNA
<213> ORGANISM: Homo sapiens

<400> SEQUENCE: 32
atgaaggtct ccgtggctgc cctctcctgc ctcatgcttg ttactgccct tggatcccag      60
gcccgggtca caaaagatgc agagacagag ttcatgatgt caaagcttcc attggaaaat    120
ccagtacttc tggacatgct ctggaggaga aagattggtc ctcagatgac cctttctcat    180
gctgcaggat tccatgctac tagtgctgac tgctgcatct cctacacccc acgaagcatc    240
ccgtgttcac tcctggagag ttactttgaa acgaacagcg agtgctccaa gccgggtgtc    300
atcttcctca ccaagaaggg gcgacgtttc tgtgccaacc ccagtgataa gcaagttcag    360
gtttgcatga aatgctgaa gctggacaca cggatcaaga ccaggaagaa ttga           414

<210> SEQ ID NO 33
<211> LENGTH: 18
<212> TYPE: PRT
<213> ORGANISM: Artificial Sequence
<220> FEATURE:
<223> OTHER INFORMATION: Synthetic sequence

<400> SEQUENCE: 33

Gly Ala Ala His Ser Leu Thr Met Gln Pro Gly Ile Lys Arg Arg Trp
 1               5                  10                  15

Leu Met
```

COMPOSITIONS USEFUL AS LIGANDS FOR THE FORMYL PEPTIDE RECEPTOR LIKE 1 RECEPTOR AND METHODS OF USE THEREOF

RELATED APPLICATIONS

This application is a continuation application of U.S. patent application Ser. No. 10/141,508, filed May 7, 2002 now abandoned and a continuation application of U.S. patent application Ser. No. 10/141,620, filed May 7, 2002, which claims priority to U.S. provisional application Ser. No. 60/328,241, filed Oct. 9, 2001, disclosures of which are incorporated by reference in their entirety.

FIELD OF THE INVENTION

The invention relates to compositions useful as ligands for the Formyl Peptide Receptor Like 1 receptor and methods of use thereof.

The invention relates to compositions and methods relating to enhancing or modulating immune responses, such as those elicited by vaccination. The compositions and methods are useful for, among other things, vaccine formulation for therapeutic and prophylactic vaccination (immunization) and for production of useful antibodies (e.g., monoclonal antibodies, for therapeutic or diagnostic use).

BACKGROUND

Chemokines (chemotactic cytokines) act as molecular beacons for the recruitment and activation of T lymphocytes, neutrophils and macrophages, flagging pathogen battlegrounds. Recruitment of leukocytes, the white blood cells responsible for fighting infections depends on gradients of chemokines. Chemokines are a superfamily of small proteins (8-10 KD) that mediate diverse biological processes including leukocyte trafficking and homing, immunoregulation, hematopoiesis and antiogenesis. To date, 24 chemokine receptors are known. Chemokines play a fundamental role in innate immunity and inflammatory reactions (Baggiolini et al. (1994); Baggiolini et al. (1997); Rollins (1997).) Four subfamilies of chemokines have been described, based on the distance between the first two conserved cysteine residues: C, CC, CXC, and CX3C. All known chemokines signal through four groups of seven transmembrane receptors which belong to the G protein-coupled receptor and pertussis toxin-sensitive heterotrimeric G proteins of $G_i$ family: XCR, CCR, CXCR and CX3CR. (Murphy et al. (2000)). Extracellular binding events can activate specific signal transduction pathways leading to various responses, such as chemotaxis. In the chemokine system, multiple chemokines may activate a single chemokine receptor; for example, the receptor CCR1 ligates the RANTES (regulated on activation normal T cell expressed), MIP-1α (macrophage inflammatory protein) and MIP-1β chemokines. Likewise, a single chemokine may activate several receptors (Mantovani (1999)).

Monocytes and neutrophils, which play an important role in the pathogenesis of inflammation and in antigen presentation, respond to chemokines (Lee et al. (2000)). Monocytes express the chemokine receptors CCR1, CCR2, CCR5, CCR8, CXCR2, and CXCR4. (Uguccioni et al. (1995); Weber et al. (2000)). The ligands MIP-1α and Monocyte Chemoattractant Protein 1 (MCP1) have been reported as potent monocyte activators in vitro. (Fantuzzi et al. (1999).) Neutrophils are crucial during many acute inflammatory responses, and may also play a role in orienting immunity toward Th1 responses. (Bonecchi et al. (1999).) They mainly respond to some CXC chemokines but do not migrate to most of CC chemokines. Human neutrophils express two high affinity IL-8 receptors, CXCR1 and CXCR2.

The chemokine CKβ8, also known as CCL23; hmrp-2a; myeloid progenitor inhibitor factor 1 (MPIF-1); SCYA23 (current nomenclature and Genome ID system), is a 99-amino acid CC chemokine containing six cysteines. It is constitutively expressed in liver, lung, pancreas, and bone marrow. CKβ8 has chemotactic activity on monocytes, dendritic cells, and resting lymphocytes (Forssmann et al. (1997)) and inhibits colony formation of bone marrow-derived low proliferative potential colony-forming cells. (Patel et al. (1997)). CKβ8-1, an alternative splicing form of CKβ8 that is 116-amino acids in length, has been reported. Both the CKβ8 and CKβ8-1 mature forms have been assigned as ligands for the CCR1 receptor. (Youn et al. (1998)). Cross-desensitization studies in both monocytes and eosinophils indicate that CKβ8-1 binds predominately to the CCR1. Further processing at the $NH_2$-terminus of CKβ8 results in 76 or 75 residue proteins that are significantly more active on CCR1 expressing cells (Macphee et al. (1998), Berkhout et al. (2000)).

In addition to the chemokine receptors, neutrophils and monocytes also express the G protein-coupled N-formyl peptide receptor (FPR) and its homologue N-formyl peptide receptor like 1 (FPRL1). Since the ligands for FPRL1 were unknown when it was originally cloned, FPRL1 was initially defined as an orphan receptor. (Bao et al. (1992); Murphy et al. (1992); Ye et al. (1992).) It was assigned as a $LXA_4$ receptor since it binds lipoxin $A_4$ (Fiore et al. (1994).) In addition, several different peptides/proteins have been reported to bind FPRL1 with low affinity (see FIG. 1). A serum amyloid A, a protein secreted during the acute phase of inflammation, has been reported as a medial affinity functional ligand (Su et al. (1999)). A β amyloid fragment (1-42) and neurotoxic prion peptide 106-126 are also low affinity ligands, indicating that FPRL1 may play a role in neurodegenerative diseases (Le et al. (2001)). Some other low affinity ligands include: peptides derived from HIV envelope proteins (Su et al. (1999), Deng et al. (1999)); and a *Helicobacter pylori* peptide, Hp(2-20). Some synthetic peptides, such as Trp-Lys-Tyr-Met-Val-D-Met-$NH_2$ (WKYMVm) and Trp-Lys-Tyr-Met-Val-Met-$NH_2$ (WKYMVM) ("W peptides 1 and 2"), have been reported as potent ligands for the receptor. (Christophe et al. (2001); Baek et al. (1996)). However, these non-naturally occurring peptides derived from random hexapeptide libraries have not been shown to be physiologically relevant.

In 1979, the World Health Organization announced that small pox had been vanquished—almost 200 years after the first small pox vaccination (puss from a cow pox-infected milkmaid) had been administered to a young boy, James Phipps. His life was spared from small pox infection because Edward Jenner had discovered that milkmaids that had contracted cow pox rarely catch small pox. The success of such a risky procedure was due to the molecular similarity of cow pox to small pox. Phipps' immune system could immediately mount a specific response upon the introduction of small pox, quickly disposing of the invaders.

Since then, many vaccines have been developed to prevent infection from a wide variety of agents, such as infectious microorganisms (bacteria and viruses), toxins, and even tumors. Despite significant advances since the 1790s, many infectious agents are free to prey on susceptible individuals because no effective vaccines exist. A glaring example, now having devastating quality-of-life and economic effects in many parts of the world is the human immunodeficiency virus (HIV). In the cases where vaccines do exist, they often are not available to those people and countries which lack access to funds, technical expertise and labor for multiple administrations. Any reduction in necessary resources, such as the number of required administrations to afford protection, would facilitate vaccination (immunization) of greater numbers of individuals.

Vaccination exploits the immune system, which comprises leukocytes (white blood cells (WBCs): T and B lymphocytes, monocytes, eosinophils, basophils, and neutrophils), lymphoid tissues and lymphoid vessels. To combat infection, B and T lymphocytes circulate throughout the body, interact with antigen-presenting cells and detect pathogens. Once an invader is detected, cytotoxic T cells or antibody-secreting B cells specific for the foreign agent are recruited to the infection site to destroy it. The concept of vaccination is to generate the same types of host-protective immune responses without exposing the individual to the pathology-inducing foreign agent (such as a pathogen or tumor). Such immune responses may be, for example, cell-mediated and/or antibody based.

Key player in the adaptive immune response to foreign invaders are the antigen presenting cells (APCs), such as macrophages, activated B cells and dendritic cells. Dendritic cells are especially important in the immune response. Immature or resting dendritic cells reside in epithelial layers, phagocytosing foreign material (called antigens). These dendritic cells become activated by tumor necrosis factor (TNF) secreted by nearby macrophages that have been stimulated by the foreign material. These activated dendritic cells, laden with foreign antigens, travel through the lymphatic system to the nearest lymph node. There, resting naive (unexposed to antigen) T cells whose antigen-specific receptors recognize the foreign antigen are activated, and the immune system is triggered into action.

While vaccination can be accomplished with attenuated or dead infectious agents, the safest vaccinations are those that provoke an immune response to a subset of isolated antigens or epitopes, expressed by the foreign agent. However, many such antigens are by themselves are weakly immunogenic or incompetent for instigating a strong immune response. To enhance the effectiveness of such antigens, adjuvants are often added to vaccine compositions. Examples of adjuvants include oil emulsions of dead mycobacteria (Freund's complete), other dead bacteria (e.g., *B. pertussis*), bacterial polysaccharides, bacterial heat-shock proteins or bacterial DNA. While effective, many of these adjuvants cause significant inflammation and are not suitable for human administration.

Present immunization methods are not effective for all antigens, for all individuals, or for eliciting all forms of protective immunity. In addition, the number of useful adjuvants is small and directed mainly to antibody-related immunity and not to cell-mediated immunity. Moreover, there is a considerable lag time from immunization until the immune system provides protection for the subject. Improved vaccine compositions and/or effective safe adjuvants capable of inducing cell-mediated responses as well as antibody, would greatly aid current vaccination efforts.

SUMMARY

The inventors have discovered that the CKβ8-1 truncation variant, CKβ8-1 (25-116), is involved in inflammatory reactions and innate immunity through its role as a functional ligand for the formyl peptide receptor like 1 receptor (FPRL1). In addition, the inventors have discovered an alternatively spliced exon of CKβ8-1, named SHAAGtide, and truncated and other variants of SHAAGtide that, along with CKβ8-1 (25-116), are functional on both cells that are known to express FPRL1. Functional SHAAGtides generate calcium flux upon receptor-ligand binding in leukocytes and attract monocytes, neutrophils, mature dendritic cells (mDCs), and immature dendritic cells (iDCs).

In one embodiment, the invention encompasses SHAAGtides as well as proteins and peptides comprising SHAAGtides, with the exception of CKβ8-1 (25-116). In addition, the invention also includes nucleic acids encoding SHAAGtides, nucleic acids encoding proteins and peptides comprising SHAAGtides, antibodies specifically binding SHAAGtides, and fusion proteins comprising SHAAGtides.

In another embodiment, the invention encompasses compositions comprising SHAAGtides or proteins or peptides comprising a SHAAGtide sequence. Such compositions include those suitable for administration to a subject to enhance FPRL1 activity.

In a further embodiment, the invention encompasses kits comprising such compositions. Such kits may be assembled to facilitate administration of, for example, pharmaceutical compositions.

In another aspect, the invention encompasses methods of treating a subject for a disorder comprising modulating an activity of a FPRL1 receptor by administering a compound comprising of a SHAAGtide or proteins or peptides comprising a SHAAGtide sequence.

In a further aspect, the invention encompasses methods and kits useful for the identification of such antagonists are also encompassed by the present invention. Such methods comprise the step of contacting a FPRL1 receptor with a composition comprising a biologically active SHAAGtide, or protein or peptide comprising a SHAAGtide sequence, in the presence of a candidate antagonist molecule. Antagonists to FPRL1 receptor function may be identified as those compounds reducing receptor activity compared to that observed in the absence if the candidate compound.

In one aspect, the invention provides methods for eliciting an immune response to an antigen in a subject, such as in a human, wherein a polypeptide with at least a part of a sequence of SEQ ID NOS: 1, 3, 5, 6, 8, 11, and 16 ("SHAAGtides") is administered with an antigen to a subject. Such immune response may be antibody mediated, and upon administration, the titer of antigen-specific antibodies increases at least two-fold. In other aspects, the immune response is cell-mediated and the polypeptide having at least a portion of SEQ ID NOS:1, 3, 5, 6, 8, 11, and 16 attracts and/or activates various leukocytes, including dendritic cells.

In another aspect, the invention provides methods of eliciting an immune response by co-administering a polypeptide having at least a portion of the sequence SEQ ID NOS: 1, 3, 5, 6, 8, 11, and 16 with an antigen; in other aspects, the antigen and polypeptide may be administered separately. In yet other aspects, more than one polypeptide of SEQ ID NOS: 1, 3, 5, 6, 8, 11, and 16 may be administered, either separately or as concatamers or fusion proteins. In all cases, variants of SEQ ID NOS: 1, 3, 5, 6, 8, 11, and 16 may be used. Likewise, in other aspects, the polypeptides having at least a portion of SEQ ID NOS: 1, 3, 5, 6, 8, 11, and 16 may be administered as polynucleotides (SEQ ID NOS:20, 22, 24, 25, 27, 30, and 12) operably-linked such that they are expressed by the subject upon or after administration. Likewise, antigens may also be administered as polynucleotides that are expressed after administration.

In another aspect, the administered antigen is a polypeptide from a pathogen, such as Hepatitis, Influenza, tumor antigens or allergens.

The methods also provide the use of compositions containing the various SHAAGtide sequences incorporated into sustained release formulations. In yet other aspects, the methods also provide for the use of adjuvants in the administered compositioins. Such adjuvants include alum, incomplete Freund's adjuvant, a bacterial capsular polysaccharide, bacterial DNA, dextran, IL-12, GM-CSF, CD40 ligand, IFN-γ, IL-1, IL-2, IL-3, IL-4, IL-10, IL-1 3, IL-18 or a cytokine, or fragments thereof.

The methods of the invention also provide for the administration of multivalent carriers with the SHAAGtide and antigen molecules. The multivalent carrier may be linked to a SHAAGtide polypeptide, the antigen or an adjuvant. Examples of multivariant carriers include bacterial capsular polysaccharide (such as *Pneumococci, Streptococci* or *Meningococci* polysaccharides), a dextran and polynucleotide vectors.

In yet other aspects, the methods of invention provide for the administration of a pharmaceutical carrier with the SHAAGtide and antigen molecules.

In some aspects, sites of administration include solid tumors or tissues surrounding such tumors. Administration may be accomplished by any number of means, including injection, inhalation, or oral. Suppositories may also be used.

The methods of the invention also provide for multiple administrations of the SHAAGtide-containing compositions; administrations may of course be at the same or different site. In some instances, the administration site is removed from a target site of polypeptide delivery. For example, liposomes may be administered containing SHAAGtides and antigens, as well as incorporating molecules that enable the liposome to be targeted to specific tissues or cells.

In further aspects, the invention provides compositions having at least one SHAAGtide-containing polypeptide or fragment thereof; and at least one antigen. In some aspects, two different SHAAGtide peptides may be used. Such compositions may be formulated in sustained release formulations. Furthermore, the compositions of the invention may also incorporate a pharmaceutically acceptable carrier, which may be an adjuvant in some cases. Other pharmaceutically acceptable carriers include water, oil, saline, aqueous dextrose and glycerol.

In other aspects, the compositions may incorporate a cell, a microbial vector or viral vector expressing a polynucleotide, such as one encoding SHAAGtide sequences. The cell may be allogeneic or autologous. In yet more aspects, the compositions may also include tumor-associated antigens (which may be obtained from autologous cells), cancer cells, cells from cancer cell lines (such as human ovarian or human brain cancer).

In another aspect, the invention provides compositions formulated with at least one tumor cell; and at least one cell exogenously expressing at least one SHAAGtide polynucleotide sequence. The tumor cell may be a primary, autologous or allogenic. The tumor cell may also be a glioma, glioblastoma, gliosarcoma, astrocytoma, melanoma, breast cancer cell or an ovarian cancer cell. In other aspects, the tumor cell is a cancer cell.

In a final aspect, the invention provides for kits containing a pharmaceutical composition incorporating at least one SHAAGtide molecule (polypeptide and/or polynucleotide) and a syringe.

DESCRIPTION OF THE DRAWINGS

FIG. 1. Table showing reported FPRL1 endogenous low affinity ligands and non-natural ligands.

FIG. 2. Figure showing the amino acid sequence alignment of the human CCL23/CKβ8 variants with human CCL15/MIP-1α and CCL3/MIP-1δ.

DETAILED DESCRIPTION

The inventors have discovered that a CKβ8-1 truncation variant, CKβ8-1 (25-116), is a bifunctional ligand for two distinct GPCRs: the chemokine receptor CCR1 and the formyl peptide receptor like 1 receptor (FPRL1). The inventors have also discovered that, in addition to its activity as a CCR1 ligand, CKβ8-1(25-116) is involved in inflammatory reactions and immunity by recruiting monocytes and neutrophils through its role as a functional ligand for FPRL1. CKβ8 attracts cells including monocytes, dendritic cells and resting lymphocytes through OCR1, but lacks the alternatively-spliced exon found in CKβ8-1(25-116) (SHAAGtide sequence). CKβ8-1(1-116), the alternatively-spliced form of CKβ8 (116 amino acids) is a functional ligand for the CCR1 receptor, as is CKβ8. However, CKβ8-1(1-116) does not exert its functions through the SHAAGtide sequence.

The inventors have also discovered a class of novel peptides (the SHAAGtide peptide and variants of the SHAAGtide peptide—henceforth collectively known as "SHAAGtides"), truncation mutants of the splice exon of the CC chemokine CCL23, CKβ8-1(25-116), that are surprisingly effective and valuable ligands for the FPRL1 receptor. These peptides produce a calcium flux in leukocytes expressing the FPRL1. In addition, SHAAGtides effectively attract cells including monocytes, neutrophils, mature dendritic cells (mDCs) and immature dendritic cells (iDCs) and other leukocyte subsets. The SHAAGtide peptide (SEQ ID NO:1) and certain SHAAGtide variants, along with their parent chemokine CKβ8-1 (25-116), are functional on both monocytes and neutrophils that are known to express FPRL1. Functional SHAAGtides generate calcium flux upon receptor-ligand binding in leukocytes and attract monocytes, neutrophils, mature dendritic cells (mDCs), and immature dendritic cells (iDCs) in chemotactic assays. In light of these observations, the SHAAGtides represent cryptic functional peptides that are therefore surprisingly effective as FPRL1 ligands.

The invention encompasses SHAAGtides as well as proteins and peptides comprising SHAAGtides, with the exception of CKβ8-1 (25-116) and CKβ8-1 (1-116). In addition, the invention also includes nucleic acids encoding SHAAGtides, as well as nucleic acids encoding proteins and peptides comprising SHAAGtides, with the exception of nucleic acids encoding CKβ8-1 (25-116) ) and CKβ8-1 (1-116). Compositions containing the SHAAGtides as well as proteins and peptides comprising SHAAGtides, including CKβ8-1 (25-116) are also included in the invention. Such compositions include those suitable for administration to a subject to enhance FPRL1 activity. Also included are kits comprising such compositions. Such kits may be assembled to facilitate administration of, for example, pharmaceutical compositions.

The invention also encompasses methods of treating a subject in need of stimulation of inflammatory reactions and innate immunity. Stimulating such activity may benefit subjects suffering from diseases, for example, infectious diseases (and also in vaccination, as described in co-pending patent application "Methods and Compositions for Inducing an Immune Response", filed May 7th, 2002—Ser. No. 10/141, 508). Such methods comprise stimulating the FPRL1 receptor by administrating a composition comprising a SHAAGtide, a peptide or protein comprising a SHAAGtide, or other stimulatory molecule.

The invention also encompasses methods of treating a subject in need of a downregulation of inflammatory reactions and innate immunity. Downregulation of such activity may benefit subjects suffering from diseases including neurodegenerative disorders, such as Alzheimer's disease or Creutzfeldt-Jakob disease. Such methods comprise downregulating the FPRL1 receptor by administrating a composition comprising an antagonist to FPRL1 receptor function.

Methods and kits for the identification of such antagonists are also encompassed by the present invention. Such methods comprise the step of contacting a FPRL1 receptor with a composition comprising a biologically active SHAAGtide sequence, a peptide or protein comprising an active SHAAGtide, in the presence of a candidate antagonist molecule. Antagonists to FPRL1 receptor function may be identified as those compounds reducing receptor activity compared to that observed in the absence if the candidate compound. Such methods may be performed in vitro or in vivo. In addition, kits may be assembled to facilitate such in vitro or in vivo tests.

SHAAGtides and Molecules Comprising SHAAGtides.
SHAAGtide Peptides and Polypeptides Comprising SHAAGtides Table 1 shows the SHAAGtide polypeptide sequence (SEQ ID NO:1) and the polypeptide sequences of certain SHAAGtide truncated variants and other variants. Table 2 shows the SHAAGtide polynucleotide sequence (SEQ ID NO:20) and the polynucleotide sequences of SHAAGtide truncated variants and other variants. Table 3 shows the human CKβ8-1(25-116) Nucleotide Sequence (SEQ ID NO:12). FIG. 2 shows the amino acid sequence alignment of the human CCL23/CKβ8 variants (CKβ (1-99)—SEQ ID NO: 13; CKβ (25-99)—SEQ ID NO: 14; CKβ (1-116)—SEQ ID NO: 15; CKβ (25-116)—SEQ ID NO: 16) with human CCL15/MIP-1α (SEQ ID NO: 19); CCL3/MIP-1δ (SEQ ID NO: 17) and Leukotactin (SEQ ID NO: 18). Four conserved cysteine residues are shown in boxes and two additional cysteines, not normally found in the CC chemokine family, are shown in dashed boxes. The alternatively spliced exon of CCL23/CKβ8-1 is shown underlined.

TABLE 1

SHAAGtide and various truncated and other variants - amino acid sequences.

| SEQ ID NO: | Designation and FPRL1 Activity | Amino acid sequence |
|---|---|---|
| 1 | CCXP1 Native sequence; high activity | Met Leu Trp Arg Arg Lys Ile Gly Pro<br>1 5<br>Gln Met Thr Leu Ser His Ala Ala Gly<br>10 15 18 |
| 2 | CCXP2 Low activity | Arg Arg Lys Ile Gly Pro Gln Met Thr<br>1 5<br>Leu Ser His Ala Ala Gly<br>10 15 |
| 3 | CCXP3 High activity | Met Leu Trp Arg Arg Lys Ile Gly Pro<br>1 5<br>Gln Met Thr Leu Ser His<br>10 15 |

TABLE 1-continued

SHAAGtide and various truncated and other variants - amino acid sequences.

| SEQ ID NO: | Designation and FPRL1 Activity | Amino acid sequence |
|---|---|---|
| 4 | CCXP4 Low activity | Ile Gly Pro Gln Met Thr Leu Ser His<br>1 5<br>Ala Ala Gly<br>10 |
| 5 | CCXP5 Moderate activity | Met Leu Trp Arg Arg Lys Ile Gly Pro<br>1 5<br>Gln Met Thr<br>10 |
| 6 | CCXP6 high activity | Met Leu Trp Arg Arg Lys Ile Gly Pro<br>1 5<br>Gln Met Thr Leu Ser His Ala Ala Tyr<br>10 15 18 |
| 7 | CCXP7 Low activity | Trp Arg Arg Lys Ile Gly Pro Gln Met<br>1 5<br>Thr Leu Ser His Ala Ala Gly<br>10 15 |
| 8 | CCXP8 Moderate activity | Met Leu Trp Arg Arg Lys Ile Gly Pro<br>1 5<br>Gln Met<br>10 |
| 9 | CCXP9 Low activity | Trp Arg Arg Lys Ile Gly Pro Gln Met<br>1 5 |
| 10 | CCXP10 Low activity | Trp Arg Arg Lys Ile Gly<br>1 5 |
| 11 | CCXP11 Moderate activity | Leu Trp Arg Arg Lys Ile Gly Pro Gln<br>1 5<br>Met Thr Leu Ser His<br>10 |

TABLE 2

SHAAGtide and various truncated and other variants - polynucleotide sequences

| SEQ ID NO: | Polynucleotide sequence | |
|---|---|---|
| 20 | atgctctgga ggagaaagat tggtcctcag atgacccttt<br>ctcatgctgc agga | 54 |
| 21 | aggagaaaga ttggtcctca gatgaccctt tctcatgctg<br>cagga | |
| 22 | atgctctgga ggagaaagat tggtcctcag atgacccttt<br>ctcat | 45 |
| 23 | attggtcctc agatgaccct ttctcatgct gcagga | |
| 24 | atgctctgga ggagaaagat tggtcctcag atgacc | 36 |
| 25 | atgctctgga ggagaaagat tggtcctcag atgacccttt<br>ctcatgctgc atat | 54 |
| 26 | tggaggagaa agattggtcc tcagatgacc ctttctcatg<br>ctgcagga | |
| 27 | atgctctgga ggagaaagat tggtcctcag atg | 33 |
| 28 | tggaggagaa agattggtcc tcagatg | |

TABLE 2-continued

SHAAGtide and various truncated and other
variants - polynucleotide sequences

| SEQ ID NO: | Polynucleotide sequence | |
|---|---|---|
| 29 | tggaggagaa agattggt | |
| 30 | ctctggagga gaaagattgg tcctcagatg acccttctc at | 42 |

TABLE 3

Human CKβ8-1(25-116) Nucleotide Sequence (SEQ ID NO: 12)

| | |
|---|---|
| atgctctgga ggagaaagat tggtcctcag atgaccctttt ctcatgctgc aggattccat | 60 |
| gctactagtg ctgactgctg catctcctac accccacgaa gcatcccgtg ttcactcctg | 120 |
| gagagttact ttgaaacgaa cagcgagtgc tccaagccgg gtgtcatctt cctcaccaag | 180 |
| aaggggcgac gtttctgtgc caaccccagt gataagcaag ttcaggtttg catgagaatg | 240 |
| ctgaagctgg acacacggat caagaccagg aagaattga | 279 |

SHAAGtide Molecules, Derivatives and Analogs

SHAAGtide peptides of the present invention include those molecules listed in Table 1. In addition, various other derivatives of SHAAGtide peptides and nucleotides may be synthesized using standard techniques. Derivatives are nucleic acid sequences or amino acid sequences formed from native compounds either directly or by modification or partial substitution. Analogs are nucleic acid sequences or amino acid sequences that have a structure similar, but not identical, to the native compound but differ from it in respect to certain components or side chains. Analogs may be synthesized or from a different evolutionary origin.

Derivatives and analogs may be full length or other than full length, if the derivative or analog contains a modified nucleic acid or amino acid. For example, SEQ ID NO:3 contains only the first N-terminal 15 amino acids of the SHAAGtide molecule (SEQ ID NO:1). Derivatives or analogs of the SHAAGtide nucleic acid or peptide include, but are not limited to, molecules comprising regions that are substantially homologous to the SHAAGtide nucleic acid or peptide by at least about 70%, 80%, or 95% identity over a nucleic acid or amino acid sequence of identical size or when compared to an aligned sequence in which the alignment is done by a homology algorithm, or whose encoding nucleic acid is capable of hybridizing to a complementary sequence encoding the aforementioned peptide sequences under stringent, moderately stringent, or low stringent conditions. (Ausubel et al., 1987.) A complementary nucleic acid molecule is one that is sufficiently complementary to a sequence, such that hydrogen bonds are formed with few mismatches, forming a stable duplex. "Complementary" refers to Watson-Crick or Hoogsteen base pairing between nucleotides.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favor specific hybridizations (high stringency), which can be used to identify, for example, full-length clones from a library. Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach is to vary the temperature: higher relative temperatures result in more stringent reaction conditions. (Ausubel et al., 1987) provide an excellent explanation of stringency of hybridization reactions.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" conditions enable a probe, primer or oligonucleotide to hybridize only to its target sequence. Stringent conditions are sequence-dependent and will differ. Stringent conditions comprise: (1) low ionic strength and high temperature washes (e.g. 15 mM sodium chloride, 1.5 mM sodium citrate, 0.1% sodium dodecyl sulfate at 50° C.); (2) a denaturing agent during hybridization (e.g. 50% (v/v) formamide, 0.1% bovine serum albumin, 0.1% Ficoll, 0.1% polyvinylpyrrolidone, 50 mM sodium phosphate buffer (pH 6.5; 750 mM sodium chloride, 75 mM sodium citrate at 42° C.); or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent (Sambrook, 1989), such that a polynucleotide will hybridize to the entire, fragments, derivatives or analogs of SEQ ID NOS:7-12, 14. One example comprises hybridization in 6×SSC, 5×

Denhardt's solution, 0.5% SDS and 100 mg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (Ausubel et al., 1987; Kriegler, 1990).

"Low stringent conditions" use washing solutions and hybridization conditions that are less stringent than those for moderate stringency (Sambrook, 1989), such that a polynucleotide will hybridize to the entire, fragments, derivatives or analogs of SEQ ID NOS:7-12, 14. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency, such as those for cross-species hybridizations are well-described (Ausubel et al., 1987; Kriegler, 1990; Shilo and Weinberg, 1981).

In addition to naturally-occurring allelic variants of SHAAGtide, changes can be introduced by mutation into SEQ ID NO:1 that incur alterations in the amino acid sequences of the encoded SHAAGtide that do not significantly alter SHAAGtide function. For example, an amino acid substitution at the C-terminal amino acid residue has be made in the sequence of SEQ ID NO:6. A "non-essential" amino acid residue is a residue that can be altered from the wild-type sequences of the SHAAGtide without altering biological activity, whereas an "essential" amino acid residue is required for such biological activity. For example, amino acid residues that are conserved among the SHAAGtide of the invention are predicted to be particularly non-amenable to alteration. Amino acids for which conservative substitutions can be made are well known in the art.

Useful conservative substitutions are shown in Table 4, "Preferred substitutions." Conservative substitutions whereby an amino acid of one class is replaced with another amino acid of the same type fall within the scope of the invention so long as the substitution does not materially alter the biological activity of the compound.

TABLE 4

| Preferred substitutions | | |
|---|---|---|
| Original residue | Exemplary substitutions | Preferred substitutions |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |

TABLE 4-continued

| Preferred substitutions | | |
|---|---|---|
| Original residue | Exemplary substitutions | Preferred substitutions |
| Trp (W) | Tyr, Phe | Tyr |
| Tyr (Y) | Trp, Phe, Thr, Ser | Phe |
| Val (V) | Ile; Leu, Met, Phe, Ala, Norleucine | Leu |

Non-conservative substitutions that effect (1) the structure of the polypeptide backbone, such as a β-sheet or α-helical conformation, (2) the charge, (3) hydrophobicity, or (4) the bulk of the side chain of the target site can modify SHAAGtide function, especially when a SHAAGtide sequences comprises a part of a larger polypeptide molecule. Residues are divided into groups based on common side-chain properties as denoted in Table 5. Non-conservative substitutions entail exchanging a member of one of these classes for another class. Substitutions may be introduced into conservative substitution sites or more preferably into non-conserved sites.

TABLE 5

| Amino acid classes | |
|---|---|
| Class | Amino acids |
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce the SHAAGtide variant DNA (Ausubel et al., 1987; Sambrook, 1989).

An "isolated" or "purified" SHAAGtides of the present invention comprise polypeptides, proteins or biologically active fragments separated and/or recovered from a component of its natural environment. Isolated SHAAGtides include those expressed heterologously in genetically engineered cells or expressed in vitro.

Contaminant components include materials that would typically interfere with diagnostic or therapeutic uses for the polypeptide. To be substantially isolated, preparations having less than 30% by dry weight of non-SHAAGtide contaminating material (contaminants), more preferably less than 20%, 10% and most preferably less than 5% contaminants.

Polypeptides and fragments of interest can be produced by any method well known in the art; such as by expression via vectors such as bacteria, viruses and eukaryotic cells. In addition, in vitro synthesis, such as peptide synthesis, may be also used.

An "active polypeptide or polypeptide fragment" retains a biological and/or an immunological activity similar, but not necessarily identical, to an activity of a SHAAGtide polypeptide shown in Table 1. Immunological activity, in the context of this immediate discussion of the polypeptide per se, and not an actual biological role for SHAAGtide in eliciting or enhancing FPRL1 activity, refers to an aspect of a SHAAGtide polypeptide in that a specific antibody against a SHAAGtide antigenic epitope binds a SHAAGtide. Biological activity refers to a function, either inhibitory or stimulatory, caused by a native SHAAGtide polypeptide. A biological activity of SHAAGtide polypeptide includes, for example, binding to the FPRL1 receptor, or chemotaxis or eliciting calcium flux upon FPRL1 receptor binding. A particular biological assay (see Examples), with or without dose dependency, can be used to determine SHAAGtide activity. A nucleic acid fragment encoding a biologically-active portion of SHAAGtide can be prepared by isolating a polynucleotide sequence that encodes a polypeptide having a SHAAGtide biological activity, expressing the encoded portion of SHAAGtide (e.g., by recombinant expression in vitro) and assessing the activity of the encoded portion of SHAAGtide polypeptide.

In general, a SHAAGtide polypeptide variant that preserves SHAAGtide polypeptide-like function and includes any variant in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

Table 1 shows that the deletion of amino acids at the C-terminal of the SHAAGtide sequence is less likely to cause a loss of FPRL1 activity than deletion at the N-terminal (see Example 9). For example, SEQ ID NO:8, consisting of the 11 N-terminal amino acids of the SHAAGtide sequence still retains moderate FPRL1 activity. However, deletion of 3 N-terminal amino acids (SEQ ID NO:2) results in only a low FPRL1 activity. Nevertheless, the deletion of the terminal amino acid at the N-terminal (SEQ ID NO:11) does not result in a complete loss in FRPL1 activity.

"SHAAGtide variant" means an active SHAAGtide polypeptide having at least: (1) about 80% amino acid sequence identity with a full-length native sequence SHAAGtide polypeptide sequence or (2) any fragment of a full-length SHAAGtide polypeptide sequence. For example, SHAAGtide polypeptide variants include SHAAGtide polypeptides wherein one or more amino acid residues are added or deleted at the N- or C-terminus of the full-length native amino acid sequence, with the exception of those fragments that are identical to CKβ8 and CKβ8-1. A SHAAGtide polypeptide variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native sequence SHAAGtide polypeptide sequence. Ordinarily, SHAAGtide variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues in SHAAGtide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\text{\% amino acid sequence identity} = X/Y \cdot 100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Fusion polypeptides are useful in expression studies, cell-localization, bioassays, and SHAAGtide purification. A SHAAGtide "chimeric protein" or "fusion protein" comprises SHAAGtide fused to a non-SHAAGtide polypeptide. A non-SHAAGtide polypeptide is not substantially homologous to a SHAAGtide polypeptide. A SHAAGtide fusion protein may include any portion to the entire SHAAGtide, including any number of the biologically active portions. For example, SHAAGtide may be fused to the C-terminus of the GST (glutathione S-transferase) sequences. Such fusion proteins facilitate the purification of recombinant SHAAGtide. In certain host cells, (e.g. mammalian), heterologous signal sequences fusions may ameliorate SHAAGtide expression and/or secretion.

Antibodies specific to the SHAAGtide and SHAAGtide variant sequences are also encompassed by the invention. Methods of producing polyclonal and monoclonal antibodies, including binding fragments (e.g., $F_{(ab)2}$) and single chain versions are well known. Hence, polyclonal or monoclonal antibodies can be prepared by standard techniques.

The chemotactic compositions of the invention contain one or more polynucleotides or polypeptides containing a SHAAGtide sequence. In an embodiment, the composition contains a SHAAGtide that is an isolated or recombinant polynucleotide or polypeptide. In an embodiment, the SHAAGtide(s) is/are the predominant species (i.e., greater than about 50%, more often greater than about 80% by weight of the total of the members of the class of molecule in the composition) of its class (e.g., polypeptide, polynucleotide, lipid, carbohydrate) in the composition. The chemotactic compositions of the invention contain SHAAGtides free of materials normally associated with their in situ environment (if naturally occurring).

An isolated SHAAGtide nucleic acid molecule is purified from the setting in which it is found in nature and is separated from at least one contaminant nucleic acid molecule. Isolated SHAAGtide molecules are distinguished from the specific SHAAGtide molecule, as it exists in cells.

The inventors have discovered a class of novel peptides (SHAAGtides), truncation mutants of a splice variant of the CC chemokine CCL23, CKβ8-1, that is able to modulate and/or enhance an immune responses in vitro and in vivo. To modulate an immune response is to influence the classes and subtypes of produced immunoglobulins (Ig's) and the number and type of cells (e.g., cytotoxic T cells, eosinophils, and mast cells) that localize to the site of infection. SHAAGtides act as ligands to a receptor because calcium flux in leukocytes is seen upon addition of these peptides. SHAAGtides effectively attract monocytes, neutrophils and mature dendritic cells (mDCs), as well as immature dendritic cells (iDCs). CKβ8 (CCL23, also known as myeloid progenitor inhibitor factor 1 or MPIF-1; 99 amino acids), a related molecule of CKβ-1, attracts monocytes, dendritic cells and resting lymphocytes (Forssmann et al., 1997), but lacks the alternatively-spliced exon encoding SHAAGtide sequences. CKβ8-1 (residues 1-116), an alternative spliced form of CKβ8 is a functional ligand for the CCR1 receptor, as is CKβ8 (Youn et al., 1998). However, CKβ8-1 (1-116) does not exert its functions through the SHAAGtide sequences. In light of these observations, the SHAAGtide sequences represent cryptic functional peptides that are therefore surprisingly effective as adjuvants and immunomodulators.

Without intending to be bound by a particular mechanism, it is believed that the SHAAGtide polypeptides promote an immune reaction to the immunogen by recruiting APCs to site of administration. Immunogens (antigens) are ingested by APCs and partially degraded. Subsequently, a fraction of the degraded antigen is presented associated with MHC class I or II molecules on the surface of the APC. Upon presentation to waiting T cells in a nearby lymph node, proliferation of cytotoxic T cells or helper T cells is stimulated, or antibody production and secretion by B cells is activated.

Because SHAAGtides act as effective molecular beacons to attract cells of the immune system, the immune response is enhanced and/or modulated. When used in vaccines, SHAAGtides enhance the immune response such that antigens that usually do not elicit (or weakly elicit) such a response do so; use of SHAAGtides can also decrease the need for subsequent booster injections. SHAAGtides can also modify the type of generated immune response.

The invention encompasses compositions containing SHAAGtide or nucleic acids encoding SHAAGtides and their prophylactic uses, as well as treating disease conditions. The SHAAGtide polypeptide sequence (SEQ ID NO:1) and some active variants (SEQ ID NOS: 3, 5, 6, 8, 11, and 16) are shown in Tables 6 and 8; the polynucleotide sequences that encode SEQ ID NOS:1, 3, 5, 6, 8, 11, respectively, are shown in Table 9 (SEQ ID NOS:20, 22, 24, 25, 27, and 30).

TABLE 6

Human SHAAGtide polypeptide sequence and some active variants

| SEQ ID NO: | Notes | Amino acid sequence |
|---|---|---|
| 1 | Native sequence; high activity | Met Leu Trp Arg Arg Lys Ile Gly Pro<br>1                      5<br>Gln Met Thr Leu Ser His Ala Ala Gly<br>10               15           18 |
| 3 | High activity | Met Leu Trp Arg Arg Lys Ile Gly Pro<br>1                      5<br>Gln Met Thr Leu Ser His<br>10               15 |
| 5 | Moderate activity | Met Leu Trp Arg Arg Lys Ile Gly Pro<br>1                      5<br>Gln Met Thr<br>10 |

TABLE 6-continued

Human SHAAGtide polypeptide sequence and some active variants

| SEQ ID NO: | Notes | Amino acid sequence |
|---|---|---|
| 6 | Very effective as adjuvant; high activity | Met Leu Trp Arg Arg Lys Ile Gly Pro<br>1                      5<br>Gln Met Thr Leu Ser His Ala Ala Tyr<br>10               15           18 |
| 8 | Moderate activity | Met Leu Trp Arg Arg Lys Ile Gly Pro<br>1                      5<br>Gln Met<br>10 |
| 11 | Moderate activity | Leu Trp Arg Arg Lys Ile Gly Pro Gln<br>1                      5<br>Met Thr Leu Ser His<br>10 |

TABLE 7

Human SHAAGtide polynucleotide sequence (SEQ ID NO: 3)

| SEQ ID NO: | Polynucleotide sequence | |
|---|---|---|
| 20 | atgctctgga ggagaaagat tggtcctcag atgacccttt ctcatgctgc agga | 54 |
| 22 | atgctctgga ggagaaagat tggtcctcag atgacccttt ctcat | 45 |
| 24 | atgctctgga ggagaaagat tggtcctcag atgacc | 36 |
| 25 | atgctctgga ggagaaagat tggtcctcag atgacccttt ctcatgctgc atat | 54 |
| 27 | atgctctgga ggagaaagat tggtcctcag atg | 33 |
| 30 | ctctggagga gaaagattgg tcctcagatg accctttctc at | 42 |

Another derivative of CKβ8-1 that has SHAAGtide-like activity (CKβ8-1 (25-116; SEQ ID NO:16), is shown in Table 8; the nucleotide sequence that encodes SEQ ID NO:16 is shown in Table 9. The sequences corresponding to SEQ ID NOS:1 and 20 are underlined.

TABLE 8

Polypeptide sequence of CKβ8-1 (25-116)
(SEQ ID NO: 16)

<u>Met Leu Trp Arg Arg Lys Ile Gly Pro Gln Met Thr Leu Ser His Ala</u>
1               5                   10                      15

<u>Ala Gly</u> Phe His Ala Thr Ser Ala Asp Cys Cys Ile Ser Tyr Thr Pro
            20                  25                  30

Arg Ser Ile Pro Cys Ser Leu Leu Glu Ser Tyr Phe Glu Thr Asn Ser
            35                  40                  45

Glu Cys Ser Lys Pro Gly Val Ile Phe Leu Thr Lys Lys Gly Arg Arg
        50                  55                  60

Phe Cys Ala Asn Pro Ser Asp Lys Gln Val Gln Val Cys Met Arg Met
65                  70                  75                  80

Leu Lys Leu Asp Thr Arg Ile Lys Thr Arg Lys Asn
                85                  90

TABLE 9

Polynucleotide sequence of CKβ8-1 (25-116)
(SEQ ID NO: 12)

atgctctgga ggagaaagat tggtcctcag atgacccttt ctcatgctgc aggattccat    60
gctactagtg ctgactgctg catctcctac accccacgaa gcatcccgtg ttcactcctg   120
gagagttact ttgaaacgaa cagcgagtgc tccaagccgg tgtcatctt cctcaccaag    180 aaggggcgac gtttctgtgc caaccccagt gataagcaag ttcaggtttg catgagaatg   240
ctgaagctgg acacacggat caagaccagg aagaattga                          279

The "parent" sequences of SEQ ID NOS:1, 3, 5, 6, 8, and 11 are shown in Table 10 (SEQ ID NO:31; CKβ8-1 polypeptide) and Table 11 (SEQ ID NO:32, CKβ8-1 polynucleotide). SHAAGtide sequences are underlined. Note that CKβ8-1 (SEQ ID NO:31), while containing the SHAAGtide sequence (SEQ ID NO:1), does not possess the same activities as SEQ ID NO:1 by itself.

TABLE 10

Polypeptide sequence of CKβ8-1 (SEQ ID NO: 31)

Met Lys Val Ser Val Ala Ala Leu Ser Cys Leu Met Leu Val Thr Ala
1               5                   10                      15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp <u>Met Leu Trp</u>
            35                  40                  45

<u>Arg Arg Lys Ile Gly Pro Gln Met Thr Leu Ser His Ala Ala Gly</u> Phe
        50                  55                  60

His Ala Thr Ser Ala Asp Cys Cys Ile Ser Tyr Thr Pro Arg Ser Ile
65                  70                  75                  80

Pro Cys Ser Leu Leu Glu Ser Tyr Phe Glu Thr Asn Ser Glu Cys Ser
                85                  90                  95

Lys Pro Gly Val Ile Phe Leu Thr Lys Lys Gly Arg Arg Phe Cys Ala
            100                 105                 110

Asn Pro Ser Asp Lys Gln Val Gln Val Cys Met Arg Met Leu Lys Leu
            115                 120                 125

Asp Thr Arg Ile Lys Thr Arg Lys Asn
            130                 135

TABLE 11

Polynucleotide sequence of CKβ8-1 (SEQ ID NO: 32)

```
atgaaggtct ccgtggctgc cctctcctgc ctcatgcttg ttactgccct tggatcccag    60
gcccgggtca caaaagatgc agagacagag ttcatgatgt caaagcttcc attggaaaat   120
ccagtacttc tggacatgct ctggaggaga aagattggtc ctcagatgac cctttctcat   180
gctgcaggat tccatgctac tagtgctgac tgctgcatct cctacacccc acgaagcatc   240
ccgtgttcac tcctggagag ttactttgaa acgaacagcg agtgctccaa gccgggtgtc   300
atcttcctca ccaagaaggg gcgacgtttc tgtgccaacc ccagtgataa gcaagttcag   360
gtttgcatga gaatgctgaa gctggacaca cggatcaaga ccaggaagaa ttga         414
```

Compositions that include SHAAGtide polypeptide or polynucleotide include those suitable for administration to a subject to enhance an immune response, such as in response to vaccination. Also included are kits that include SHAAGtide polypeptide and/or SHAAGtide nucleotide. Such kits may be assembled to facilitate administration of, for example, pharmaceutical compositions.

The methods of the invention include administering a SHAAGtide (SEQ ID NOS:1, 3, 5, 6, 8, 11, and 16) or SHAAGtide nucleic acid (SEQ ID NOS:20, 22, 24, 25, 27, 30, and 12) composition to a subject.

When used to enhance or modulate an immune response, SHAAGtides may be administered as polypeptide or as polynucleotides that are expressed in vivo. To further facilitate such methods, SHAAGtide polypeptides may be associated (covalently or non-covalently) to the antigen of interest. In some instances, SHAAGtides in either form may be administered prior to or after administration of the antigen. When SHAAGtide compositions are administered separately from antigen (immunogen) compositions, the compositions are administered at the same physical location in a subject.

The methods of the invention, when enhancing, eliciting or modulating an immune response, include administering SHAAGtide compositions containing the immunogens of interest. In other methods, SHAAGtide compositions may be administered in the absence of immunogens. For example, a SHAAGtide composition is first administered, followed by a second administration of immunogen, with or without SHAAGtide polypeptides. In some cases, the immunogen-containing composition is administered first, followed by administration of a SHAAGtide-containing composition. The different compositions may be administered simultaneously, closely in sequence, or separated in time, e.g., one hour to two weeks or more.

To promote and/or modulate an immune response to tumors and cancers, SHAAGtide compositions are administered at the sites of abnormal growth or directly into the tissue (i.e., a tumor). Tumor or cancer antigens are then detected by the SHAAGtide-recruited or activated leukocytes, such as dendritic cells. By provoking an immune response to these antigens, tumors and cancers are attacked by the body and are reduced or eliminated. As such, these methods represent treatments for conditions involving uncontrolled or abnormal cell growth, e.g., tumors and cancers. Immune responses to tumors and cancers may also be promoted and/or modulated by administering isolated polypeptide tumor antigens with SHAAGtides. SHAAGtides may either be conjugated to the antigen or unconjugated.

New methods and reagents are now provided for therapeutic and prophylactic immunization (i.e., the deliberate provocation, enhancement, intensification or modulation of an adaptive and/or innate immune response). Particular advantages over prior immunization methods include one or more of the following:

(1) an accelerated immune response following administration of immunogen, (2) greater sensitivity to small amounts of immunogen (e.g., toxin or pathogen) or antigens that do not habitually provoke strong immune responses, and (3) more effective anti-tumor therapies.

While current vaccines are effective against many pathogenic agents, some dangerous pathogens (such as HIV, cancer and tumor cells, etc.) as of yet do not have suitable vaccines. In some instances, the difficulties partly stem from the properties of candidate foreign antigens, such as insolubility of HIV glycoproteins (e.g., gp120) or the poor immunogenicity of tumor antigens. Thus a composition that augments and/or modulates immune responses will be helpful to prepare new and effective vaccines.

The SHAAGtide polypeptides are truncations of a splice variant of the CKβ8-1 chemokine. Chemokines act as molecular beacons for the recruitment and activation of T lymphocytes, neutrophils, monocytes and macrophages, flagging pathogen battlegrounds. Chemokines, a group of greater than 40 small peptides (7-10 kD), ligate receptors expressed on WBCs that signal through G-protein-coupled signaling cascades to mediate their chemotractant and chemostimulant functions. Receptors may bind more than one ligand; for example, the receptor CCR1 ligates RANTES (regulated on activation normal T cell expressed), MIP-1α (macrophage inflammatory protein) and MIP-1β chemokines. To date, 24 chemokine receptors are known. The sheer number of chemokines, multiple ligand binding receptors, and different receptor profiles on WBCs allow for tightly controlled and specific immune responses (Rossi and Zlotnik, 2000). Chemokine activity can be controlled through the modulation of their corresponding receptors, treating related inflammatory and immunological diseases and enabling organ and tissue transplants.

Exploiting the activities of the SHAAGtide polypeptides, the immune response such as elicited during vaccination can be enhanced and/or modulated. That is, the vigor and/or magnitude and/or quality of the immune response is increased. For example, the early appearance and/or a high titer and/or avidity of antigen-specific antibodies indicates a vigorous immune response. The magnitude is augmented at least two-fold up to ten-fold or even hundred-fold compared to traditional vaccination methods. Enhancing or modulating the immune response's quality includes the production of high affinity antibodies to the immunogen and/or a higher concentration of preferred immunoglobulin classes, e.g., IgGs. Modulating the quality of the immune response also includes inducing different subsets of T lymphocytes that are distinguished by different subsets of cytokines and/or chemokines and/or the co-stimulatory molecules they produce. Modulating the quality of the immune response also includes inducing antigen-specific cytotoxic T cells and/or antibodies of different isotypes.

To distinguish between genes (and related nucleic acids) and the proteins that they encode, the abbreviations for genes are indicated by italicized (or underlined) text while abbreviations for the proteins are not italicized. Thus, SHAAGtide or SHAAGtide refers to the nucleotide sequence that encodes SHAAGtide.

"Control sequences" are DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

Nucleic acid is "operably-linked" when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation.

An "isolated" nucleic acid molecule is purified from the setting in which it is found in nature and is separated from at least one contaminant nucleic acid molecule. Isolated SHAAGtide molecules are distinguished from the specific SHAAGtide molecule, as it exists in cells.

An isolated SHAAGtide nucleic acid molecule comprises a nucleic acid molecule that is a complement of the nucleotide sequence shown in SEQ ID NOS:20, 22, 24, 25, 27, 30, and 12, or a portion of this nucleotide sequence. A "complementary nucleic acid molecule" is one that is sufficiently complementary to a sequence, e.g., SEQ ID NOS: 20, 22, 24, 25, 27, and 30, such that hydrogen bonds are formed with few mismatches, forming a stable duplex. "Complementary" refers to Watson-Crick or Hoogsteen base pairing between nucleotides.

"Derivatives" are nucleic acid sequences (or amino acid sequences) formed from native compounds either directly or by modification or partial substitution. "Analogs" are nucleic acid sequences or amino acid sequences that have a structure similar, but not identical, to the native compound but differ from it in respect to certain components or side chains. Analogs may be synthesized or from a different evolutionary origin. Homologs are nucleic acid sequences or amino acid sequences of a particular gene that are derived from different species.

Derivatives and analogs may be full length or other than full length, if the derivative or analog contains a modified nucleic acid or amino acid. Derivatives or analogs of the nucleic acids or proteins of SHAAGtide include, but are not limited to, molecules comprising regions that are substantially homologous to the nucleic acids or proteins of SHAAGtide by at least about 70%, 80%, or 95% identity over a nucleic acid or amino acid sequence of identical size or when compared to an aligned sequence in which the alignment is done by a homology algorithm, or whose encoding nucleic acid is capable of hybridizing to the complement of a sequence encoding the aforementioned proteins under stringent, moderately stringent, or low stringent conditions (Ausubel et al., 1987).

"Homologous" nucleotide sequences encode those sequences coding for isoforms of SHAAGtide. For SHAAGtide, homologous nucleotide sequences include nucleotide sequences encoding for a SHAAGtide of species other than humans, such as vertebrates, e.g., frog, mouse, rat, rabbit, dog, cat, cow and horse. Homologous nucleotide sequences also include naturally occurring allelic variations and mutations of the nucleotide sequences. A homologous nucleotide sequence does not, however, include the exact nucleotide sequence encoding human SHAAGtide. Homologous nucleic acid sequences include those nucleic acid sequences that encode conservative amino acid substitutions as well as a polypeptide possessing SHAAGtide biological activity.

In addition to the SHAAGtide sequences shown in SEQ ID NOS: 20, 22, 24, 25, 27, 30, and 12, DNA sequence polymorphisms that change the amino acid sequences of the SHAAGtide may exist within a population. For example, allelic variation among individuals will exhibit genetic polymorphism in SHAAGtide. The terms "gene" and "recombinant gene" refer to nucleic acid molecules comprising an open reading frame (ORF) encoding SHAAGtide, preferably a vertebrate SHAAGtide. Such natural allelic variations can typically result in 1-5% variance in SHAAGtide. "SHAAGtide variant polynucleotide" or "SHAAGtide variant nucleic acid sequence" means a nucleic acid molecule which encodes an active SHAAGtide that (1) has at least about 80% nucleic acid sequence identity with a nucleotide acid sequence encoding a full-length native SHAAGtide, (2) a full-length native SHAAGtide lacking the signal peptide, or (3) any other fragment of a full-length SHAAGtide. Ordinarily, an SHAAGtide variant polynucleotide will have at least about 80% nucleic acid sequence identity, more preferably at least about 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence encoding a full-length native SHAAGtide. A SHAAGtide variant polynucleotide may encode full-length native SHAAGtide lacking the signal peptide, or any other fragment of a full-length SHAAGtide. Variants do not encompass the native nucleotide sequence.

Ordinarily, SHAAGtide variant polynucleotides are at least about 30 nucleotides in length, often at least about 60, 90, 120, 150, 180, 210, 240, 270, 300, 450, 600 nucleotides in length, more often at least about 900 nucleotides in length, or more.

"Percent (%) nucleic acid sequence identity" with respect to SHAAGtide-encoding nucleic acid sequences identified herein is defined as the percentage of nucleotides in SHAAGtide that are identical with the nucleotides in a candidate sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

$$\% \text{ nucleic acid sequence identity} = W/Z \cdot 100$$

where

W is the number of nucleotides scored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

Stringency

Homologs (i.e., nucleic acids encoding SHAAGtide derived from species other than human) or other related sequences (e.g., paralogs) can be obtained by low, moderate or high stringency hybridization with all or a portion of the particular human sequence as a probe using methods well known in the art for nucleic acid hybridization and cloning. Stryngent conditions were described above.

In addition to naturally-occurring allelic variants of SHAAGtide, changes can be introduced by mutation into SEQ ID NOS: 20, 22, 24, 25, 27, 30, and 12 that incur alterations in the amino acid sequences of the encoded SHAAGtide that do not alter SHAAGtide function. For example, nucleotide substitutions leading to amino acid substitutions at "non-essential" amino acid residues can be made in the sequence of SEQ ID NOS:5 or 6. A "non-essential" amino acid residue is a residue that can be altered from the wild-type sequences of the SHAAGtide without altering biological activity, whereas an "essential" amino acid residue is required for such biological activity. For example, amino acid residues that are conserved among the SHAAGtide of the invention are predicted to be particularly non-amenable to alteration. Amino acids for which conservative substitutions can be made are well known in the art.

Useful conservative substitutions are shown in Table 4, "Preferred substitutions." Conservative substitutions whereby an amino acid of one class is replaced with another amino acid of the same type fall within the scope of the invention so long as the substitution does not materially alter the biological activity of the compound. If such substitutions result in a change in biological activity, then more substantial changes, indicated in Table 5 as exemplary, are introduced and the products screened for SHAAGtide polypeptide biological activity.

The variant polypeptides can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce the SHAAGtide variant DNA (Ausubel et al., 1987; Sambrook, 1989).

An "isolated" or "purified" polypeptide, protein or biologically active fragment is separated and/or recovered from a component of its natural environment. Isolated polypeptides include those expressed heterologously in genetically engineered cells or expressed in vitro.

Contaminant components include materials that would typically interfere with diagnostic or therapeutic uses for the polypeptide. To be substantially isolated, preparations having less than 30% by dry weight of non-SHAAGtide contaminating material (contaminants), more preferably less than 20%, 10% and most preferably less than 5% contaminants.

Polypeptides and fragments of interest can be produced by any method well known in the art, such as by expression via vectors such as bacteria, viruses and eukaryotic cells. In addition, in vitro synthesis, such as peptide synthesis, may be also used.

An "active" polypeptide or polypeptide fragment retains a biological and/or an immunological activity similar, but not necessarily identical, to an activity of the SHAAGtide polypeptide shown in Tables 6 and 8. Immunological activity, in the context of this immediate discussion of the polypeptide per se, and not an actual biological role for SHAAGtide in eliciting or enhancing an immune response, refers to an aspect of a SHAAGtide polypeptide in that a specific antibody against a SHAAGtide antigenic epitope binds SHAAGtide. Biological activity refers to a function, either inhibitory or stimulatory, caused by a native SHAAGtide polypeptide. A biological activity of SHAAGtide polypeptide includes, for example, chemotaxis, inducing, enhancing or aiding an immune response. A particular biological assay (see Examples), with or without dose dependency, can be used to determine SHAAGtide activity. A nucleic acid fragment encoding a biologically-active portion of SHAAGtide can be prepared by isolating a polynucleotide sequence that encodes a polypeptide having a SHAAGtide biological activity, expressing the encoded portion of SHAAGtide (e.g., by recombinant expression in vitro) and assessing the activity of the encoded portion of SHAAGtide polypeptide.

In general, a SHAAGtide polypeptide variant that preserves SHAAGtide polypeptide-like function and includes any variant in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

"SHAAGtide polypeptide variant" means an active SHAAGtide polypeptide having at least: (1) about 70% amino acid sequence identity with a full-length SHAAGtide sequence or (2) any fragment of a full-length SHAAGtide sequence. For example, SHAAGtide variants include SHAAGtide polypeptides wherein one or more amino acid residues are added or deleted at the N— or C-terminus of the sequences of SEQ ID NOS:1, 3, 5, 6, 8, 11, and 16. A SHAAGtide polypeptide variant will have at least about 70% amino acid sequence identity, preferably at least about 71% amino acid sequence identity, more preferably at least about 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with SHAAGtide polypeptide sequence.

"Percent (%) amino acid sequence identity" is defined as the percentage of amino acid residues that are identical with amino acid residues in a SHAAGtide sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Publicly available computer software such as BLAST, BLAST2, ALIGN2 or Megalign (DNASTAR) can be used to align polypeptide sequences. Parameters for measuring alignment, including any algorithms needed to achieve maximal alignment over the full length of the sequences being compared, can be determined.

Chimeric and Fusion Polypeptides Fusion polypeptides are useful in expression studies, cell-localization, bioassays, SHAAGtide purification and importantly in adjuvant applications when the peptide may be fused to the antigen(s) of interest. A SHAAGtide "chimeric polypeptide" or "fusion polypeptide" comprises SHAAGtide fused to a non-SHAAGtide polypeptide. A non-SHAAGtide polypeptide is not substantially homologous to SHAAGtide (SEQ ID NOS:1, 3, 5, 6, 8,11, and 16). A SHAAGtide fusion polypeptide may include any portion to an entire SHAAGtide, including any number of biologically active portions. In some host cells, heterologous signal sequence fusions may ameliorate SHAAGtide expression and/or secretion.

Fusion partners can be used to adapt SHAAGtide therapeutically. SHAAGtide-Ig fusion polypeptides can be used as immunogens to produce anti-SHAAGtide Abs in a subject, to purify SHAAGtide ligands, and to screen for molecules that inhibit interactions of SHAAGtide with other molecules. Additionally, fusions with antigens of interest can be used to facilitate vaccination/immunication procedures.

Fusion polypeptides can be easily created using recombinant methods. A nucleic acid encoding SHAAGtide can be fused in-frame with a non-SHAAGtide encoding nucleic acid, e.g., antigen(s) with which to immunize, to the SHAAGtide $NH_2$- or COO-terminus, or internally. Fusion genes may also be synthesized by conventional techniques, including automated DNA synthesizers. PCR amplification using anchor primers that give rise to complementary overhangs between two consecutive gene fragments that can subsequently be annealed and reamplified to generate a chimeric gene sequence (Ausubel et al., 1987). Many vectors are commercially available that facilitate sub-cloning SHAAGtide in-frame to a fusion moiety.

Mimetics

Polypeptide mimetics of SHAAGtide may also be used. The terms "mimetic" and "peptidomimetic" refer to a synthetic chemical compound that has substantially the same structural and/or functional characteristics as a SHAAGtide polypeptide. Mimetics can be either entirely composed of synthetic, non-natural analogues of amino acids, or a chimeric molecule of partly natural peptide amino acids and partly non-natural analogs of amino acids. Mimetics can also incorporate any amount of natural amino acid conservative substitutions. Polypeptide mimetic compositions can contain any combination of nonnatural structural components, which are typically from three structural groups: (a) residue linkage groups other than the natural amide bond ("peptide bond") linkages; (b) non-natural residues in place of naturally occurring amino acid residues; or (c) residues which induce secondary structural mimicry, i.e., inducing or stabilizing a secondary structure, e.g., a β turn, γ turn, β sheet, a helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (Spatola (1983) in *Chemistry and Biochemistry of Amino Acids, Peptides and Proteins*, Vol. 7, pp 267-357, "Peptide Backbone Modifications," Marcell Dekker, NY).

A polypeptide can also be characterized as a mimetic by containing all or some non-natural residues in place of naturally occurring amino acid residues. Nonnatural residues, as well as appropriate substitutions for each class of amino acids (Table B), are well known. For example, mimetics of aromatic amino acids can be generated by replacing by, e.g., D- or L-naphylalanine; D- or L-phenylglycine; D- or L-2 thieneylalanine; D- or L-1, -2, 3- or 4-pyreneylalanine, etc.

Other mimetics include those generated by hydroxylation of proline and lysine; phosphorylation of the hydroxyl groups of seryl or threonyl residues; methylation of the α-amino groups of lysine, arginine and histidine; acetylation of the N-terminal amine; methylation of main chain amide residues or substitution with N-methyl amino acids; or amidation of C-terminal carboxyl groups. A component of a natural polypeptide can also be replaced by an amino acid or peptidomimetic residue of the opposite chirality.

Mimetics also include compositions that contain a structural mimetic residue, particularly a residue that induces or mimics secondary structures, such as a β turn, β sheet, a helix structures, γ turns, and the like. For example, substitution of natural amino acid residues with D-amino acids; N-α-methyl amino acids; C-α-methyl amino acids; or dehydroamino acids within a peptide can induce or stabilize β turns, γ turns, β sheets or a helix conformations.

Cyclic Peptides

In some cases, cyclic SHAAGtide peptides may be advantageous. To make a SHAAGtide cyclic, cysteine residues included in a peptide can be oxidized to form —S—S-dimers or larger multimer (trimers, etc.) by oxidization. Two cysteines placed distal to each other in a peptide can be oxidized to prepare a cyclic peptide containing one or more functional amino acid sequences.

Practising the Invention

Assays Demonstrating SHAAGtide Activity (a) In vitro Assays

SHAAGtides have certain properties when used as an adjuvant; namely, enhancing, eliciting or modulating an immune response. Other activities of the SHAAGtides are known, including inducing chemotaxis on certain cells, including those expressing the formyl-peptide receptor-like-1 (FPRL1) receptor. In vitro chemotaxis (cell migration) assays can be used to identify SHAAGtide chemotactic properties. Such assays physically separate the cells from the candidate chemoattractant using a porous membrane and assaying the cell migration from one side of the membrane to the other, indicating cell migration. As an example, a conventional cell migration assay, such as the ChemoTx® system (Neuro-Probe, Rockville, Md.; (Goodwin, U.S. Pat. No. 5,284,753, 1994)) or any other suitable device or system (Bacon et al., 1988; Penfold et al., 1999) may be used. Cells expressing the target receptor are gathered. A candidate compound, such as SHAAGtide peptides or other chemokine/chemokine-like compound is prepared, usually in a concentration series by serial dilution in a buffer. The concentration range is typically between 0.1 nM and 10 mM, but will vary with the compound being tested.

To start the cell migration assay, solutions of the various candidate compound concentrations are added to the lower chamber of a cell migration apparatus, and the cell suspension is placed into the upper chamber that is separated by a porous membrane (about 3 µm to about 5 µm, depending on cell type(s) and cell size(s)). The cells are incubated under culture conditions (about 37° C. for human cells) for 60 to 180 minutes in a humidified tissue culture incubator. The incubation period depends on the cell type and if necessary, can be determined empirically.

After terminating the assay, non-migrating cells on the upper chamber of the apparatus are removed using a rubber scraper or other manual method, enzymatically or chemically, e.g., EDTA and EGTA solutions. The membrane that separates the two chambers is then removed from the apparatus and rinsed with Dulbecco's phosphate buffered saline (DPBS) or water. The number of cells that migrated into the lower chamber is then determined. Cell migration at levels above background (without a chemotactic or candidate compound), indicate that the candidate compound is chemotactic for the tested cells.

A candidate compound is considered chemotactic for a particular cell type if, at a concentration of about 1 pM to about 1 μm (e.g., between about 1 nM and 500 nM, e.g., 1 nM, about 10 nM, about 100 nM, or between about 1 pg/ml and about 10 μg/ml, e.g., between about 1 ng/ml and 1 μg/ml, e.g., about 10 ng/ml, about 100 ng/ml or about 1 μg/ml) attracts the cell at least 2-fold to 8-fold or more than a negative control.

(b) In vivo Assays

Chemotactic properties of a compound can be determined in animals, e.g., mammals such as non-human primates and mice. In one in vivo assay, the candidate compound (e.g., 2-20 μg in PBS) is administered by intradermal injection. After about 24 to about 96 hours or more, the presence or absence of cell infiltration is determined, using routine histological techniques. If an infiltrate is present, the cells are identified by type (mononuclear, neutrophil, dendritic, etc.) and are quantified.

Therapeutic Applications of SHAAGtide
SHAAGtide Compositions

SHAAGtide polypeptides (SEQ ID NOS:1, 3, 5, 6, 8, 11, and 16), or derivatives, analogs, etc. may be administered in compositions, such as those used to elicit, enhance or modulate an immune response; one or more of the SHAAGtide polypeptides (SEQ ID NOS: 1, 3, 5, 6, 8, 11, and 16) may be included. The compositions may include antigens of interest; however, SHAAGtide polypeptides may be administered by themselves. In some embodiments, the SHAAGtide polypeptides are administered in sequence with other administrations containing other molecules, such as polypeptide or polysaccharide immunogens.

In one aspect, the methods of the invention involve administration of an immunogen, in addition to a SHAAGtide composition. These compositions are administered at the same physical site in the subject. For example, the immunogen may be combined with a SHAAGtide composition, and the mixtures administered (e.g., injected) together. Alternatively, the composition and the antigen are administered separately to the same area of the subject (e.g., injected to the same site, applied topically to the same site, etc.). The different compositions are administered at different times.

SHAAGtide compositions can also be administered without an accompanying antigen (e.g., injection into a solid tumor to elicit an immune response to cancer cells, or injection in tissue surrounding a solid tumor, e.g., within 2 cm, of a solid tumor). Without intending to be bound by a particular mechanism, it is believed that SHAAGtides promote an immune reaction to the endogenous (e.g., tumor) antigen by recruiting APCs to the site of administration.

SHAAGtide compositions may additionally contain an excipient or carrier. SHAAGtide compositions may also include one or more immunogens (antigens; i.e., the antigen to which it is desired to induce, enhance or modulate an immune response).

SHAAGtide compositions may contain a conventional adjuvant. Conventional adjuvants typically convert soluble protein antigens into particulate material. Conventional adjuvants include Freund's incomplete, Freund's complete, Merck 65, AS-2, alum, aluminum phosphate, mineral gels such as aluminum hydroxide, and surface active substances such as lysolecithin, pluronic polyols, polyanions, peptides, oil emulsions, keyhole limpet hemocyanin, and dinitrophenol. Other useful adjuvants include, but are not limited to, bacterial capsular polysaccharides, dextran, IL-12, GM-CSF, CD40 ligand, IFN-γ, IL-1, IL-2, IL-3, IL4, IL-10, IL-13, IL-18 or any cytokine or bacterial DNA fragment.

Antigens

In one aspect, the present invention provides a method of eliciting or enhancing an immune response to an antigen, e.g., a predetermined or specified antigen. An antigen is a molecule that reacts with an antibody. In some embodiments the antigen is an immunogen. In some embodiments the antigen is linked to a protein carrier. For example, a SHAAGtide and an antigen may be physically linked, such as by a fusion protein, chemically cross-linking or complexes such as biotin and streptavidin.

An antigen (immunogen) is typically a peptide, a polypeptide, chemical compound, microbial pathogen, bacteria (e.g., live, attenuated, or inactivated), a virus (including inactivated virus particles, modified live viral particles, and recombinant virus particles), a recombinant cell, glycoproteins, lipoproteins, glycopeptides, lipopeptides, toxoids, carbohydrates, tumor-specific antigens, and other immunogenic components of pathogens. Mixtures of two or more antigens may be used. The antigen may be purified. In some embodiments, the antigen may be associated (covalently or non-covalently) with a SHAAGtide polypeptide.

The invention is used to provide protection from exogenous foreign infectious pathogenic-agents prior to exposure. In addition, the invention can be used to provide therapeutic effects against exogenous foreign pathogens to which an individual has been exposed or to individual displaying symptoms of exposure. The invention can be used to treat cancers, including, but not limited to, melanomas, lung cancers, thyroid carcinomas, breast cancers, renal cell carcinomas, squamous cell carcinomas, brain tumors and skin cancers. For example, the antigen may be a tumor-associated antigen (tumor specific-antigen). Tumor antigens are molecules, especially cell surface proteins, which are differentially expressed in tumor cells relative to non-tumor tissues.

For prophylactic use, compositions containing SHAAGtides are administered (e.g., in conjunction with immunogens) to a subject. For therapeutic use, compositions containing the SHAAGtides are administered to a subject once a disease is detected, diagnosed or even treated, such as after surgical removal of a tumor.

Exemplary antigens or vaccine components of the invention include antigens derived from microbial pathogens such as bacteria [e.g., *Pertussis* (*Bordetella pertussis*, inactivated whole organism); *Cholera* (*Vibrio cholerae*, whole killed organism); *Meningitis* (*Neisseria meningitidis*, polysaccharide from organism); Lyme Disease (*Borrelia burgdorferi*, lipoprotein OspA); Haemophilus B (*Haemophilus influenza* B polysaccharide, Tetanus conjugate or OmpC); Pneumonia (*Streptococcs pneumoniae* capsular polysaccharide) Typhoid (*Salmonella typhi* polysaccharide vaccine, killed whole organism)], viruses including inactivated virus particles, modified live viral particles, and recombinant virus particles to Influenza virus; Hepatitis A; Hepatitis B; Hepatitis C; Measles; Rubella virus; Mumps; Rabies; Poliovirus; Japanese Encephalitis virus; Rotavirus; Varicella], Diphtheria (*Corynebacterium diphtheriae*) and Tetanus (*Clostridium tetani*).

Polynucleotide Chemotactic Compositions

The SHAAGtide, the antigen, or both may be delivered as polynucleotides, such that the polypeptides are generated in situ. In the case of naked polynucleotides, uptake by cells can be increased by coating the polynucleotide onto a carrier, e.g. biodegradable beads, which is efficiently transported into cells. In such vaccines, the polynucleotides may be present within any of a variety of delivery systems, including nucleic acid expression systems, bacterial and viral expression systems.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as SHAAGtide. In expression vectors, the introduced DNA is operably-linked to elements such as promoters that signal to the host cell to transcribe the inserted DNA. Inducible promoters that control gene transcription in response to specific factors can be exceptionally useful. Operably-linking a SHAAGtide and/or antigen polynucleotide to an inducible promoter can control the expression of a SHAAGtide and/or antigen polypeptide or fragments. Examples of classic inducible promoters include those that are responsive to α-interferon, heat shock, heavy metal ions, and steroids such as glucocorticoids (Kaufman, 1990), and tetracycline. Other desirable inducible promoters include those that are not endogenous to the cells in which the construct is being introduced, but are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences.

Administration of SHAAGtide and Immunogen (Antigen)

SHAAGtide compositions may contain one or more antigens or antigen-encoding polynucleotides. Antigens can be administered in combination with SHAAGtides (i.e., in the same mixture). Alternatively, they can be administered separately. In one aspect, the invention provides an immunization method in which a combination of one or more antigens (or antigen-encoding polynucleotides) and one or more SHAAGtides (or SHAAGtide-encoding polynucleotides) are administered to a subject. The antigen or SHAAGtide may be administered in a delivery vehicle such as a physiologically acceptable excipient.

The antigen may be administered simultaneously with the SHAAGtide composition or the antigen and the SHAAGtide composition is administered at different times, typically to the same site. For example, the chemotactic composition (without the antigen) can be administered between about 15 minutes and about 96 hours prior to the administration of the antigen, more often between about 15 minutes and about 48 hours, more often between 24 hours and 96 hours, often between about 48 hours and 72 hours or between 72 hours and 96 hours prior to the administration of the antigen.

When a SHAAGtide composition and an antigen composition are injected at the same site in a subject, preferably the injections are within 2 cm of each other, preferably within 1 cm or preferably within 0.5 cm of each other on the two dimensional surface of the body. The administrations should also be done to a similar depth and to the same tissue layers. For intramuscular injections, the depth should be more precisely monitored to achieve a three dimensional equivalent placement of the SHAAGtide and the antigen to within 2 cm of each other, preferably to within 1 cm, and more preferably to within 0.5 cm. The injection site can be marked with an indelible ink to assist the physician.

One dose (administration) of the composition may be given. However, the first administration may be followed by boosting doses. For example, the SHAAGtide composition is administered in multiple doses, often in combination with an antigen (e.g., by co-administration). The SHAAGtide composition (optionally including antigen) may be administered once, twice, three times, or more. The number of doses administered to a subject is dependent upon the antigen, the extent of the disease, and the response of a subject to the SHAAGtide composition. Within the scope of the present invention, a suitable number of doses includes any number required to immunize an animal to a predetermined antigen.

A second administration (booster) of the SHAAGtide composition and antigen may be given between about 7 days and 1 year after the first administration. The time between the first and second administrations may be 14 days to 6 months, 21 days and 3 months, often between about 28 days and 2 months after the original administration. A third administration (second booster) may be given between about 14 days and 10 years after the first administration, e.g., between about 14 days and 3 years, often between about 21 days and 1 year, very often between about 28 days and 6 months after the first administration. Subsequent boosters may be administered at 2 week intervals, or 1 month, 3 month or 6 month to 10 year intervals.

A variety of vaccine administration doses and schedules can be developed easily; the determination of an effective amount and number of doses of SHAAGtides of the invention, antigens, or some combination of SHAAGtides and antigens for administration is also well within the capabilities of those skilled in the art.

Effective Dose

Typically, the amount of SHAAGtide and antigen will be administered to a subject that is sufficient to immunize an animal against an antigen (i.e., an "immunologically effective dose" or a "therapeutically effective dose"). An amount adequate to accomplish an "immunologically effective dose" will depend in part on the SHAAGtide and antigen composition, the manner of administration, the stage and severity of the disease being treated, the weight and general state of health of the subject, and the judgment of the prescribing physician or other qualified personnel.

The effective dose of antigen and SHAAGtide can be formulated in animal models to achieve an induction of an immune response; such data can be used to readily optimize administration to humans based on animal data (see Examples). When the SHAAGtide is a polypeptide, a dose will typically be between about 1 fg and about 100 μg, often between about 1 μg and about 100 μg, more often between about 1 ng and about 50 μg, and usually between about 100 ng and about 50 μg. In some embodiments, the dose is between about 1 fg and about 100 μg per kg subject body weight, often between about 1 pg and about 100 μg, more often between about 1 ng and about 50 µg, and usually between about 100 ng and about 50 µg per kg subject body weight.

The amount of antigen will vary with the identity and characteristics of the antigen. A SHAAGtide composition may contain one or more antigens and one or more SHAAGtides at a molar or weight ratio of about 1:1000 or greater, SHAAGtide to antigen. Other useful ratios are between about 1:10 and 1:1000, between about 1:10 and 1:1000, or greater than 1:1000. The ratio of antigen to SHAAGtide in the composition may vary between about 1:10 and 10:1.

Carriers, Excipients, Conventional Adjuvants, Mode of Administration

The SHAAGtide-containing compositions of the invention may be administered in a variety of ways and in various forms. The SHAAGtide composition may include carriers and excipients, such as buffers, carbohydrates, mannitol, proteins, polypeptides or amino acids such as glycine, antioxidants, bacteriostats, chelating agents, suspending agents, thickening agents and/or preservatives; water, oils, saline solutions, aqueous dextrose and glycerol solutions, other pharmaceutically acceptable auxiliary substances as required to approximate physiological conditions, such as buffering agents, tonicity adjusting agents, wetting agents, etc. A conventional adjuvant may also be incorporated into the composition.

While any suitable carrier may be used to administer the compositions of the invention, the type of carrier will vary depending on the mode of administration. Compounds may also be encapsulated within liposomes. Biodegradable microspheres are convenient in some instances as carriers; for example, such as those described in (Tice et al., U.S. Pat. No. 5,942,252, 1999).

Sterilization of the compositions is desirable, such as that accomplished by conventional techniques or sterile filtering. The resulting aqueous solutions may be packaged for use as is, or lyophilized.

The SHAAGtide compositions of the invention may be administered in a variety of ways, including by injection (e.g., intradermal, subcutaneous, intramuscular, intraperitoneal etc.), by inhalation, by topical administration, by suppository, by using a transdermal patch or by mouth.

When administration is by injection, compositions may be formulated in aqueous solutions, preferably in physiologically compatible buffers such as Hanks solution, Ringer's solution, or physiological saline buffer. The solution may contain formulatory agents such as suspending, stabilizing and/or dispersing agents. Alternatively, the chemotactic composition may be in powder form for constitution with a suitable vehicle, e.g., sterile pyrogen-free water, before use. Inhalation-delivered compositions may be as aerosol sprays from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch. For topical administration, the compositions may be formulated as solutions, gels, ointments, creams, suspensions, and the like, as are well known in the art. In some embodiments, administration is by means of a transdermal patch. Suppository compositions may also be formulated to contain conventional suppository bases.

When administration is oral, a composition can be readily formulated by combining the composition with pharmaceutically acceptable carriers. Solid carriers include mannitol, lactose, magnesium stearate, etc.; such carriers enable the formation of tablets, pills, dragees, capsules, liquids, gels, syrups, slurries, suspensions etc., for oral ingestion. Such formulations may be powders, capsules and tablets; suitable excipients include fillers such as sugars, cellulose preparation, granulating agents, and binding agents.

Nucleic acid molecules, such as those encoding SHAAGtides, can be inserted into vectors and used as gene therapy vectors. Gene therapy techniques have recently become quite advanced and are meeting enviable success (Meikle, 2602). Gene therapy vectors can be delivered to a subject by, for example, intravenous injection, local administration (Nabel and Nabel, U.S. Pat. No. 5,328,470, 1994), or by stereotactic injection (Chen et al., 1994). The pharmaceutical preparation of a gene therapy vector can include an acceptable diluent or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Other convenient carriers include multivalent carriers, such as bacterial capsular polysaccharide, a dextran or a genetically engineered vector. In addition, sustained-release formulations include, for example, SHAAGtide molecules and/or antigens, allowing for the release of SHAAGtides and/or antigens over extended periods of time, such that without the sustained release formulation, the SHAAGtides and/or antigens would be cleared from a subject's system or degraded.

Vaccination for Monoclonal and Polyclonal Antibody Production

Methods of producing polyclonal and monoclonal antibodies, including binding fragments (e.g., $F_{(ab)2}$) and single chain versions are well known. However, many antigens are incapable of triggering an adequate antibody response. In one embodiment, a composition comprising a SHAAGtide of the invention and an antigen is administered to an animal, thus inducing or enhancing the immune response in the animal. Polyclonal or monoclonal antibodies are subsequently prepared by standard techniques.

Stimulation of Innate Immune Response

In another aspect, the compositions of the invention are administered to a subject to stimulate the innate immune response. The innate immune response is body's initial defense against pathogens and is elicited by a variety of cells including APCs. These cells express surface and cytoplasmic receptors that recognize molecules of foreign origin (e.g., bacterial and viral nucleic acids, proteins, carbohydrates). Upon detecting these signals, the dendritic cells and macrophage elicit a defensive response that includes the release of cytokines (including interferons, TNF-α, and IL-12) and chemokines that attract cells such as immature dendritic cells, macrophage, NK cells, and granulocytes, to the site of challenge.

The compositions of the invention can be used to attract dendritic cells and other cells to the site of administration, but also to stimulate these cells into eliciting elements of the innate immune response to confer non-specific protection while the body is generating the adaptive response. For example, a SHAAGtide composition is administered (without antigen) prior to or post exposure of an anticipated infection, including those that are sinisterly applied, such as in bioterrorism. In another embodiment, SHAAGtides are administered with "foreign" molecules (e.g., bacterial or viral nucleic acids, proteins, carbohydrates, or synthetic elements which mimic these elements).

Use of SHAAGtide Compositions in the Treatment of Disease

The invention provides for both prophylactic and therapeutic methods of treating a subject at risk of (or susceptible to) a disorder or having a disorder associated with aberrant FPRL1 receptor or FPRL1 ligand activity. Examples include neurodegenerative disorders, such as Alzheimer's Disease.

Diseases or conditions of humans or other species which can be treated with SHAAGtides or proteins or peptides comprising SHAAGtides, or inhibitors or agonists of FPLR1-SHAAGtide interactions, include, but are not limited to, peripheral—chronic inflammation-related diseases, for example: chronic inflammation; thrombosis; atherosclerosis; restenosis; chronic venous insufficiency; recurrent bacterial infections sepsis; cutaneous infections; renal disease; glomerulonephritis; fibrotic lung disease; allergic disease; IBS; rheumatorid arthritis and acute bronchiolitis. Central nervous system—macroglia and microglia related diseases, for example: neurodegenerative diseases; Alzheimer's disease; Multiple sclerosis; Parkinson's disease; neuroinflammation; HIV-associated neurological diseases; HIV-associated dementia; CNS bacterial infections; brain Toxoplasma gondii; Acanthamoeba infections; Listeria infections; prion diseases; subacute spongiform encephalopathies and macular degeneration may also be treated.

Diseases and disorders that are characterized by increased FPRL1 levels or biological activity may be treated with therapeutics that antagonize (i.e., reduce or inhibit) activity. Antagonists may be administered in a therapeutic or prophylactic manner. Therapeutics that may be used include: (1) molecules comprising inactive SHAAGtide peptides, or analogs, derivatives, fragments or homologs thereof; (2) SHAAGtide antisense nucleic acids (3) antibodies to SHAAGtide peptides, or analogs, derivatives, fragments or homologs thereof or (4) modulators (i.e., inhibitors and antagonists) that antagonize the activity of the FPRL1 receptor.

Diseases and disorders that are characterized by decreased FPRL1 levels or biological activity may be treated with therapeutics that increase (i.e., are agonists to) activity. Therapeutics that up regulate activity may be administered therapeutically or prophylactically. Therapeutics that may be used include peptides, or analogs, derivatives, fragments or homologs thereof; or an agonist that increases bioavailability. Therapeutics that may be used include: (1) molecules comprising SHAAGtide peptides, or analogs, derivatives, fragments or homologs thereof; (2) SHAAGtide nucleic acids; or (3) modulators that agonize the activity of the FPRL1 receptor.

The invention provides a method for preventing, in a subject, a disease or condition associated with an aberrant FPRL1 receptor expression or activity, by administering an agent that modulates a FPRL1 activity. Subjects at risk for a disease that is caused or contributed to by aberrant FPRL1 activity can be identified by, for example, any or a combination of diagnostic or prognostic assays. Administration of a prophylactic agent can occur prior to the manifestation of symptoms characteristic of the FPRL1 aberrancy, such that a disease or disorder is prevented or, alternatively, delayed in its progression. Depending on the type of FPRL1 aberrancy, for example, a FPRL1 agonist or FPRL1 antagonist can be used to treat the subject. The appropriate agent can be determined based on screening assays.

Another aspect of the invention pertains to methods of modulating FPRL1 activity for therapeutic purposes. Modulatory methods involve contacting a cell with an agent that modulates one or more of the activities of FPRL1 activity associated with the cell. An agent that modulates FPRL1 activity can be a nucleic acid or a protein, a naturally occurring cognate ligand of FPRL1, a peptide, a SHAAGtide peptidomimetic, or other small molecule. The agent may stimulate FPRL1 activity. The agent may inhibit a FPRL1 activity. Modulatory methods can be performed in vitro (e.g., by culturing the cell with the agent) or, alternatively, in vivo (e.g., by administering the agent to a subject). For example, the method may involve administering a SHAAGtide or nucleic acid molecule as therapy to compensate for reduced or aberrant FPRL1 or FPRL1 ligand expression or activity.

Stimulation of FPRL1 activity is desirable in situations in which FPRL1, or FPRL1 ligand is abnormally down-regulated and/or in which increased FPRL1, or FPRL1 ligand activity is likely to have a beneficial effect; for example, in treating an infection or in vaccination. Conversely, diminished FPRL1, or FPRL1 ligand activity is desired in conditions in which FPRL1, or FPRL1 ligand activity is abnormally up-regulated and/or in which decreased FPRL1, or FPRL1 ligand activity is likely to have a beneficial effect; for example, in treating chronic inflammation.

Suitable in vitro or in vivo assays can be performed to determine the effect of a specific therapeutic and whether its administration is indicated for treatment of the affected tissue.

In various specific embodiments, in vitro assays may be performed with representative cells of the type(s) involved in the patient's disorder, to determine if a given therapeutic exerts the desired effect upon the cell type(s). Modalities for use in therapy may be tested in suitable animal model systems including, but not limited to rats, mice, chicken, cows, monkeys, rabbits, dogs and the like, prior to testing in human subjects. Similarly, for in vivo testing, any of the animal model system known in the art may be used prior to administration to human subjects.

Diseases and conditions associated with inflammation and infection can be treated using the methods of the present invention. The disease or condition is one in which the actions of a FPRL1 ligand on a FPRL1 receptor is to be inhibited or promoted, in order to modulate the immune response.

The compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compositions of the invention are effective for use in humans.

Combined therapy to modulate FPLR1 or FPLR1 ligand activity and thereby prevent and treat infectious diseases or inflammatory disorders and diseases is illustrated by the combination of the compounds of this invention and other compounds which are known for such utilities.

For example, in the treatment or prevention of inflammation, the present compounds may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as TNFα, an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, epinephrine, naphazoline, xylometazoline, propylhexedrine, or levo-desoxy-ephedrine; an anti-itussive such as codeine, hydrocodone, caramiphen, carbetapentane, or dextramethorphan; a steroid; cyclosporin A; methotrexate; IL-10; a diuretic; and a sedating or non-sedating antihistamine.

Pharmaceutical Compositions

Agonists or antagonists of the FPRL1 receptor can be incorporated into pharmaceutical compositions. Such compositions typically comprise the agonists or antagonists and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (Gennaro (2000)). Preferred examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

A pharmaceutical composition of the agonist or antagonist is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, for example, parabens, chlorobutanol, phenol, ascorbic acid, and thimerosal, can contain microorganism contamination. Isotonic agents, for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the active compound in the required amount in an appropriate solvent with one or a combination of ingredients as required, followed by sterilization. Generally, dispersions are prepared by incorporating the active compound into a sterile vehicle that contains a basic dispersion medium, and the other required ingredients. Sterile powders for the preparation of sterile injectable solutions, methods of preparation include vacuum drying and freeze-drying that yield a powder containing the active ingredient and any desired ingredient from a sterile solutions.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

For administration by inhalation, the compounds are delivered as an aerosol spray from a nebulizer or a pressurized container that contains a suitable propellant, e.g., a gas such as carbon dioxide.

Systemic administration can also be transmucosal or transdermal, For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Polyethylene glycols, e.g., PEG, are also good carriers. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al. U.S. Pat. No. 4,522,811. 1985).

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound in association with the required pharmaceutical carrier. The specification for the unit dosage forms of the invention are dictated by, and directly dependent on, the unique characteristics of the active compound and the particular desired therapeutic effect, and the inherent limitations of compounding the active compound.

The nucleic acid molecules of SHAAGtide can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al. (1994)). The pharmaceutical preparation of a gene therapy vector can include an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

In one aspect, the SHAAGtide is delivered as DNA such that the polypeptides are generated in situ. In one embodiment, the DNA is "naked," as described, for example, in Ulmer et al. (1993) and reviewed by Cohen, (1993). The uptake of naked DNA may be increased by coating the DNA onto a carrier, e.g. biodegradable beads, which is efficiently transported into the cells. In such vaccines, the DNA may be present within any of a variety of delivery systems known to those of ordinary skill in the art, including nucleic acid expression systems, bacterial and viral expression systems.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as SHAAGtide. In expression vectors, the introduced DNA is operably-linked to elements such as promoters that signal to the host cell to transcribe the inserted DNA. Some promoters are exceptionally useful, such as inducible promoters that control gene transcription in response to specific factors. Operably-linking a SHAAGtide polynucleotide to an inducible promoter can control the expression of a SHAAGtide polypeptide or fragments. Examples of classic inducible promoters include those that are responsive to α-interferon, heat shock, heavy metal ions, and steroids such as glucocorticoids (Kaufman, 1990. Methods Enzymol 185: 487-511.) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences.

The pharmaceutical composition may further comprise other therapeutically active compounds as noted herein which are usually applied in the treatment of FPRL1-related conditions.

In the treatment or prevention of conditions which require FPRL1 modulation an appropriate dosage level of an agonist or antagonist will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Kits

In an aspect, the invention provides kits containing one or more of the following in a package or container: (1) a biologically active composition of the invention or an FPRL1 antagonist; (2) a pharmaceutically acceptable adjuvant or excipient; (3) a vehicle for administration, such as a syringe; (4) instructions for administration. Embodiments in which two or more of components (1)-(4) are found in the same container are also contemplated.

When a kit is supplied, the different components of the composition may be packaged in separate containers and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized SHAAGtide polypeptide or polynucleotide, or buffers that have been packaged under a neutral, non-reacting gas, such as nitrogen. Ampules may consist of any suitable Material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

In an aspect, the invention provides kits containing one or more of the following in a package or container: (1) a SHAAGtide composition of the invention; (2) a pharmaceutically acceptable adjuvant or excipient; (3) an antigen (e.g., a biologically pure antigen); (4) a vehicle for administration, such as a syringe; (5) instructions for administration.

When a kit is supplied, the different components of the composition may be packaged in separate containers and admixed immediately before use. Such packaging of the components separately may permit long-term storage without losing the activity.

The reagents included in the kits can be supplied in containers of any sort such that the life of the different components are preserved and are not adsorbed or altered by the materials of the container. For example, sealed glass ampules may contain lyophilized SHAAGtide polypeptides or polynucleotides, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

The following examples are given to illustrate the invention and are not meant to limit it in any way.

Screening and Detection Methods

SHAAGtides (and SHAAGtide nucleotides used to express SHAAGtides) can be used as reagents in methods to screen for compounds that modulate FPRL1 receptor activity. Such compounds may be useful in treating disorders characterized by insufficient or excessive production of FPRL1 receptor or FPRL1 receptor ligand, or production of FPRL1 receptor or FPRL1 receptor ligand forms that have aberrant activity compared to wild-type molecules. In general, such compounds may be used to modulate biological functions that involve FPRL1 receptor/FPRL1 receptor ligand.

The invention provides methods (screening assays) for identifying modalities, i.e., candidate or test compounds or agents (e.g., peptides, peptidomimetics, small molecules or other drugs), foods, combinations thereof, etc., that affect the FPRL1 receptor or FPRL1 receptor ligand. This may be a stimulatory or inhibitory effect. The invention also includes compounds identified in such screening assays.

Testing for compounds that increase or decrease FPRL1 receptor activity in response to or independent of a ligand is desirable. A compound may modulate FPRL1 receptor activity by increasing or decreasing the activity of FPRL1 receptor itself (agonists and antagonists).

Test compounds can be obtained using any of the numerous approaches in combinatorial library methods, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptides, while the other four approaches encompass peptide, non-peptide oligomer or small molecule libraries of compounds (Lam, 1997).

A "small molecule" refers to a composition that has a molecular weight of less than about 5 kD and more preferably less than about 4 kD, and most preferably less than 0.6 kD. Small molecules can be, nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention. Examples of methods for the synthesis of molecular libraries have been described (Carell et al., 1994a; Carell et al., 1994b; Cho et al., 1993; DeWitt et al., 1993; Gallop et al., 1994; Zuckermann et al., 1994).

Libraries of compounds may be presented in solution (Houghten et al., 1992) or on beads (Lam et al., 1991), on chips (Fodor et al., 1993), bacteria, spores (Ladner et al., U.S. Pat. No. 5,223,409, 1993), plasmids (Cull et al., 1992) or on phage (Cwirla et al., 1990; Devlin et al., 1990; Felici et al., 1991; Ladner et al., U.S. Pat. No. 5,223,409, 1993; Scott and Smith, 1990).

Many assays for screening candidate or test compounds that bind to or modulate the activity of the FPRL1 receptor are available. A cell-free assay comprises, for example, contacting the FPRL1 receptor or biologically-active fragment with a SHAAGtide compound that binds the FPRL1 receptor to form an assay mixture, contacting the assay mixture with a test compound, and determining the ability of the test compound to interact with the FPRL1 receptor, where determining the ability of the test compound to interact with the FPRL1 receptor comprises determining the ability of the FPRL1 receptor to preferentially bind to or modulate the activity of the test compound. Cell-based assays include, for example, the calcium flux assays, binding assays and cellular migation assays discussed in the examples.

Immobilizing either a molecule containing a SHAAGtide sequence or one of its partner molecules (such as FPRL1) can facilitate separation of complexed from uncomplexed forms of one or both of the proteins, as well as to accommodate high throughput assays. Binding of a test compound to a SHAAGtide molecule or a FPRL1 receptor molecule, or interaction of SHAAGtide molecule with a FPRL1 receptor molecule in the presence and absence of a candidate compound, can be accomplished in any vessel suitable for containing the reactants, such as microtiter plates, test tubes, and micro-centrifuge tubes. A fusion protein can be provided that adds a domain that allows one or both of the proteins to be bound to a matrix. For example, GST (glutathione S-transferase)-SHAAGtide fusion proteins or GST-target fusion proteins can be adsorbed onto glutathione sepharose beads (SIGMA Chemical, St. Louis, Mo.) or glutathione derivatized microtiter plates that are then combined with the test compound or the test compound and either the non-adsorbed FPRL1 receptor or SHAAGtide molecule, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of SHAAGtide binding or activity determined using standard techniques.

Other techniques for immobilizing proteins on matrices can also be used in screening assays. See, for example co-pending U.S. patent application Ser. No. 09/721, 902. Either a SHAAGtide molecule or a FPRL1 receptor molecule can be immobilized using biotin-avidin or biotin-streptavidin systems. Biotinylation can be accomplished using many reagents, such as biotin-NHS (N-hydroxy-succinimide; PIERCE Chemicals, Rockford, Ill.), and immobilized in wells of streptavidin-coated 96 well plates (PIERCE Chemical). Alternatively, antibodies or antibody fragments reactive with SHAAGtide molecules or FPRL1 receptor molecules but which do not interfere with binding of the SHAAGtide to the FPRL1 receptor molecule can be derivatized to the wells of the plate, and FPRL1 receptor molecule or SHAAGtide trapped in the wells by antibody conjugation. Methods for detecting such complexes, in addition to those described for the GST-immobilized complexes, include immunodetection of complexes using antibodies reactive with FPRL1 receptor molecules or SHAAGtide molecules, as well as enzyme-linked assays that rely on detecting an enzymatic activity associated with the FPRL1 receptor molecules or SHAAGtide molecules.

To demonstrate that the compounds are antagonists of the FPRL1 receptor, one can determine if they inhibit the activity of a SHAAGtide on the receptor. Preferably such compounds have the at least one of the following characteristics:

(1) potently inhibit binding of a SHAAGtide or a molecule comprising a SHAAGtide sequence to the FPRL1 receptor;

(2) significant inhibition of the $Ca^{2+}$ response of a SHAAGtide or a molecule comprising a SHAAGtide binding to FPRL1;

(3) limited non-specific $Ca^{2+}$ response; or (4) inhibition of chemotactic activity.

Standard in vitro binding assays may be employed to demonstrate the affinity of the compounds for the FPRL1 receptor (thereby inhibiting the activity of a SHAAGtide by competitive interaction with the receptor). See examples below. Preferably, the active compounds exhibit an $IC_{50}$ value of <10 µM, more preferably <5 µM, most preferably <1 µM.

Compounds that inhibit the activity of SHAAGtide affect intracellular $Ca^{2+}$ concentrations in SHAAGtide stimulated cells. Ligand binding to the FPRL1 receptor results in G-protein induced activation of phospholipase C, which leads to the conversion of phosphatidyl inositol phosphate into inositol phosphate and diacylglycerol. Inositol phosphate in turn binds to a receptor located at intracellular sites to release $Ca^{2+}$ into the cytoplasm. In addition to $Ca^{2+}$ concentration increases due to release from intracellular stores, binding of inositol phosphate to its receptor leads to an increased flux of extracellular calcium across the membrane and into the cell. Other G-protein signaling pathways may be involved.

Thus, the activation of the FPRL1 receptor by a SHAAGtide, and, subsequently, inhibition of the activation by the compounds of the invention can be determined by assaying for an increase in free intracellular $Ca^{2+}$ levels. Typically, this can be achieved by the use of calcium-sensitive fluorescent probes such as quin-2, fura-2 and indo-1. The affect of the active compounds to block the $Ca^{2+}$ response depends on the amount of active compound and chemokine present. Generally, when 10 nM of chemokine is present, 10 µM of active compound should produce 20 to 100% inhibition of the $Ca^{2+}$ response.

To determine whether the active compound produces a non-specific $Ca^{2+}$ response, cells bearing multiple receptors, including the receptor to which the active compound is targeted, are incubated with compound. Cells are then stimulated with a ligand to the target receptor and sequentially followed by stimulation with ligands to other receptors found on the sample cells. A comparable response of non-target receptors to ligand in the presence or absence of compound indicates that the active compound is specific for the target receptor.

To determine chemotaxis, any cell migration assay format may be used, such as the ChemoTx® system (NeuroProbe, Rockville, Md.) or any other suitable device or system (Bacon et al., 1988; Penfold et al., 1999). In brief, these cell migration assays work as follows. After harvesting and preparing the cells bearing the active target chemokine receptor, the cells are mixed with candidate antagonists. The mixture is placed into the upper chamber of the cell migration apparatus. To the lower chamber, a stimulatory concentration of chemokine ligand is added. The migration assay is then executed, terminated, and cell migration assessed.

The inventors have shown SHAAGtide activity on the FPRL1 receptor expressed on monocytes, neutrophils, Immature Dendritic Cells and Mature Dendritic Cells. Hence, such cells may be used in in vitro assay methods. Enriched or substantially purified cell populations can be used in in vitro chemotaxis assays. These cell populations can be prepared by a variety of methods known in the art depending on the specific cell-type desired. Typically, substantially purified cell populations are prepared by culture under specific conditions, by physical characteristics such as behavior in a density gradient, by sorting according to characteristic markers (e.g., by fluorescence activated cell sorting (FACS) using antibodies (preferably monoclonal antibodies) to cell-surface proteins, immunoprecipitation), or other methods.

Cells can be identified by histology (see, e.g., Luna, 1968), by immunological staining and similar methods (see, e.g., Harlow et al. 1998; Coligan et al., 1991. Methods for preparing substantially purified cell compositions for use in in vitro chemotaxis assays are briefly described infra and in the Examples. However, the invention does not require that any particular purification method be used, so long as the desired cells are obtained; many variations and alternative methods are known to those of skill in the art. Further, many other purification and detection methods, including methods suitable for cells not specifically listed herein, are known in the art or can be easily developed. Further, cloned cell lines derived from immune system tissues can be used in the chemotaxis assays described herein, if desired. General immunological, purification and cell culture methods are described in Coligan et al. (1991), including supplements through 1999. Unless otherwise specified, cells in culture are incubated at 37° C. in 5% $CO_2$.

Suitable methods for monocyte purification are found in Bender et al., 1996. (also see U.S. Pat. No. 5,994,126). Briefly, monocytes are isolated from PBMC by depleting T cells using immobilized antibodies against a pan T cell surface marker CD2. Conveniently, a commercially available source of CD2 antibodies attached to magnetic beads (Dynal; Lake Success, N.Y.) is used. PBMC isolated from a buffy coat (typically 35 mls containing 400×10⁶ PMBC) by conventional Ficoll gradient centrifugation methods are resuspended in MACS buffer (DPBS (HyClone; Logan, Utah) with 1% BSA (Sigma)) at $20\times10^6$ cells per ml. DPBS is Dulbecco's Phosphate Buffered Saline ($CaCl_2$ (0.1 g/l), KCl (0.2 g/l), $KH_2PO_4$ (0.2 g/l), $MgCl_2\text{-}6H_2O$ (0.1 g/l), NaCl (8.0 g/l), $Na_2HPO4$ (2.16 g/l)). An appropriate amount of immobilized CD2+ magnetic beads (typically 10 μl per $10^6$ cells) are added to the cells. The mixture is incubated for 15 minutes at 4° C. with gentle rotation. The magnetically tagged T cells are removed from the unlabeled cells on a magnetic cell sorter (Dynal) according to the manufacturer's protocols. The unlabeled cells contain primarily monocytes and B cells.

B cells in the above preparation are removed by taking advantage of differential adhesion properties. Briefly, PBMC depleted of T cells are allowed to adhere to the plastic of a T-175 tissue culture flask ($100\times10^6$ cells/flask; Costar; Acton, Mass.) for 3 hours at 37° C. Non-adherent cells (comprising largely B cells) are aspirated. To completely remove non-adherent cells, the flasks are rinsed 3 more times with DPBS. The resulting cells are largely enriched (i.e., >90%) for monocytes.

Monocytes can also be isolated by positive selection of CD14 antigen. Briefly, PBMC isolated from peripheral blood, such as a buffy coat, by standard Ficoll gradient centrifugation methods are resuspended in MACS buffer at $1\times10^6$ cells/ml. Immobilized antibodies against the CD14 surface antigen, such as CD14+ magnetic microbeads (Milteyni) are added (1 μl of beads per $1\times10^6$ cells) and the mixture is incubated at 4° C. for 15 minutes. Monocytes are separated from the other cell populations by passing the mixture through a positive selection column on a magnetic cell sorter (Miltenyi Biotech; Auburn, Calif.) according to manufacturers protocol. Monocytes that are retained on the column are eluted with MACS buffer after the column is removed from the MACS apparatus. Cells are then pelleted by centrifugation and resuspended in RMPI plus 10% FCS media at $10^6$ cells per ml. Monocytes isolated by this method are cultured essentially the same way as those isolated by the CD2+ depletion method.

Suitable methods for purification of dendritic cells, including separate mature and immature populations, are known in the art. Substantially purified dendritic cells (including subpopulations of mature or immature cells) can be prepared by selective in vitro culture conditions.

Dendritic cells are widely distributed in all tissues that have contact with potential pathogens (e.g., skin, gastrointestinal and respiratory tracts, and T cell-rich areas of the secondary lymphoid tissues). In the skin and upper respiratory tract they form a lattice of highly arborised cells (called Langerhans cells in the skin). After capturing antigen, dendritic cells in the peripheral tissues such as the skin and gut, traffic via the draining lymphatics to the T cell areas of lymph nodes where they present the internalized antigen. Immature dendritic cells function to take up and process antigens. During subsequent migration to the draining lymph node, the DC matures. The mature dendritic cells functions as the key APC to initiate immune responses by inducing the proliferation of pathogen specific cytotoxic and helper T cells.

Substantially pure populations of dendritic cells can be produced by in vitro culture, infra). In addition, there are marked changes in expression of chemokine receptors during dendritic cell maturation which can be used to identify cell stage (Campbell et al. 1998; Chan et al. 1999; Dieu et al. 1998; Kellermann et al. 1999). For example, immature dendritic cells express predominately CCR1, CCR5, and CXCR4. Upon maturation, these receptors, with the exception of CXCR4, are down regulated.

In culture, immature forms of dendritic cells undergo maturation thought to be analogous to the events during migration of dendritic cells from the point of antigen contact until to the secondary lymphoid tissues. Human or macaque dendritic cells of various developmental stages can be generated in culture, from CD14$^+$ blood progenitors using specific cytokines. A separate lineage of dendritic cells can be differentiated from CD34+ precursor cells from cord blood or bone marrow. In one embodiment of the invention, subpopulations of dendritic cells are generated for in vitro assays for identification of chemotactic compositions (i.e. to assess chemotaxin potency and selectivity against defined DC sub-types). Exemplary subpopulations of dendritic cells are: (1) immature peripheral blood monocyte derived cells; (2) mature peripheral blood monocyte derived cells, and (3) cells derived from CD34+ precursors. Subpopulations are isolated or produced by a variety of methods known in the art. For example, immature and mature dendritic cells from PBMCs are produced according to Bender et al. supra.

Briefly, PBMCs are depleted of T cells using immobilized antibodies against the cell surface marker CD2 (present on all T cells). Commercially available CD2+ dynabeads (Dynal) can be used according to manufacturer's protocol. The T-cell depleted mixture is separated into adherent versus non-adherent fractions by incubating the cells on tissue culture grade plastic for 3 hours at 37° C. Non-adherent cells are gently removed, and adherent cells (generally CD14$^+$ monocytes) are placed in culture media (e.g., RMPI+10% FCS) supplemented with 1000 U/mL each of GM-CSF and IL4 (R&D Systems, Minneapolis, Minn.) ("Day 1"). Between days 3-7 the cells begin to display a veiled morphology, and cytokines are replenished on days 2, 4, and 6, at which time the cells can be harvested as immature dendritic cells. In one embodiment, cells of this in vitro stage are isolated and used in the assay. Approximately $10\times10^6$ dendritic cells are typically obtained from $400\times10^6$ PBMCs.

Day 7 immature dendritic cells exhibit typical dendritic cell morphology, with elongated cell body and many processes. The size of the cells increase significantly compared to the precursor monocytes. Immature dendritic cells can be characterized phenotypically by monitoring their expression of cell surface markers.

Immature dendritic cells (generated from peripheral blood monocytes or from bone marrow derived CD34+ precursors) can be further activated and differentiated to become mature dendritic cells. Two methods are primarily used: MCM (macrophage conditioned medium) and double-stranded RNA-ploy (I:C) stimulation (Cella et al, 1999; Verdijk et al. 1999).

In the MCM method, day 6 immature dendritic cells are harvested by centrifugation and resuspended in at $10^6$ cells/ml in maturation medium (e.g., MCM diluted (up to 1:1 with RPMI containing 10% FCS). GM-CSF (1000 U/ml) and IL4 (1000 U/ml) are added. Cells are cultured for three more days, without further addition of GM-CSF (1000 U/ml) and IL4. Day 9 cells are used as mature dendritic cells.

In the poly (I:C) method, day 6 immature dendritic cells are harvested and resuspended in the standard culture medium (RPMI plus 10% FCS) supplemented with 20 μg/ml of poly (I:C) (Sigma), 1000 U/ml of GM-CSF and IL4. Cells are cultured for another three days without additional cytokines. Day 9 cells are used as mature dendritic cells.

Mature dendritic cells generated by these two different methods exhibit phenotypic and functional properties distinct from those of immature dendritic cells or the precursor monocytes. Mature dendritic cells from each preparation are thoroughly characterized by FACS to ensure that the desirable cell types are obtained.

Notably, generated mature dendritic cells express significantly higher level of MHC class II on the cell surface than immature cells. Expression of CD80, CD83 and CD86 are also up-regulated. Chemokine receptor expression also changes dramatically during the maturation process. For instance, CCR1, CCR5 are down-regulated sharply in mature cells, while CCR7 is up-regulated and appears on the cell surface within a few hours after addition of MCM. Functionally, mature dendritic cells are no longer capable of efficiently taking up antigen, but gain the ability to stimulate the proliferation of naive T cells and B cells. Mature dendritic cells also change their migratory behaviors; they no longer respond to ligands for CCR1, CCR2 and CCR5, such as MIP-1α, RANTES and MIP-1β. Instead, they respond to CCR7 ligands SLC and ELC.

MCM is prepared by as described by Romani et al. 1996, with minor modifications. Briefly, petri dishes (100 mm, Falcon) are coated with 5 ml of human Ig (10 mg/mL) for 30 min at 37° C. and washed with PBS 2-3 times immediately before use. $50 \times 10^6$ PBMC in 8 ml are layered onto human Ig-coated plates for 1-2 hours. Non-adherent cells are washed away and discarded. The adherent cells are incubated in fresh complete medium (RPMI+10% normal human serum) at 37° C., and the resulting media (MCM) is collected after 24 hours. The TNF-α concentration in the MCM is determined by the standard ELISA method (e.g., using a TNF-α ELISA kit (R&D Systems, Minneapolis, Minn.)). The final TNF-α level in MCM is adjusted to 50 U/ml by mixing an appropriate amount of MCM with RPMI/10% fetal calf serum.

Suitable methods for neutrophil purification are known in the art. According to one suitable method, whole fresh blood (WB) is diluted 1:1 with 3% dextran in a 50 ml centrifuge tube and allowed to sediment for 30-45 minutes at room temperature. Twenty-five ml of WB plus 25 ml dextran results in approximately 35 ml of supernatant after 30 minutes sedimentation. The supernatant is layered over 12-15 ml Ficoll and centrifuged at 400×g for 3040 minutes at 18-20° C. The plasma/platelet layer containing mononuclear cells and Ficoll-Paque are removed by aspiration. Neutrophils are found in the white layer above the erythrocyte (RBC) layer. (In some preparations, the neutrophil and erythrocyte layers are mixed. In these cases, RBCs are removed by hypotonic lysis: 12.5 ml of cold 0.2% NaCl is added to the neutrophils/RBC pellet while vortexing. 12.5 ml of cold 1.6% NaCl is immediately added while still vortexing. The cells are centrifuged at 60-100×g for 10 m and recovered. If necessary the lysis step is repeated). The resulting neutrophils are >95% pure (with the eosinophis as the primary remaining cells).

Prognostic Assays

The diagnostic methods described herein can furthermore be utilized to identify subjects having or at risk of developing a disease or disorder associated with aberrant FPRL1 receptor or FPRL1 ligand expression or activity. For example, the described assays can be used to identify a subject having or at risk of developing a disorder such as a neurodegenerative disorder. Typically, a test sample is obtained from a subject and FPRL1 receptor or FPRL1 ligand is detected or activity is assayed. For example, a test sample can be a biological fluid (e.g., serum), cell sample, or tissue.

Prognostic assays can be used to determine whether a subject can be administered a modality (e.g., an agonist, antagonist, peptidomimetic, protein, peptide, nucleic acid, small molecule, food, etc.) to treat a disease or disorder associated with aberrant FPRL1 receptor or FPRL1 ligand expression or activity. Such methods can be used to determine whether a subject can be effectively treated with an agent for a disorder. The invention provides methods for determining whether a subject can be effectively treated with an agent for a disorder associated with aberrant FPRL1 receptor or FPRL1 ligand expression or activity. In such an assay, a test sample is obtained and SHAAGtide or nucleic acid is detected (e.g., where the presence of SHAAGtide or nucleic acid is diagnostic for a subject that can be administered the agent to treat a disorder associated with aberrant FPRL1 receptor or FPRL1 ligand expression or activity).

The following examples are given to illustrate the invention and are not intended to be limiting.

EXAMPLES

Example 1

CKβ8-1(25-116), Like Other CKβ8 Variants, Stimulates Intracellular Calcium Flux in CCR1 Expressing Cells The human recombinant chemokines, leukotactin, three known CKβ8 variants CKβ8(1-99), CKβ8(25-99), CKβ8-1 (1-116) and a novel $NH_2$-terminal truncated form of CKβ8-1, CKβ8-1 (25-116) were obtained from R&D Systems (Minneapolis, Minn.). CKβ8-1(25-116) was compared with the other three variants for the ability to elicit an intracellular calcium mobilization in stable human CCR1 transfected HEK239 cells. Human HEK293-CCR1 cells were prepared using Fugena 6 (Roche, Ind.) following the manufacturer's protocol. The HEK-293 cell lines were maintained in DMEM with 10% FBS supplemented with 800 μg/ml G-418.

Stable expression of human chemokine receptor CCR1 in HEK293 cell was obtained as follows: full length cDNA encoding CCR1 was cloned by the polymerase chain reaction (PCR) from genomic DNA isolated from human peripheral blood cells. The PCR product was cloned into pcDNA3.1 (Invitrogen, Carlsbad, Calif.) using standard molecular cloning procedures and completely sequenced to confirm identity.

Two micrograms of the CCR1/pcDNA3.1 construct were used to transfect the HEK293 cells as follows. FuGENE: DNA complex was prepared by mixing 6.0 μl FuGENE 6 reagent (Roche Molecular Biochemicals, Calif.) and 2 μg CCR1/pcDNA3.1 in 100 ul of serum-free medium (Hyclone, Colo.). After incubating for 30 minutes at room temperature, the complex was added to a 60 mm culture plate containing $0.5-1 \times 10^6$ cells in 10 ml DMEM medium supplemented with 10% FBS (Hyclone, Colo.). After mixing, the cells were returned to the incubator to culture at 37° C. for two days. At 48 hours post-transfection, Genetinin (G418) (Mediatech, Herndon, Va.) was added at a final concentration of 800 ug/ml. The cells were then plated in 96-well plates at a concentration of 20,000 cells/well. After 2-3 weeks under G418 selection, stable geneticin-resistant CCR1 expressing cells were assessed for their ability to mobilize calcium in response to MIP-1α at a concentration of 1-500 nM.

$Ca^{2+}$ mobilization responses were performed using the intracellular ratiometric fluorescent dye, lndo-1. Cells were loaded with Indo-1/AM (3 μM; Molecular Probes, Eugene, Oreg.) in culture medium (45 min, 20° C., $10^7$ cells/ml). After dye loading, cells were washed once with 10 ml PBS) and resuspended at $10^6$ cell/ml in HBSS containing 1% FBS. Cytosolic $[Ca^{2+}]$ release was determined using excitation at 350 nm using a Photon Technology International fluorimeter (excitation at 350 nm, ratioed dual emission at 400 and 490 nm).

With HEKCCR1-293 transfectants, CKβ8-1(25-116) and the other CKβ8 variants induced a rapid calcium flux at 100 nM. The two truncated variants CKβ8(25-99) and CKβ8-1

(25-116) induced a high calcium response, while the signals generated by variants CKβ8(25-99) and CKβ8-1 (1-116) were lower. None of these chemokines induced a signal with the untransfected parental HEK293 cells, demonstrating that the activity is due to CCR1 and not an endogenous receptor. The maximal receptor stimulations obtained with 100 nM CKβ8(25-99) and CKβ8-1(25-116) were equivalent to those obtained with the same concentration of the CCR1 agonist, leukotactin.

Example 2

CCL23 Varant CKβ8-1(25-116) Displays an Unique Activity Profile in Human Monocyte and Neutrophils that is not a CCRI Linked Event The human recombinant chemokines, leukotactin, MIP-1α, three known CKβ8 variants CKβ8(1-99), CKβ8(25-99), CKβ8-1(1-116) and a novel NH$_2$-terminal truncated form of CKβ8-1, CKβ8-1 (25-116) were obtained from R&D Systems (Minneapolis, Minn.). Human monocytes were generated from buffy coats (Stanford Blood Center, Palo Alto, Calif.) following a standard protocol. Briefly, PBMC were isolated by standard density gradient centrifugation (Ficoll-Paque-Plus, Pharmacia). Monocytes were purified using CD14 Microbeads (Miltenyi, Auburn, Calif.) magnetic positive selection. Human neutrophils were isolated from fresh peripheral blood from healthy individuals by gradient centrifugation on Ficoll-Hypaque (Hyclone, Calif.).

The activity of the CCL23 variants was tested on freshly prepared human monocytes and neutrophils using the calcium flux test described in Example 1. Although all of the chemokines stimulated some calcium release on monocytes, CKβ8(1-99) and CKβ8-1(1-116) showed poor activity, even at 250 nM. CKβ8(25-99) showed slightly higher calcium stimulation. However, CKβ8-1(25-116) exhibited a unique calcium flux with extended calcium release. The maximal receptor stimulation obtained with 100 nM CKβ8-1(25-116) was at least two fold higher than that obtained with the same concentration of leukotactin.

On neutrophils, 100 nM leukotactin induced a calcium flux but neither MIP-1α nor CKβ8(1-99), CKβ8(25-99) or CKβ8 (1-116) induced a calcium flux. However, CKβ8-1(25-116) induced an unique calcium release. The magnitude was much higher than observed for the same amount of leukotactin stimulation.

Example 3

Cross-Desensitization Test Performed on HEK293-CCR1 Transfectants, Monocytes and Neutrophils In cross-desensitization tests tests, cells were stimulated sequentially with leukotactin and then the chemokines CKβ8 (1-99), CKβ8(25-99), CKβ8-1(1-116), and CKβ8-1(25-116). On HEK293-CCR1 transfectants (prepared as in Example 1), leukotactin induced similar patterns of receptor desensitization to all variants. When the cells were pretreated with 100 nM leukotactin, the calcium flux response to all ligands was completely inhibited.

Similar receptor cross-desensitization tests were performed using both monocytes and neutrophils (prepared as in Example 2). On monocytes, leukotactin completely desensitized the CCL23 variants, CKβ8(1-99), CKβ8(25-99), CKβ8-1 (1-116). In contrast, leukotactin prestimulation did not desensitize CKβ8-1(25-116) activity on monocytes. On neutrophils, CKβ8(1-99), CKβ8(25-99), and CKβ8-1(1-116) were inactive and prestimulation with leukotactin had no effect. However, leukotactin prestimulation did not desensitize the stimulation with CKβ8-1(25-116).

Example 4

CCL23 Variants Compete with $^{125}$I-MIP-1α for Binding to CCR1-Expressing Cells The binding characteristics of CCL23 variants was compared in human CCR1 expressing cells. The ability of MIP-1α and the CCL23 variants CKβ8(1-99), CKβ8(25-99), CKβ8-1(1-116) and CKβ8-1(25-116) to compete with $^{125}$I-MIP-1α binding was investigated in HEK293-CCR1 cells (prepared as in Example 1). The cells were incubated with $^{125}$I-labeled MIP-1α (final conc. ~0.05 nM) in the presence of unlabeled chemokine (3 hours at 4° C.: 25 mM HEPES, 140 mM NaCl, 1 mM CaCl$_2$, 5 mM MgCl$_2$ and 0.2% BSA, adjusted to pH 7.1). Reactions mixtures were aspirated onto PEI-treated GF/B glass filters using a cell harvester (Packard). The filters were washed twice (25 mM HEPES, 500 mM NaCl, 1 mM CaCl$_2$, 5 mM MgCl$_2$, adjusted to pH 7.1). Scintillant (MicroScint-10; 35 μl) was added to dried filters and the filiters counted in a Packard Topcount scintillation counter. Data were analyzed and plotted using Prism software (GraphPad Software, San Diego, Calif.).

Competition curves were observed with increasing concentrations of MIP-1α or CCL23 variants. MIP-1α gave an IC50 of 0.54 nM. The CCL23 variants gave IC50 values of 64 nM, 1.34 nM, 206 nM, and 112 nM, respectively. CKβ8-1(1-116) showed 3-4 fold less potency than CKβ8(1-99) on this transfectant for the displacement of the bound $^{125}$I-MIP-1α from CCR1, consistent with its relatively weak affinity for CCR1. Also as expected, the truncation of CKβ8(1-99), CKβ8(25-99), showed a 40-fold IC50 increase. However, the IC50 for CKβ8-1(25-116), the same amino acid truncated variant of CKβ8-1(1-116), is only increased one fold.

Simiar binding competition tests were conducted on monocytes and neutrophils. These cells were prepared as in Example 2. Binding competition between MIP-1α on neutrophils could not be studied, since MIP-1α does not bind neutrophils. On monocytes, MIP-1α has an IC50 of 0.27 nM, and CCL23 variants IC50s of 10 nM, 0.25 nM, 55 nM, and 5 nM, respectively. Overall, CKβ8(1-99) and CKβ8(25-99) showed similar IC50 to that observed on HEK293-CCR1 cells. However, CKβ8-1(1-116) and CKβ8-1(25-116) showed higher MIP-1α displacement activities on monocytes, especially CKβ8-1 (25-116) which was over 10 fold higher. $^{125}$I-MIP-1α binding-competition data (IC50) is shown in Table 12 The IC50 for each interaction was derived from non-linear least squares curve fitting.

TABLE 12

$^{125}$I-MIP-1α Binding Competition Data for HEK293-CCR1 Transfectants and Monocytes

|  | HEK293-CCR1 | Monocytes |
| --- | --- | --- |
| MIP1α | 0.54 nM | 0.27 nM |
| CKβ8(1-99) | 64 nM | 10.3 nM |
| CKβ8(25-99) | 1.34 nM | 0.25 nM |
| CKβ8-1(1-116) | 206 nM | 55 nM |
| CKβ8-1(25-116) | 112 nM | 5.1 nM |

Example 5

Variant CKβ8-1(25-116) Induces Human Monocyte and Neutrophil Migration with a Novel Migratory Property Migration assays were performed on monocytes and neutrophils. Human monocytes and neutrophils (prepared as in Exampe 2) were harvested and resuspended in chemotaxis medium (CM). The CM consisted of Hank's buffered salt solution (Gibco, Mass.) containing $CaCl_2$ (1 mM) and $MgSO_4$ (1 mM) with added 0.1% BSA (Sigma, St. Louis, Mo.). The assays were performed in 96-well ChemoTx® microplates (Neuroprobe, Mass.). Leukotactin, MIP-1α and chemokines (CKβ8(1-99), CKβ8(25-99), CKβ8-1(1-116) or CKβ8-1(25-116), prepared as in Example 1) were added to the lower wells (final volume 29 μL), and 20 μL of cell suspension ($5×10^6$ cells/mL for monocytes; $2.5×10^6$ cells/mL for neutrophils) added to the polycarbonate filters (5 μm pore size for monocytes; 3 μm pore size for neutrophils). After incubation for 90 min (37° C., 100% humidity, 5% $CO_2$), cells were removed from the upper surface of the filter by scraping. Cells that migrated into the lower chamber were quantified using the Quant cell proliferation assay kit (Molecular Probes, Oreg.).

On monocytes, CKβ8-1(25-99), CKβ8-1(1-99) and CKβ8-1(1-116) showed moderate activity at all concentrations up to 100 nM. CKβ8-1(25-116) showed a dramatically higher activity than the other three variants at 100 nM, although its activity at and 1 and 10 nM was very similar to the other variants.

The same test was performed on human neutrophils. Human neutrophils generally lacked robust response to CCR1 ligands. Consistent with the calcium flux results, none of the known CCR1 ligands including leukotactin and MIP-1α was active. However, CKβ8-1 (25-116) induced a robust response at 100 nM. This magnitude is comparable to many other potent CXCR1 and CXCR1 ligands including IL-8 and GRO-α.

Example 6

CKβ88-1(25-116) is able to Induce Intracellular Calcium Flux and Chemotaxis in Formyl Peptide Receptor Like 1 (FPRL 1) Expressing Cells The functional activities of CKβ8-1 (25-116) were investigated in human FPRL1-L1.2 transfectants and in native L1.2 cells. Stable expression of formyl peptide-like receptor 1 (FPRL1) in L.1.2 cell was obtained as follows. Full length cDNA encoding FPRL1 was cloned, using the polymerase chain reaction (PCR), from genomic DNA isolated from undifferentiated HL-60 cells. The polymerase chain reaction product was cloned into pcDNA3.1 (Invitrogen, Carlsbad, Calif.) using standard molecular cloning procedures and completely sequenced to confirm identity. Twenty micrograms of the FPRL1/pcDNA3.1 construct were linearized by digestion with Bsm1 (New England Biolabs, Beverly, Mass.) and used to transfect the murine B cell line L1.2 as follows. Twenty five million cells were washed twice and resuspended in 0.8 ml of PBS. The cells were incubated for 10 min at room temperature with the linearized FPRL/pcDNA3.1 construct DNA and transferred to a 0.4-cm cuvette, and a single electroporation pulse was applied at 250 V, 960 μF. Electroporated cells were incubated for 10 min at room temperature and transferred to culture at 37° C. in RPMI supplemented with 10% FCS. Geneticin (G418) was added to a final concentration of 800 μg/ml 48 h posttransfection and the cells plated into 96-well plates at 25,000 cells/well. After 2-3 weeks under drug selection, stable geneticin-resistant FPLR1 expressing cells were assessed for their ability to mobilize $Ca^{++}$ in response to SHAAGtide or CKbeta 8-1 at concentrations of 1 to 1000 nM.

A calcium flux test was performed on these transfectants using the method described in Example 1. Of the CCL23 variants, only CKβ8-1(25-116) stimulated calcium release in FPRL1 expressing cells. The synthetic peptides Trp-Lys-Tyr-Met-Val-D-Met-$NH_2$ (WKYMVm) and Trp-Lys-Tyr-Met-Val-Met-$NH_2$ (WKYMVM) ("W peptides 1 and 2") (obtained from Phoenix Pharmaceuticals (Belmont, Calif.)), known non-natural ligands for FPRL1, produced a robust calcium flux. A CKβ8-1(25-116) induced calcium release was not observed in pariental cells or cells transfected with other chemokine receptors. When a CKβ8-1(25-116) induced calcium flux dose response assay was performed, an EC50 of 10-20 nM was observed on these cells. CKβ8-1(1-116) showed no activity on FPRL1 expressing cells, even at 200 nM.

The ability of CKβ8-1 (25-116) to elicit the migration of the FPRL1 expressing cells was examined. Test conditions were as in Example 5. Although pariental L1.2 cells did not migrate in the assay, cells expressing FPRL1 migrated in a bell-shaped dose-dependent manner in response to CKβ8-1 (25-116) concentrations ranging from 1 nM to 1 βM. The half-maximal cell migration was observed at 30 nM. The magnitude of the maximal response was higher than observed with the synthetic peptides WKYMVm and WKYMVM. In general, compared to the other chemokines, CKβ8-1(25-116) showed a broader bell-shaped curve in FPRL1 mediated migration. Hence, in addition to its activity on CCR1, CKβ8-1(25-116) also functions through the receptor FPRL1 expressed on monocytes and neutrophils.

Example 7

CKβ8-1(25-116) is able to Displace $^{125}$I-labeled WKYMVm Binding on Human Monocytes and FPRL 1 Expressing Cells The binding of CKβ8-1 (25-116) to FPRL1 was determined by measuring the ability of CKβ8-1(25-116) to displace $^{125}$I-labeled WKYMVm ($^{125}$I-labeled Trp-Lys-Tyr-Met-Val-D-Met-$NH_2$, Perkin Elmer Life Science (Boston, Mass.)) from human FPRL1-L1.2 transfectants and human monocytes. Cells were incubated with 0.01 nM $^{125}$I-WKYMVm in the presence of increasing concentrations of unlabeled WKYMVm or CKβ8-1(25-116) for three hours at 4 degree C. The IC50 for each interaction was derived from non-linear least squares curve fitting of the data by using Prism software (GraphPad Software).

For FPRL1-L1.2 transfectants and monocytes, competition curves were observed with increasing concentrations of WKYMVm or CKβ8-1 (25-116) (Table 13). Such curves were not observed for other CCL23 variants.

TABLE 13

| $^{125}$I-labeled WKYMVm competition curves observed with WKYMVm and CKβ8-1(25-116). | | |
|---|---|---|
| | IC50 | |
| | Human Monocytes | L1.2 FPRL1 Cells |
| WKYMVM | 1.5 nM | 80 nM |
| CKβ8-1(25-116) | 31 nM | 196 nM |

Example 8

Chemokine or SHAAGtide Induced Calcium Mobilization by Immature Dendritic Cells, Mature Dendritic Cells, Monocytes or Neutrophils Human recombinant CKβ8-1(25-116) chemokine was obtained from R&D Systems (Minneapolis, Minn.). The peptide SHAAGtides SEQ ID NO:1 and SEQ ID NO:6 and a control protein (the reverse sequence of SEQ ID NO:1) were synthesized and HPLC-purified using routine techniques as described in Sambrook et al., 1989, and Ausubel et al., 1999.

Human monocytes were either generated from buffy coats (Stanford Blood Center, Palo Also, Calif.) or from fresh blood of healthy individuals following a standard protocol. Briefly, PBMC were isolated by a Ficoll-Paque gradient centrifugation (Ficoll-Paque-Plus, Pharmacia). Monocytes were purified by CD14 Microbeads (Miltenyi) magnetic positive selection. Human neutrophils were isolated from fresh blood by dextran sedimentation and gradient centrifugation Ficoll-Paque gradient centrifugation. All cells were washed and resuspended ($1 \times 10^7$/ml) in RPMI medium with 10% FBS.

Immature DCs were derived by culturing CD14+ monocytes in the presence of GM-CSF and IL4. Briefly, monocytes were cultured in a T-175 flask at $10^6$ cells/ml in RPMI/10% FCS. Recombinant human GM-CSF and IL4 were added on day 0, 2, 4 and 6 to a final concentration of 1000 u/ml and 500 u/ml, respectively. Cells were harvested on day 7 as immature DCs and characterized for surface protein expression by FACS analysis. DC maturation was carried out by culturing day 6 immature DCs in macrophage-conditioned medium (MCM). Briefly, day 6 immature DCs were harvested by centrifugation and resuspended in MCM at $10^6$ cells/ml. The medium was supplemented with 1000 u/ml of GM-CSF and 500 u/ml IL4. After three more days of culture, cells were harvested as mature DCs and characterized by surface protein expression flow cytometry.

MCM was prepared as follows: PBMCs isolated from buffy coat were incubated at 37° C. in a plastic flask pre-coated with 10 mg/ml human IgG (Sigma, St Louis, Mo.) for 30 minutes. After 30 minutes, non-adherent cells were removed and adherent cells were washed three times with DPBS, then cultured in RPMI/10% human serum. Conditioned-medium was collected after 24 hours. TNF-α concentration, which is critical for DC maturation, was determined by using a TNF-α ELISA kit (R&D Systems, Minn.). The final TNF-α level in MCM was adjusted to 50 u/mi by mixing with RPMI/10% human serum, and was stored at −80 freezer until use.

$Ca^{2+}$ mobilization responses were performed using an intracellular ratiometric fluorescent dye, Indo-1. Cells were loaded with Indo-1/AM (3 μM; Molecular Probes (Eugene, Oreg.)) in culture medium (45 min, 20° C., $10^7$ cells/mi). After dye loading, cells were washed once (10 ml PBS) and resuspended at $10^6$ cell/ml in HBSS containing 1% FBS. Cytosolic $[Ca^{2+}]$ release was determined using excitation at 350 nm using a Photon Technology International fluorimeter (excitation at 350 nm, ratioed dual emission at 400 and 490 nm).

The SHAAGtides SEQ ID NO:1 and SEQ ID NO:6, as well as CKβ8-1 (25-116), produced a robust calcium flux on human monocytes and neutrophils and were partially active on immature Dendritic Cells and mature Dendritic Cells. No significant calcium flux was observed with the control peptide. Since immature Dendritic Cells express high levels of CCR1, CKβ8-1(25-116) induces $Ca^{2+}$ release in these cells.

Example 9

Chemokine, SHAAGtide, and SHAAGtide Truncated Variants Induced Calcium Mobilization by Stable Expressed FPRL 1 Cells Stable expression of human FPRL1 in L1.2 cells was obtained as in Example 6. Calcium flux tests were conducted on the transfectants using the method described in Example 1. Chemokines (CKβ8(1-99), CKβ8(25-99), CKβ8-1(1-116) and CKβ8-1(25-116), were prepared as in Example 1. W peptides 1 and 2 were obtained as in Example 6. In addition, and the following SHAAGtide sequences and truncated variants (prepared as in Example 8) were tested:

| CCXP1 | SEQ ID NO: 1 |
| CCXP2 | SEQ ID NO: 2 |
| CCXP3 | SEQ ID NO: 3 |
| CCXP4 | SEQ ID NO: 4 |
| CCXP5 | SEQ ID NO: 5 |
| CCXP6 | SEQ ID NO: 6 |
| CCXP7 | SEQ ID NO: 7 |
| CCXP8 | SEQ ID NO: 8 |
| CCXP9 | SEQ ID NO: 9 |
| CCXP10 | SEQ ID NO: 10 |

All ligands were added in a dose response manner and the peak calcium flux response determined. Table 14 shows that CKβ8(25-116) (SEQ ID NO:16) and certain SHAAGtides induced calcium mobilization in FPRL1 transfectants. However, CKβ8(1-116), which does not contain a free SHAAGtide N-terminal, did not give significant mobilization. The data also indicates that the N-terminal of the SHAAGtide is important for its activity in FPRL1 transfactants. Those SHAAGtides having a truncated N-terminal gave greatly reduced calcium mobilization. SHAAGtides having a truncated or substituted C-terminal did not exhibit the same loss in activity as was observed after truncation of the N-terminal.

TABLE 14

Induction of Calcium Flux in FPRL1 L1.2 Cells. (IC50—were no IC50 value is listed, the sequence showed low or no significant activity.)

| | IC 50 |
|---|---|
| SEQ ID NO: 1 | 150 nM |
| SEQ ID NO: 2 | >50 μM |
| SEQ ID NO: 3 | 68 nM |
| SEQ ID NO: 4 | — |
| SEQ ID NO: 5 | 7.4 nM |
| SEQ ID NO: 6 | 38 nM |
| SEQ ID NO: 7 | — |
| SEQ ID NO: 8 | 45 nM |
| SEQ ID NO: 9 | — |
| SEQ ID NO: 10 | — |
| SEQ ID NO: 13 - CKβ8(1-99) | — |
| SEQ ID NO: 14 - CKβ8(25-99) | — |
| SEQ ID NO: 15 CKβ8(1-116) | — |
| SEQ ID NO: 16 CKβ8(25-116) | 11 nM |
| W peptide 1 | 0.7 nM |
| W peptide 2 | <0.1 uM |

Example 10

Chemotactic Activity of Chemokines, SHAAGtide and SHAAGtide Truncated Variants on FPRL1-L1.2 Cells The chemotactic activity of chemokines (CKβ8(1-99) and CKβ8(25-99)), SHAAGtides (SEQ ID NO:1 and SEQ ID NO:2) and W peptides 1 and 2 (obtained as in Example 6) on FPRL1-L1.2 cells was determined in migration assays. The chemokines were prepared as in Example 1. The SHAAGtide sequences SEQ ID NO:1 and SEQ ID NO:2 were prepared as in Example 8. FPRL1-L1.2 cells were prepared as in Example 6.

The migration assays were performed in 96-well ChemoTx® microplates (Neuroprobe) using the protocol described in Example 5. Both SEQ ID NO:1 and CKβ8-1(25-116) migrated the transfectants, indicating that they are functional for this receptor.

Example 11

Chemotactic Activity of Chemokines, SHAAGtide and SHAAGtide Truncated Variants on Human Monocytes and Neutrophils The chemotactic activity on human monocytes and neutrophils of chemokines: CKβ8(1-99), CKβ8(25-99), CKβ8(1-116) and CKβ8(25-116); W peptides 1 and 2 and the SHAAGtide sequences SEQ ID NO:1 and SEQ ID NO:2 was determined in migration assays. The above peptides were prepared as in previous examples. The migration assays were performed in 96-well CHEMOTX® microplates (Neuroprobe) using the protocol described in Example 5. Both SHAAGtide SEQ ID NO:1 and CKβ8-1(25-116) produced migration of both neutrophils and monocytes.

Example 12

Methods

Unless stated otherwise, reagents were obtained from Sigma Chemical Co. (St. Louis, Mo.).

SHAAYtide (SEQ ID NO:6) Peptide Preparation

The peptide of SEQ ID NO:6, "SHAAYtide", was chemically synthesized and purified (Phoenix Pharmaceuticals; Belmont, Calif.). The material was suspended in phosphate-buffered saline (PBS) at a concentration of approximately 1 mg/ml and stored at −20° C.

Enzyme-Linked Immunosorbent Assays (ELISAs)

First, 96-well U-bottom plastic dishes were coated overnight with 1 μg ovalbumin (OVA) in 100 μl PBS per well. The next day, the dishes were rinsed with PBS, blocked with PBS containing 5% fetal bovine serum (FBS), and rinsed with PBS again. Plasma samples from experimental animals (see below) were diluted $10^2$- to $10^5$-fold and added to the dishes for 2 hours, after which the dishes were again rinsed with PBS. The dishes were then incubated with biotinylated goat anti-monkey IgG detection antibodies, then rinsed with PBS and incubated with streptavidin-linked horseradish peroxidase (SA-HRP). After a final rinsing with PBS, the HRP substrate 2,2'-Azinobis [3-ethylbenzothiazoline-6-sulfonic acid]-diammonium salt was added. Color development was measured with an ELISA plate reader at 405 nm, and optical density (OD) units were converted to arbitrary "antibody units," where a unit is defined as the inverse of the plasma dilution that produces 50% of the maximum response from a standard curve obtained by serial dilution of an ascites collected from OVA-injected mice and containing OVA-specific antibodies.

Dendritic cell purification Substantially purified dendritic cells (including subpopulations of mature or immature cells) can be prepared. Subpopulations of dendritic cells include: (1) immature peripheral blood monocyte derived cells, (2) mature peripheral blood monocyte derived cells, and (3) cells derived from CD34-expressing precursors.

Human or macaque dendritic cells of various developmental stages can be generated in culture from CD14-expressing blood progenitors using specific cytokines. A separate lineage of dendritic cells can be differentiated from CD34-expressing precursor cells from cord blood or bone marrow. Finally, immature and mature dendritic cells from peripheral blood mononuclear cells (PMBCs) can also be produced (Bender et al., 1996). Mature dendritic cells can be made using macrophage conditioned medium and double stranded RNA-ploy (I:C) stimulation (Celia et al., 1999; Romani et al., 1996; Verdijk et al., 1999).

To confirm that a population of dendritic cells has been isolated, marked changes in chemokine receptor expression during dendritic cell maturation can be used to identify and confirm cell stage (Campbell et al., 1998; Chan et al., 1999; Dieu et al., 1998; Kellermann et al., 1999). For example, produced mature dendritic cells can be characterized by using cellular markers and fluorescence-activated cell sorting (FACS). Generated dendritic cells express higher levels of MHC class II on the cell surface than immature dendritic cells. Expression of CD80, CD83 and CD86 are also up-regulated. Chemokine receptor expression also changes dramatically during maturation; e.g., CCR1 and CCR5 are down-regulated in mature cells while CCR7 is up-regulated. Functional characteristics may also be exploited to confirm a cell type. For example, mature dendritic cells are incapable of taking up antigen efficiently, but gain the ability to stimulate the proliferation of naive T cells and B cells. Mature dendritic cells also change their migratory behaviors, being unresponsive to CCR1, CCR2 and CCR5 ligands while being newly responsive to CCR7 ligands.

Example 13

SHAAGtide Variant (SEQ ID NO:3) Attracts Dendritic Cells

This example describes an in vivo assay in which the ability of several chemokines and SHAAYtide (SEQ ID NO:6) to attract dendritic cells was demonstrated.

The following chemokines were obtained from R&D Systems (Minneapolis, Minn.): vMCK-2, mC10, and GM-CSF. The following peptides were synthesized at Phoenix Pharmaceuticals (San Carlos, Calif.): SHAAYtide (SEQ ID NO:6), several STRUCTURALLY MODIFIED peptides of SHAAGtide variant (SEQ ID NO:) (i.e. cyclized using the MPR-Cys linked cyclization), control peptide (SEQ ID NO:33, Gly Ala Ala His Ser Leu Thr Met Gin Pro Gly Ile Lys Arg Arg Trp Leu Met), randomly conjugated to OVA in either a 1:1 or 1:4 ratio (by MBS coupling method), and conjugated to OVA at the C-terminus (C-term, made by the addition of a cysteine), and SHAAGtide variant (SEQ ID NO:3). In three separate experiments, chemokines or peptides (2 μg or 20 μg in PBS) were injected intradermally into BALB/c or C57BI/6 mice (Jackson Laboratory; Bar Harbor, Me.). In each experiment, one mouse received an injection of PBS only as a negative control. At various times after injection, the mice were euthanized, and the area around the injection site was excised and subjected to immunohistology. Frozen sections were stained with anti-DEC-205 antibody (Bio-Whittaker Molecular Applications; Rockland, Me.) that recognizes a dendritic cell-specific molecule (Kraal et al., 1986). A relative staining number on a scale of 0 to 5 was assigned to each section (0, none; 1, slight; 2, mild; 3, moderate; 4, severe). Results are shown in Tables 15, 16, and 17.

As shown in Tables 15, 16, and 17, vMCK-2, C10, GM-CSF, SHAAYtide (SEQ ID NO:6), and all administered versions of SHAAGtide, showed excellent infiltration of DEC-205-labeled cells.

TABLE 15

Dendritic cell infiltration in C57Bl/6 mice (2 µg dose)

| Polypeptide | Time (hours) | Score | Polypeptide | Time (hours) | Score |
|---|---|---|---|---|---|
| saline | 6 | 0 | mC10 | 6 | 1 |
|  |  | 1 |  |  | 1 |
|  | 30 | 0 |  |  | 2 |
|  |  | 0 |  | 30 | 1 |
|  | 51 | 1 |  |  | 2 |
|  |  | 0 |  |  | 2 |
| vMCK-2 | 6 | 3 |  | 51 | 0 |
|  |  | 3 |  |  | 0 |
|  |  | 2 |  |  | 0 |
|  | 30 | 3 | SHAAYtide (SEQ ID NO: 6) | 6 | 1 |
|  |  | 1 |  |  | 1 |
|  |  | 3 |  |  | 1 |
|  | 51 | 0 |  | 30 | 0 |
|  |  | 3 |  |  | 0 |
|  |  | 3 |  |  | 0 |
|  |  |  |  | 51 | 0 |
|  |  |  |  |  | 0 |
|  |  |  |  |  | 0 |
|  |  |  |  |  | 0 |

TABLE 16

Dendritic cell infiltration in BALBc mice (various doses)

| Polypeptide | Dose | Time (hours) | Score | Polypeptide | Dose | Time (hours) | Score |
|---|---|---|---|---|---|---|---|
| saline | 0 µg | 6 | 0 | mC10 | 2 µg | 6 | 2 |
|  |  |  | 1 |  |  |  | 2 |
|  |  |  | 0 |  |  |  | 2 |
|  |  | 30 | 2 |  |  | 30 | 2 |
|  |  |  | 1 |  |  |  | 2 |
|  |  |  | 2 |  |  |  | 3 |
| vMCK-2 | 2 µg | 6 | 2 |  | 20 µg | 6 | 2 |
|  |  |  | 2 |  |  |  | 2 |
|  |  |  | 2 |  |  |  | 2 |
|  |  | 30 | 3 |  |  | 30 | 3 |
|  |  |  | 2 |  |  |  | 1 |
|  |  |  | 2 |  |  |  | 1 |
|  | 20 µg | 6 | 2 | SHAAYtide (SEQ ID NO: 6) | 2 µg | 6 | 2 |
|  |  |  | 3 |  |  |  | 2 |
|  |  |  | 3 |  |  |  | 3 |
|  |  | 30 | 3 |  |  | 30 | 3 |
|  |  |  | 2 |  |  |  | 2 |
|  |  |  | 3 |  |  |  | 3 |
|  |  |  |  |  | 20 µG | 6 | 2 |
|  |  |  |  |  |  |  | 2 |
|  |  |  |  |  |  |  | 3 |
|  |  |  |  |  |  | 30 | 3 |
|  |  |  |  |  |  |  | 0 |
|  |  |  |  |  |  |  | 1 |

TABLE 17

Infiltration in BALB/c mice, various doses

| Polypeptide | Time (hours) | Score |
|---|---|---|
| saline | 6 | 1 |
|  |  | 2 |
|  |  | 1 |
| vMCK-2 | 6 | 3 |
|  |  | 0 |
|  |  | 2 |
| GM-CSF | 6 | 2 |
|  |  | 1 |
|  |  | 1 |
| saline | 30 | 1 |
|  |  | 1 |
|  |  | 1 |
| GM-CSF | 30 | 1 |
|  |  | 1 |
| SHAAGtide variant (SEQ ID NO: 3)-15mer | 30 | 3 |
|  |  | 2 |
|  |  | 1 |
| SHAAGtide (SEQ ID NO: 6) | 30 | 0 |
|  |  | 2 |
|  |  | 2 |
| SHAAYtide (SEQ ID NO: 6), cyclized | 30 | 1 |
|  |  | 2 |
|  |  | 2 |
| SHAAYtide (SEQ ID NO: 6) and OVA | 30 | 3 |
|  |  | 3 |
|  |  | 1 |
| OVA-SHAAYtide (SEQ ID NO: 6) C-term | 30 | 2 |
|  |  | 2 |
|  |  | 2 |
| OVA-SHAAYtide (SEQ ID NO: 6) 1:1 | 30 | 4 |
|  |  | 4 |
|  |  | 3 |
| OVA-SHAAYtide (SEQ ID NO: 4) 1:4 | 30 | 3 |
|  |  | 3 |
|  |  | 4 |

TABLE 17-continued

Infiltration in BALB/c mice, various doses

| Polypeptide | Time (hours) | Score |
|---|---|---|
| Control peptide (SEQ ID NO: 33) | 30 | 1 |
|  |  | 0 |
|  |  | 2 |

Example 14

SHAAYtide (SEQ ID NO:6) Administration to Rhesus Monkeys

Different amounts (8, 20, or 60 μg in 100 μl PBS) of different polypeptides (see Table 18) were injected intradermally in Rhesus macaques under anesthesia. Twenty-four and 48 hours later, 6 mm skin punch biopsies were taken using aseptic technique and then bisected. One portion of the biopsy was embedded in OCT compound, flash frozen in liquid nitrogen and stored at −70° C. The other portion was immersed in formalin and embedded in paraffin wax; subsequently, sections cut on a microtome were stained with hematoxylin and eosin and then microscopically examined for cell infiltration into the dermis (Table 18). As a negative control, monkeys were injected with PBS lacking any polypeptides.

Mononuclear cell infiltration was scored on a scale of 0 to 5:0, very mild perivascular mononuclear inflammatory infiltration throughout the dermis; 1, a mild perivascular mononuclear inflammatory infiltrate seen throughout the dermis; 2, a mild/moderate perivascular mononuclear inflammatory infiltrate seen throughout the dermis; 3, a moderate perivascular mononuclear inflammatory infiltrate seen throughout the dermis; 4, an extensive perivascular mononuclear inflammatory infiltrate seen throughout the dermis; 5, a florid perivascular mononuclear inflammatory infiltrate seen throughout the dermis. intermediate scores are indicates, e.g., "⅔" represents a score between 2 and 3.

As shown in Table 18, SHAAYtide (SEQ ID NO:6) at 20 μg caused a moderately strong infiltration in one of the two animals. vMCK-2 caused a dramatic infiltration of cell. The 20 μg administration caused more infiltration than did the 60 μg and 8 μg administration. vMIP-1 caused a mild infiltration at all doses tested. In contrast to similar experiments where lower chemokine concentrations were used, mC10 caused little to no infiltration in this experiment. VKB8-1 caused no infiltration in this experiment.

TABLE 18

Mononuclear cell infiltration

| Polypeptide | Dose | 24 hours | | 48 hours | |
|---|---|---|---|---|---|
|  |  | monkey 1 | monkey 2 | monkey 3 | monkey 4 |
| vMIP-1 | 60 μg | 1 | — | 1 | — |
|  | 20 μg | — | 1 | — | 0 |
|  | 8 μg | 0 | — | 0 | — |
| C10 | 60 μg | 0 | — | 0 | — |
|  | 20 μg | — | 0 | — | 0 |
|  | 8 μg | — | 1 | — | 0 |
| vMCK-2 | 60 μg | 3 | — | 3 | — |
|  | 20 μg | — | 4 | — | 2 |
|  | 8 μg | — | 3 | — | 1 |
| SHAAYtide | 60 μg | 0 | — | 0 | — |
| (SEQ ID NO: 6) | 20 μg | — | 2* | — | 0 |
|  | 8 μg | 0 | — | 0 | — |
| CKβ8-1 | 60 μg | 0 | — | 0 | — |
| (residues 25-116) | 20 μg | — | 0 | — | 0 |
|  | 8 μg | — | — | — | — |
| Saline |  | 0 | 1 | 0 | 0 |

*indicates several clusters of cells rather than spread-out infiltrate

Example 15

Identification of Infiltrating Cells

To better define the identity of the infiltrating cells seen in Example 14 (Table 18), the same samples were analyzed by immunohistochemistry using antibodies specific for different cell types. These antibodies included: CD68 (expressed on macrophages, neutrophils and dendritic cells), MHC II (antigen-presenting cells, e.g. macrophages and dendritic cells), HAM-56 (macrophages), fascin (dendritic cells, endothelial cells and epithelial cells), elastase (neutrophils), cytokeratin (epithelial cells), CD3 (T cells), CD20 (B cells), and CD1a (Langerhans cells).

The vMCK-2-injected skin samples contained primarily neutrophils and antigen-presenting cells, including macrophages and dendritic cells. The mC10-injected skin samples contained primarily antigen-presenting cells, including macrophages and dendritic cells, but few neutrophils. The vMIP-1-injected skin samples contained primarily neutrophils and macrophages, with few dendritic cells. Few T cells, and no B cells, were found in the skin samples for each of the three chemokines.

Example 16

SHAAYtide (SEQ ID NO:6) Adjuvant Activity in Rhesus Monkeys

Since the SHAAYtide (SEQ ID NO:6) and the chemokines mC10 and vMCK-2 recruited APCs, including dendritic cells, to the site of injection, these polypeptides were tested for their ability to act as immunization adjuvants to augment the immune response to a co-injected foreign antigen. Five groups of monkeys, 3 monkeys per group, were injected intradermally with chicken ovalbumin (OVA) as an antigen. The first group of monkeys received OVA alone, while the second group contained OVA emulsified 1:1 with incomplete Freund's adjuvant (IFA), a standard adjuvant. The third group contained OVA, IFA, and vMCK-2, the fourth group contained OVA, IFA, mC10; and the fifth group contained OVA, IFA, and SEQ ID NO:6. The formulations (containing 2 mg OVA and 16 μg polypeptide) were injected intradermally in 100 μl. Ten ml of peripheral blood was drawn from each monkey twice a week for three weeks, and the blood samples were then subjected to centrifugation over Ficoll to remove erythrocytes and granulocytes. The plasma supernatant was analyzed by sandwich ELISA to determine the levels of anti-OVA antibodies using OVA-coated plastic dishes and a biotinylated anti-monkey IgG detection antibody. The results, reported in "antibody units" (see Example 12), are shown in Table 19. Reported numbers represent OVA-specific IgG levels, expressed in antibody units/ml, in the plasma of the 15 monkeys. Each horizontal line shows the response of an individual monkey over time after immunization.

TABLE 19

Induction of anti-OVA antibodies in monkeys

| Formulation | N | day 0 | day 5 | day 9 | day 12 | day 16 | day 19 |
|---|---|---|---|---|---|---|---|
| OVA | 1 | 428 | 393 | 445 | 814 | 941 | 1,116 |
|  | 2 | 4,577 | 4,073 | 4,228 | 4,475 | 8232 | 3,740 |
|  | 3 | 243 | 248 | 255 | 279 | 280 | 202 |
| OVA + IFA | 1 | 114 | 118 | 368 | 11,987 | 36,435 | 44,781 |
|  | 2 | 370 | 325 | 156 | 29,670 | 76,084 | 76,240 |
|  | 3 | 299 | 210 | 221 | 21,353 | 50,374 | 59,184 |
| OVA + IFA + vMCK2 | 1 | 249 | 242 | 261 | 4,205 | 6,097 | 10,827 |
|  | 2 | 294 | 263 | 360 | 26,985 | 44,230 | 53,383 |
|  | 3 | 310 | 262 | 263 | 40,264 | 109,919 | 135,608 |
| OVA + IFA + mC10 | 1 | 323 | 294 | 430 | 55,498 | 96,905 | 114,818 |
|  | 2 | 267 | 252 | 451 | 88,997 | 98075 | 97,376 |
|  | 3 | 390 | 356 | 465 | 50,940 | 81,888 | 109,445 |
| OVA + IFA + SHAAY (SEQ ID NO: 6) | 1 | 112 | 123 | 353 | 85,503 | 248,798 | 155,614 |
|  | 2 | 449 | 389 | 469 | 43,543 | 93,760 | 119,176 |
|  | 3 | 163 | 161 | 201 | 62,188 | 118,359 | 118,618 |

As shown in Table 19, monkeys injected with OVA and IFA developed a significant antibody response to OVA, as demonstrated by development of circulating anti-OVA IgG, commencing on day 12. In comparison, the levels of OVA-specific IgG in monkeys injected with OVA, mC10 and IFA, or OVA, shaag and IFA were substantially greater than those in monkeys not receiving mC10 or SEQ ID NO:6 respectively.

Example 17
SHAAYtide (SEQ ID NO:6) Adjuvant Activity in Mice

The experiment described in Example 16 was repeated, except the formulations were administered to BALB/c mice with 10 µg (Table 20) or 500 µg (Table 21) of OVA with in 100 µl. IFA was not used.

BALB/c mice were given OVA with or without SHAAYtide (SEQ ID NO:6) either intraperitoneally on days 0 and 21 (Table 20), or sub-cutaneously on days 0 and 14 (Table 21). Blood samples were collected at the indicated time points. The results, reported in antibody units, are given in Tables 20 and 21, showing IgG levels.

TABLE 20

Induction of anti-OVA antibodies in mice (10 µg OVA)

| Formulation | N | 0 day (d) | 10 d | 15 d | 27 d | 31 d | 36 d |
|---|---|---|---|---|---|---|---|
| OVA | 1 | 47 | 7 | 1,225 | 19,258 | 22,449 | 24,656 |
|  | 2 | 51 | 7 | 672 | 3,725 | 6,710 | 6,084 |
|  | 3 | 186 | 47 | 57 | 9,928 | 16,094 | 18,524 |
|  | 4 | 24 | 28 | 125 | 1,970 | 8,766 | 9,796 |
|  | 5 | 17 | 17 | 0 | 3,789 | 10,710 | 12,419 |
|  | average | 65 | 21 | 416 | 7,734 | 12,946 | 14,296 |
|  | increase from day 0 |  | 0 | 351 | 7,669 | 12,881 | 14,231 |
| OVA and 2 µg SHAAYtide (SEQ ID NO: 6) | 1 | 10 | 56 | 281 | 14,609 | 17,134 | 18,119 |
|  | 2 | 4 | 120 | 142 | 13,572 | 15,917 | 18,201 |
|  | 3 | 10 | 7 | 0 | 6,672 | 10,933 | 12,047 |
|  | 4 | 2 | 267 | 185 | 22,843 | 22,390 | 23,180 |
|  | 5 | 91 | 51 | 0 | 203 | 5,060 | 7,547 |
|  | average | 23 | 100 | 122 | 11,580 | 14,287 | 15,819 |
|  | increase from day 0 |  | 77 | 98 | 11,556 | 14,263 | 15,795 |
| OVA and 20 µg SHAAYtide (SEQ ID NO: 6) | 1 | 14 | 734 | 3,116 | 557,000 | 951,900 | 943,800 |
|  | 2 | 0 | 14 | 220 | 589,300 | 861,200 | 807,400 |
|  | 3 | 10 | 87 | 24 | 893 | 1,016 | 1,187 |
|  | 4 | 10 | 24 | 99 | 17,326 | 21,714 | 20,529 |
|  | 5 | 56 | 101 | 645 | 194,100 | 132,910 | 428,400 |
|  | average | 18 | 192 | 821 | 271,724 | 393,748 | 440,263 |
|  | increase from day 0 |  | 174 | 803 | 271,706 | 393,730 | 440,245 |

TABLE 20-continued

Induction of anti-OVA antibodies in mice (10 µg OVA)

| Formulation | N | 0 day (d) | 10 d | 15 d | 27 d | 31 d | 36 d |
|---|---|---|---|---|---|---|---|
| 2 µg SHAAYtide (SEQ ID NO: 6) | 1 | 7 | 0 | 0 | 47 | 47 | 60 |
| | 2 | 7 | 273 | 0 | 47 | 17 | 46 |
| | 3 | 14 | 0 | 0 | | 12 | 60 |
| | 4 | 24 | 0 | 0 | 58 | 0 | 0 |
| | average | 13 | 68 | 0 | 51 | 19 | 42 |
| | increase from day 0 | | 55 | 0 | 38 | 6 | 29 |
| 20 µg SHAAYtide (SEQ ID NO: 6) | 1 | 31 | 0 | 0 | 122 | 12 | 0 |
| | 2 | 47 | 0 | 0 | 110 | 32 | 0 |
| | 3 | 139 | 40 | 0 | 116 | 69 | 0 |
| | 4 | 64 | 592 | 168 | 98 | 47 | 0 |
| | average | 70 | 158 | 42 | 112 | 40 | 0 |
| | increase from day 0 | | 88 | 0 | 41 | 0 | 0 |

TABLE 21

Induction of anti-OVA antibodies in mice (500 µg OVA)

| Formulation | n | 0 days (d) | 7 d | 10 d | 14 d | 17 d | 21 d | 24 d | 28 d |
|---|---|---|---|---|---|---|---|---|---|
| OVA | 1 | 98 | 522 | 7,380 | 17,010 | 43,418 | 530,680 | 944,980 | 942,870 |
| | 2 | 56 | 954 | 10,149 | 36,041 | 65,810 | 1,115,660 | | 1,277,790 |
| | 3 | 62 | 393 | 2,553 | 25,490 | 79,466 | 723,950 | 1,158,540 | 1,223,230 |
| | 4 | 37 | 179 | 2,316 | 8,725 | 34,167 | 398,560 | 682,620 | 511,990 |
| | 5 | 37 | 311 | 4,964 | 23,491 | 41,107 | 545,370 | 779,110 | 972,210 |
| | average | 58 | 472 | 5,472 | 22,151 | 52,794 | 662,844 | 891,313 | 985,618 |
| | increase from day 0 | | 414 | 5,414 | 22,093 | 52,736 | 662,786 | 891,255 | 985,560 |
| OVA and SHAAYtide (SEQ ID NO: 6) | 1 | 46 | 5,443 | 14,590 | 75,541 | 152,634 | 1,722,880 | 1,943,050 | 1,845,900 |
| | 2 | 62 | 15,920 | 39,148 | 152,684 | 372,177 | 3,736,828 | 5,170,740 | 3,721,768 |
| | 3 | 46 | 12,385 | 18,278 | 87,000 | 144,402 | 1,237,090 | 2,198,920 | 1,959,610 |
| | 4 | 43 | 4,978 | 18,324 | 113,288 | 184,545 | 1,991,710 | 2,473,640 | 2,048,890 |
| | 5 | 37 | 8,276 | 18,164 | 147,302 | 430,918 | 3,309,069 | 4,420,730 | 3,572,379 |
| | average | 47 | 9,400 | 21,701 | 115,163 | 256,935 | 2,399,515 | 3,241,416 | 2,629,709 |
| | increase from day 0 | | 9,354 | 21,654 | 115,116 | 256,888 | 2,399,469 | 3,241,369 | 2,629,663 |

Example 18

SHAAYtide (SEQ ID NO:6) Shows Different Modulatory Effects on Different Types of Immune Responses Generated in Rhesus Monkeys Different types of immune responses can be induced in mammals by varying parameters such as the dose of antigen, the formulation, the route of administration, and the type of adjuvant. For example, when the adjuvant alum is used for vaccination purposes in humans or laboratory animals, the generated immune response is predominated by antibodies of the $IgG_1$ and IgGE classes, shows little generation of cytotoxic T cells, and shows augmentation of eosinophils and mast cells. In contrast, when stronger adjuvants, such as Complete or Incomplete Freund's adjuvants, are used, a broader spectrum of immune responses is observed, including the appearance of cytotoxic T cells and $IgG_2$ antibodies. To determine if SHAAYtide (SEQ ID NO:6) effects different types of immune responses in different ways, Rhesus monkeys were immunized in OVA formulated in either IFA adjuvant or alum adjuvant, with and without SHAAYtide (SEQ ID NO:6) (either unconjugated or directly conjugated to OVA). Results are shown in Table 22 and are repored as antibody units

TABLE 22

Effect of SHAAYtide (SEQ ID NO: 6) on OVA-specific antibody responses in monkeys, using either IFA adjuvant or alum adjuvant

| Formulation | N | 0 days (d) | 5 d | 8 d | 12 d | 15 d | 19 d |
|---|---|---|---|---|---|---|---|
| OVA | 1 | 6,491 | 7,738 | 5,956 | 6,501 | 19,661 | 31,138 |
| | 2 | 4,008 | 3,187 | 4,910 | 6,538 | 10,390 | 10,815 |
| | 3 | 28,442 | 19,924 | 21,147 | 46,872 | 80,612 | 135,978 |
| | Average | 12,980 | 10,283 | 10,671 | 19,971 | 36,888 | 59,310 |
| | increase from day 0 | | 0 | 0 | 6,990 | 23,907 | 46,330 |
| OVA and IFA | 1 | 7,153 | 6,013 | 6,649 | 1,115,400 | 4,757,400 | 1,339,900 |
| | 2 | 6,195 | 5,707 | 6,483 | 1,635,840 | 4,549,100 | 2,096,500 |
| | 3 | 6,810 | 6,379 | 5,671 | 31,200 | 110,290 | 464,200 |
| | Average | 6,719 | 6,033 | 6,268 | 927,480 | 3,138,930 | 1,300,200 |
| | increase from day 0 | | 0 | 0 | 920,761 | 3,132,211 | 1,293,481 |

TABLE 22-continued

Effect of SHAAYtide (SEQ ID NO: 6) on OVA-specific antibody responses in monkeys, using either IFA adjuvant or alum adjuvant

| | | | | | | | |
|---|---|---|---|---|---|---|---|
| OVA, IFA and SHAAYtide (SEQ ID NO: 6) | 1 | 10,911 | 10,845 | 19,733 | 2,626,680 | 8,155,800 | 2,453,900 |
| | 2 | 5,761 | 5,761 | 5,636 | 226,440 | 1,129,700 | 1,641,100 |
| | 3 | 5,113 | 4,541 | 4,072 | 102,050 | 979,800 | 772,500 |
| | Average | 7,262 | 7,049 | 9,814 | 985,057 | 3,421,767 | 1,622,500 |
| | increase from day 0 | | 0 | 2,552 | 977,795 | 3,414,505 | 1,615,238 |
| OVA and alum | 1 | 12,972 | 11,972 | 42,808 | 3,111,610 | 10,305,900 | 2,733,400 |
| | 2 | 10,317 | 7,699 | 6,100 | 38,710 | 90,470 | 106,020 |
| | 3 | 4,623 | 4,426 | 5,252 | 870,190 | 1,516,100 | 931,300 |
| | Average | 9,304 | 8,032 | 18,053 | 1,340,170 | 3,970,823 | 1,256,907 |
| | increase from day 0 | | 0 | 8,749 | 1,330,866 | 3,961,519 | 1,247,603 |
| OVA + alum and SHAAYtide (SEQ ID NO: 6) | 1 | 8,563 | 6,603 | 6,227 | 29,760 | 44,610 | 65,680 |
| | 2 | 3,231 | 3,290 | 3,284 | 31,930 | 159,320 | 172,250 |
| | 3 | 7,327 | 6,031 | 6,649 | 22,220 | 52,970 | 66,580 |
| | Average | 6,374 | 5,308 | 5,387 | 27,970 | 85,633 | 101,503 |
| | increase from day 0 | | 0 | 0 | 21,596 | 79,260 | 95,130 |
| OVA-PDx-S + alum | 1 | 14,314 | 12,179 | 10,380 | 57,740 | 91,480 | 103,660 |
| | 2 | 5,941 | 4,959 | 4,526 | 17,180 | 13,790 | 15,830 |
| | 3 | 4,024 | 3,820 | 4,428 | 16,580 | 22,400 | 28,990 |
| | Average | 8,093 | 6,986 | 6,445 | 30,500 | 42,557 | 49,493 |
| | increase from day 0 | | 0 | 0 | 22,407 | 34,464 | 41,400 |

| Formulation | N | 22 d | 26 d | 30 d | 34 d | 37 d |
|---|---|---|---|---|---|---|
| OVA | 1 | 46,462 | 120,111 | 271,183 | 224,626 | 244,479 |
| | 2 | 10,961 | 12,511 | 10,248 | 12,212 | 11,806 |
| | 3 | 184,220 | 495,330 | 1,008,627 | 871,569 | 977,820 |
| | Average | 80,548 | 209,317 | 430,019 | 369,469 | 411,368 |
| | increase from day 0 | 67,567 | 196,337 | 417,039 | 356,489 | 398,388 |
| OVA and IFA | 1 | 1,239,800 | 1,616,100 | 6,688,100 | 5,192,800 | 3,997,800 |
| | 2 | 2,595,900 | 3,629,900 | 14,280,600 | 12,801,700 | 9,471,900 |
| | 3 | 776,800 | 719,100 | 1,705,300 | 1,730,100 | 1,640,600 |
| | Average | 1,537,500 | 1,988,367 | 7,558,000 | 6,574,867 | 5,036,767 |
| | increase from day 0 | 1,530,781 | 1,981,647 | 7,551,281 | 6,568,147 | 5,030,047 |
| OVA, IFA and SHAAYtide (SEQ ID NO: 6) | 1 | 2,167,900 | 1,752,400 | 6,539,100 | 5,953,300 | 3,884,600 |
| | 2 | 3,504,600 | 4,800,100 | 14,210,200 | 13,281,600 | 11,330,700 |
| | 3 | 1,096,100 | 2,289,700 | 7,837,300 | 9,869,200 | 6,649,100 |
| | Average | 2,256,200 | 2,947,400 | 9,528,867 | 9,701,367 | 7,288,133 |
| | increase from day 0 | 2,248,938 | 2,940,138 | 9,521,605 | 9,694,105 | 7,280,872 |
| OVA and alum | 1 | 2,624,300 | 2,194,800 | 9,286,200 | 6,262,500 | 7,581,600 |
| | 2 | 106,820 | 214,570 | 1,346,300 | 1,078,300 | 767,100 |
| | 3 | 826,000 | 2,469,200 | 14,421,700 | 12,237,300 | 7,778,500 |
| | Average | 1,185,707 | 1,626,190 | 8,351,400 | 6,526,033 | 5,375,733 |
| | increase from day 0 | 1,176,403 | 1,616,886 | 8,342,096 | 6,516,729 | 5,366,429 |
| OVA + alum and SHAAYtide (SEQ ID NO: 6) | 1 | 78,660 | 130,850 | 819,100 | 789,500 | 555,900 |
| | 2 | 163,670 | 406,770 | 1,607,100 | 1,780,100 | 1,619,300 |
| | 3 | 69,310 | 61,240 | 1,110,800 | 982,500 | 750,500 |
| | Average | 103,880 | 199,620 | 1,179,000 | 1,184,033 | 975,233 |
| | increase from day 0 | 97,506 | 193,246 | 1,172,626 | 1,177,660 | 968,860 |
| OVA-PDx-S + alum | 1 | 75,810 | 99,510 | 711,090 | 582,600 | 547,100 |
| | 2 | 15,270 | 26,290 | 91,380 | 89,380 | 96,440 |
| | 3 | 31,070 | 129,720 | 1,056,800 | 1,266,300 | 1,035,400 |
| | Average | 40,717 | 85,173 | 619,757 | 646,093 | 559,647 |
| | increase from day 0 | 32,624 | 77,080 | 611,664 | 638,000 | 551,554 |

While the co-administration of SHAAYtide (SEQ ID NO:6) did not diminish the OVA with IFA response, it dramatically reduced the IgG response induced by OVA plus alum. These data indicate SHAAYtide (SEQ ID NO:6) is capable of down-regulating immune responses to antigen administered in alum adjuvant, but not to the same antigen administered in IFA adjuvant. Thus, SHAAYtide (SEQ ID NO:6) can be used as an immune modulator.

Example 19

(Prophetic) Procedure to Determine the Chemotactic Properites of a Candidate Molecule To perform chemotaxis assays, 29 µl of a candidate or known chemotaxins for a specific cell type, such as for dendritic cells (immature or mature), at 0, 1, 10 and 100 nM are placed in the wells of the lower chamber of a 96-well chemotaxis chambers (Neuroprobe; Gaithersburg, Md.). Day 7 immature dendritic cells are harvested, washed once with chemotaxis buffer (0.1% BSA in Hank's balanced salt solution (HBSS; Invitrogen, Carlsbad, Calif.), with $Ca^{++}$ and $Mg^{++}$), and resuspended in chemotaxis buffer at $5 \times 10^6$ cells/ml. Twenty microliters of cells is placed onto the filter. The chambers are incubated for 90 minutes at 37° C. Migration is terminated by removing non-migrating cells on the top of the filter using a rubber scraper. After removing the filter and rinsing with Dulbecco's phosphate buffered saline (DPBS; Hyclone, Darra, Queensland, Australia), cells that have migrated are quantified by cell staining, such as the Hema3 staining kit (Fisher Scientific; Tustin, Calif.) or the CyQuant assay (Molecular Probes; Eugene, Oreg.), a fluorescent dye method that measures nucleic acid content and microscopic observation. The lower chamber is inspected microscopically to determine if any cells have migrated into the wells. If significant number of cells is present in the wells, quantification is done in the wells as well as the filter. The magnitude of migration is calculated as the ratio of absorbance between the wells with chemoattractants and the wells with chemotaxis buffer alone.

Example 20

(Prophetic) Procedure to Evaluate APC Chemotaxins in Augmenting or Modulating Systemic and/or Mucosal Immune Responses to Infectious Diseases Groups of mice are injected either subcutaneously, intradermally, intranasally, or by any other mode with varying doses of the virus, bacterium, or parasite under study, using a typical immunization schedule, e.g., days 0, 7, and 14, in the presence or absence of APC chemotaxin given simultaneously with the microorganism in an appropriate formulation which may include adjuvants. Serum and/or mucosal secretions are collected on days −7, 0, 7, 14, 21, 28 and 35 for antigen-specific antibody analysis by ELISA. Mice are sacrificed at different time intervals (such as after the last immunization to quantitate the antigen-specific antibody-forming cells and antigen-specific T cell responses (both cytotoxic and helper T cell populations)) present in immune compartments, using standard procedures.

Example 21

(Prophetic) Procedure to Evaluate APC Chemotaxins in Augmenting or Modulating Anti-Tumor Immunity in Cancer Immunotherapy Regimens While many tumor cells express unique tumor-associated antigens, these antigens are invariably weak immunogens and fail to generate potent anti-tumor immunity during tumor progression. The ability of APC chemotaxins, such as SHAAYtide (SEQ ID NO:6), to augment protective anti-tumor immunity can be evaluated using a model system of cancer immunotherapy in mice. In this model, mice are transplanted with a syngeneic thymoma (EL4 cells; American Type Tissue Collection (ATTC); Manassas, Va.; no. TIB-39) that have previously been transfected with the experimental protein antigen OVA (ATTC; no. CRL-2113 (chicken OVA EL4 transfectants). Without further intervention, the tumor grows and eventually kills the mouse. Animals can be at least partially protected by vaccinating them with OVA formulated in adjuvant to induce an antigen-specific immune response directed against the OVA-transfected thymoma cells. This model is effective to evaluate the relative efficacy of adjuvants in augmenting or modulating protective anti-tumor immunity. Positive controls in this model include the following adjuvants: CFA, IFA, alum and GM-CSF. The ability of APC chemotaxins to augment cancer immunotherapy regimens can be evaluated by comparison to these known adjuvants.

Example 22

(Prophetic) Procedure to Evaluate Ability of APC Chemotaxins to Modulate Allergen-Specific Immune Responses to Decrease Allergen-Induced Pathology An animal model of asthma can be induced by sensitizing rodents to an experimental antigen (e.g., OVA) by standard immunization, and then subsequently introducing that same antigen into the rodent's lung by aerosolization. Three series of rodent groups, comprising 10 rodents per goup, are actively sensitized on Day 0 by a single intraperitoneal injection with 100 μg OVA in phosphate-buffered saline (PBS), along with an IgE-selective adjuvant, such as aluminum hydroxide ("alum" adjuvant). At 11 days after sensitization at the peak of the IgE response, the animals are placed in a Plexiglas chamber and challenged with aerosolized OVA (1%) for 30 minutes using an ultrasonic nebulizer (DeVilbiss Co.; Somerset, Pa.). One series of mice additionally receives phosphate buffered saline (PBS) and Tween 0.5% intraperitoneally at the initial sensitization, and at different dosing schedules thereafter, up until the aerosolized OVA challenge. A second series consists of groups of mice receiving different doses of APC chemotaxins given either intraperitoneally, intravenously, sub-cutaneously, intramuscularly, orally, or via any other mode of administration, at the initial sensitization, and at different dosing schedules thereafter, up until the aerosolized OVA challenge. A third series of mice, serving as a positive control, consists of groups treated with either mouse IL-10 intraperitoneally, anti-IL4 antibodies intraperitoneally, or anti-IL5 antibodies intraperitoneally at the initial sensitization, and at different dosing schedules thereafter, up until the aerosolized OVA challenge.

Animals are subsequently analyzed at different time points after the aerosolized OVA challenge for pulmonary function, cellular infiltrates in bronchoalveolar lavage (BAL), histological examination of lungs, and measurement of serum OVA-specific IgE titers.

Alternative Embodiments

The persent invention is a method for enhancing an immune response to an antigen in a subject. The method comprises the steps of administering at least one polypeptide consisting of from about 10 to about 90 amino acids that includes an amino acid sequence having at least about 90% sequence identity to a sequence selected from the group consisting of SEQ ID NOS: 1, 3, 5, 6, 8, and 11; and at least one antigen. The polypeptide enhances the immune response to the antigen. In this method, the immune response is an antibody-mediated immune response. The administering increases the titer of antigen-specific antibodies in the subject by at least two-fold. In this method, the polypeptide and antigen are combined in a composition prior to the administering or are administered separately. At least two different polypeptides may be administered. In this method, the polypeptide comprises the antigen. In this method, the amino acid sequence has at least about 94% sequence identity to the sequence. In this method, the amino acid sequence is selected from the group consisting of SEQ ID NOS: 1, 3, 5, 6, 8, and 11. In this method, the amino acid sequence is SEQ ID NO:6. In this method, the polypeptide is SEQ ID NO:6. The polypeptide is combined with a material for sustained release thereof in the subject. The antigen is from a pathogen. The antigen is a tumor antigen. The method further comprises administering an adjuvant. The method further comprises administering a multivalent carrier. The multivalent carrier is linked to the polypeptide, the antigen or an adjuvant. The step of administering the at least one polypeptide comprises contacting a solid tumor with the polypeptide or the antigen. The step of administerin the at least one polypeptide comprises contacting tissue surrounding a solid tumor with the polypeptide or the antigen. The administering is repeated at least twice. The at least one polypeptide and the antigen are administered at different sites. The polypeptide is administered as a polynucleotide encoding the polypeptide. The antigen is administered as a polynucleotide encoding the antigen. The antigen is an allergen. In this method, the polypeptide consists of from about 10 to about 60 amino acids. In this method, the polypeptide consists of from about 10 to about 30 amino acids. In this method, the amino acid sequence consists of from about 10 to about 70 amino acids. In this method, the amino acid sequence consists of from about 10 to about 60 amino acids. In this method, the amino acid sequence consists of from about 10 to about 50 amino acids. In this method, the amino acid sequence consists of from about 10 to about 40 amino acids. In this method, the amino acid sequence consists of from about 10 to about 30 amino acids.

The present invention is a composition for enhancing an immune response to one or more antigens. The composition comprises at least one polypeptide consisting of from about 10 to about 90 amino acids that includes an amino acid sequence having at least about 90% sequence identity to a sequence selected from the group consisting of SEQ ID NOS: 1, 3, 5, 6, 8, and 11; and at least one antigen. The polypeptide enhances the immune response to the antigen and the polypeptide and the antigen are different. The composition comprises at least two different polypeptides. In the composition, the amino acid sequence is selected from the group consisting of SEQ ID NOS:1, 3, 5, 6, 8, and 11. The composition is formulated for sustained release. The composition further comprises an adjuvant. In the composition, the polypeptide consists of from about 10 to about 80 amino acids. In the composition, the amino acid sequence consists of from about 10 to about 70 amino acids. In the composition, the amino acid sequence consists of from about 10 to about 60 amino acids. In the composition, the amino acid sequence consists of from about 10 to about 50 amino acids. In the composition, the amino acid sequence consists of from about 10 to about 40 amino acids. In the composition, the amino acid sequence consists of from about 10 to about 30 amino acids.

The present invention is a composition for enhancing an immune response to one or more antigens. The composition comprises at least one isolated polypeptide consisting of from about 10 to about 90 amino acids that includes an amino acid sequence having at least about 90% sequence identity to a sequence selected from the group consisting of SEQ ID NOS: 1, 5, 6, 8, and 11; and at least one antigen. The polypeptide enhances the immune response to the antigen. In the composition, the polypeptide consists of from about 10 to about 80 amino acids. In the composition, the amino acid sequence consists of from about 10 to about 60 amino acids. In the composition, the amino acid sequence consists of from about 10 to about 50 amino acids. In the composition, the amino acid sequence consists of from about 10 to about 40 amino acids. In the composition, the amino acid sequence consists of from about 10 to about 30 amino acids.

The invention is a method for enhancing an immune response to an antigen in a subject. The method comprises administering an immune response enhancing fragment of a polypeptide set forth in SEQ ID NO: 16 consisting of from about 10 to about 90 amino acids, wherein said fragment comprises an amino acid sequence at least about 90% sequence identity to a sequence selected from the group consisting of SEQ ID NOS: 1, 3, 5, 6, 8, and 11; and an antigen.

The present invention is a composition comprising a cell exogenously expressing at least one sequence having at least 90% sequence identity to a nucleic acid sequence selected from the group consisting of SEQ ID NOS: 20, 22, 24, 25, 27, and 30, or fragment thereof. In the composition, the cell is allogeneic. In the composition, the cell is autologous. The composition further comprises a tumor-associated antigen. In the composition, the cell is a cancer cell. In the composition, the cancer cell is from a cancer cell line. In the composition, the cancer cell line is a human ovarian cancer cell line or a human brain cancer cell line. The composition further comprises a tumor-associated antigen. In the composition, the tumor-associated antigen is from an autologous cell.

The present invention is a composition, comprising at least one tumor cell; and at least one cell exogenously expressing at least one sequence having at least 80% sequence identity to a nucleic acid sequence selected from the group consisting of SEQ ID NOS: 20, 22, 24, 25, 27, and 30, or fragment thereof. In the composition, the tumor cell is a primary tumor cell. In the composition, the tumor cell is autologous. In the composition, the tumor cell is a glioma, glioblastoma, gliosarcoma, astrocytoma, melanoma, breast cancer cell, or an ovarian cancer cell. In the composition, the tumor cell is a cancer cell. In the composition, the cell exogenously expressing the polynucleotide is quiescent.

The present invention is a kit comprising a pharmaceutical composition comprising at lease one polypeptide having at least 80% sequence identity to an amino acid sequence selected from the group consisting of SEQ ID NOS: 1, 3, 5, 6, 8, and 11, or a fragment thereof, and a pharmaceutically acceptable carrier; and a syringe.

The present invention is a kit comprising a pharmaceutical composition comprising at lease one polynucleotide having at least 80% sequence identity to a nucleic acid sequence selected from the group consisting of SEQ ID NOS: 20, 22, 24, 25, 27, and 30, or a fragment thereof, and a pharmaceutically acceptable carrier; and a syringe.

It is therefore intended that the foregoing detailed description be regarded as illustrative rather than limiting, and that it be understood that it is the following claims, including all equivalents, that are intended to define the spirit and scope of this invention.

References

U.S. Pat. No. 4,522,811. Serial injection of muramyldipeptides and liposomes enhances the anti-infective activity of muramyldipeptides.

U.S. Pat. No. 5,223,409. Directed evolution of novel binding proteins. 1993.

U.S. Pat. No. 5,328,470. Treatment of diseases by site-specific instillation of cells or site-specific transformation of cells and kits therefor. 1994.

U.S. Pat. No. 5,994,126. Method for in vitro proliferation of dendritic cell precursors and their use to produce immunogens. 1999.

Ausubel, F. M., R. Brent, R. E. Kingston, D. D. Moore, et al. 1987. Current protocols in molecular biology. John Wiley & Sons, New York.

Baek S H, Seo J K, Chae C B, Suh P G, Ryu S H. 1996. Identification of the peptides that stimulate the phosphoinositide hydrolysis in lymphocyte cell lines from peptide libraries. *J Biol Chem* 271(14):81 70-5.

Baggiolini, M., and C. A. Dahinden. 1994. CC chemmokines in allergic inflammation. *Immunol Today* 15:127.

Baggiolini, M., B. Dewald, and B. Moser. 1997. Human chemokines: an update. *Annu Rev Immunol* 15:675.

Bender et al., 1996, *J. Immunol. Methods* 196:121-35

Berkhout, T. A., J. Gohil, P. Gonzalez, C. L. Nicols, K. E. Moores, C. H. Macphee, J. R. White, and P. H. Groot. 2000. Selective binding of the truncated form of the chemokine CKbeta8 (25-99) to CC chemokine receptor 1(CCR1). *Biochem Pharmacol* 59:591.

Bonecchi, R., N. Polentarutti, W. Luini, A. Borsatti, S. Bernasconi, M. Locati, C. Power, A. Proudfoot, T. N. Wells, C. Mackay, A. Mantovani, and S. Sozzani. 1999. Up-regulation of CCR1 and CCR3 and induction of chemotaxis to CC chemokines by IFN-gamma in human neutrophils. *J Immunol* 162:474.

Bao L, Gerard N P, Eddy R L Jr, Shows T B, Gerard C. 1992. Mapping of genes for the human C5a receptor (C5AR), human FMLP receptor (FPR), and two FMLP receptor homologue orphan receptors (FPRH1, FPRH2) to chromosome 19. *Genomics* 13(2):437-40.

Campbell et al., 1998, *J Cell Biol* 141:1053-9

Carell, T., E. A. Wintner, and J. Rebek Jr. 1994a. A novel procedure for the synthesis of libraries containing small organic molecules. *Angewandte Chemie International Edition*. 33:2059-2061.

Carell, T., E. A. Wintner, and J. Rebek Jr. 1994b. A solution phase screening procedure for the isolation of active compounds from a molecular library. *Angewandte Chemie International Edition*. 33:2061-2064.

Carter, P. 1986. Site-directed mutagenesis. *Biochem J.* 237:1-7.

Celia et al., 1999, *J Exp Med.* 189:821-9.

Chan et al., 1999, *Blood* 93:3610-6.

Chen, S. H., H. D. Shine, J. C. Goodman, R. G. Grossman, et al. 1994. Gene therapy for brain tumors: regression of experimental gliomas by adenovirus-mediated gene transfer in vivo. *Proc Natl Acad Sci USA*. 91:3054-7.

Cho, C. Y., E. J. Moran, S. R. Cherry, J. C. Stephans, et al. 1993. An unnatural biopolymer. *Science*. 261:1303-5.

Christophe, T., Karlsson, A., Dugave, C, Marie-Josephe Rabiet, Francois Boulay, F., and Dahlgren, C. (2001). The Synthetic Peptide Trp-Lys-Tyr-Met-Val-Met-NH$_2$ Specifically Activates Neutrophils through FPRL1/Lipoxin A$_4$ Receptors and Is an Agonist for the Orphan Monocyte-expressed Chemoattractant Receptor FPRL2. *J. Biol. Chem., Vol.* 276, Issue 24, 21585-21593.

Cohen. 1993. *Science* 259:1691-1692.

Coligan, 1991. *Current Protocols in Immunology*, Wiley/Greene, NY.

Cull, M. G., J. F. Miller, and P. J. Schatz. 1992. Screening for receptor ligands using large libraries of peptides linked to the C terminus of the lac repressor. *Proc Natl Acad Sci USA*. 89:1865-9.

Cwirla, S. E., E. A. Peters, R. W. Barrett, and W. J. Dower. 1990. Peptides on phage: a vast library of peptides for identifying ligands. *Proc Natl Acad Sci USA*. 87:6378-82.

Deng, X., Ueda, H., Su, S. B., Gong, W., Dunlop, N. M., Gao, J.-L., Murphy, P. M., and Wang, J. M. (1999) A Synthetic Peptide Derived From Human Immunodeficiency Virus Type 1 gp120 Downregulates the Expression and Function of Chemokine Receptors CCR5 and CXCR4 in Monocytes by Activating the 7-Transmembrane G-Protein-Coupled Receptor FPRL1/LXA4R. *Blood* 94, 1165-1173.

Devlin, J. J., L. C. Panganiban, and P. E. Devlin. 1990. Random peptide libraries: a source of specific protein binding molecules. *Science*. 249:404-6.

DeWitt, S. H., J. S. Kiely, C. J. Stankovic, M. C. Schroeder, et al. 1993. "Diversomers": an approach to nonpeptide, nonoligomeric chemical diversity. *Proc Natl Acad Sci USA*. 90:6909-13.

Dieu et al., 1998, *J Exp Med* 188:373-86.

Fantuzzi, L., P. Borghi, V. Ciolli, G. Pavlakis, F. Belardelli, and S. Gessani. 1999. Loss of CCR2 expression and functional response to monocyte chemotactic protein (MCP-1) during the differentiation of human monocytes: role of secreted MCP-1 in the regulation of the chemotactic response. *Blood* 94:875

Felici, F., L. Castagnoli, A. Musacchio, R. Jappelli, et al. 1991. Selection of antibody ligands from a large library of oligopeptides expressed on a multivalent exposition yector. *J Mol Biol*. 222:301-10.

Fodor, S. P., R. P. Rava, X. C. Huang, A. C. Pease, et al. 1993. Multiplexed biochemical assays with biological chips. *Nature*. 364:555-6.

Forssmann, U., M. B. Delgado, M. Uguccioni, P. Loetscher, G. Garotta, and M. Baggiolini. 1997. CKbeta8, a novel CC chemokine that predominantly acts on monocytes. In *FEBS Lett, Vol.* 408, p. 211-6.

Gallop, M. A., R. W. Barrett, W. J. Dower, S. P. Fodor, et al. 1994. Applications of combinatorial technologies to drug discovery. 1. Background and peptide combinatorial libraries. *J Med Chem*. 37:1233-51.

Gennaro, A. R. 2000. Remington: The science and practice of pharmacy. Lippincott, Williams & Wilkins, Philadelphia, Pa.

Harlow, E., and D. Lane. 1988. Antibodies: A laboratory manual. Cold Spring Harbor Laboratory Press, Cold Spring Harbor. 726 pp.

Harlow, E., and D. Lane. 1999. Using antibodies: A laboratory manual. Cold Spring Harbor Laboratory PRess, Cold Spring Harbor, N.Y.

Houghten, R. A., J. R. Appel, S. E. Blondelle, J. H. Cuervo, et al. 1992. The use of synthetic peptide combinatorial libraries for the identification of bioactive peptides. *Biotechniques*. 13:412-21.

Kaufman, R. J. 1990. Vectors used for expression in mammalian cells. *Methods Enzymol*. 185:487-511.

Kellermann et al., 1999, *J Immunol* 162:3859-64.

Kriegler, M. 1990. Gene transfer and expression: A laboratory manual. Stockton Press, New York. 242 pp Lam, K. S. 1997. Application of combinatorial library methods in cancer research and drug discovery. *Anticancer Drug Design*. 12:145-167.

Lam, K. S., S. E. Salmon, E. M. Hersh, V. J. Hruby, et al. 1991. General method for rapid synthesis of multicomponent peptide mixtures. *Nature*. 354:82-84.

Le, Y., Oppenheim J. J., and Wang, J. M. 2001. Survey: Pleiotropic roles of formyl peptide receptors, *Cytokine and Growth Factor Reviews* 12: 91-105.

Lee, S. C., M. E. Brummet, S. Shahabuddin, T. G. Woodworth, S. N. Georas, K. M. Leiferman, S. C. Gilman, C. Stellato, R. P. Gladue, R. P. Schleimer, and L. A. Beck. 2000. Cutaneous injection of human subjects with macrophage inflammatory protein-1 alpha induces significant recruitment of neutrophils and monocytes. *J Immunol* 164: 3392

Luna, L. G. 1968. *The Manual of Histologic Staining Methods of the Armed Forces Institute of Pathology*", McGraw-Hill, 3rd edition.

Macphee, C. H., E. R. Appelbaum, K. Johanson, K. E. Moores, C. S. Imburgia, J. Fornwald, T. Berkhout, M. Brawner, P. H. Groot, K. O'Donnell, D. O'Shannessy, G. Scott, and J. R. White. 1998. Identification of a truncated form of the CC chemokine CK beta-8 demonstrating greatly enhanced biological activity. *J Immunol* 161:6273.

Mantovani, A. 1999. The chemokine system: redundancy for robust outputs. *Immunol Today* 20:254.

Murphy, P. M., Ozcelik, T., Kenney, R. T., Tiffany, H. L., McDermott, D., and Francke, U. 1992. A structural homologue of the N-formyl peptide receptor. Characterization and chromosome mapping of a peptide chemoattractant receptor family *J. Biol. Chem.* 267, 7637-7643

Murphy, P. M., M. Baggiolini, I. F. Charo, C. A. Hebert, R. Horuk, K. Matsushima, L. H. Miller, J. J. Oppenheim, and C. A. Power. 2000. International union of pharmacology. XXII. Nomenclature for chemokine receptors. *Pharmacol Rev* 52:145.

Patel, V. P., B. L. Kreider, Y. Li, H. Li, K. Leung, T. Salcedo, B. Nardelli, V. Pippalla, S. Gentz, R. Thotakura, D. Parmelee, R. Gentz, and G. Garotta. 1997. Molecular and functional characterization of two novel human C-C chemokines as inhibitors of two distinct classes of myeloid progenitors. *J Exp Med* 185:1163.

Romani et al., 1996, *J. Immunol. Methods* 196:137-51.

Rollins, B. J. 1997. Chemokines. *Blood* 90:909.

Sambrook, J. 1989. Molecular cloning: a laboratory manual. Cold Spring Harbor Laboratory, Cold Spring Harbor.

Scott, J. K., and G. P. Smith. 1990. Searching for peptide ligands with an epitope library. *Science*. 249:386-90.

Shao Bo Su, Ji-liang Gao, Wang-hua Gong, Nancy M. Dunlop, Philip M. Murphy, Joost J. Oppenheim and Ji Ming Wang. 1999. T21/DP107, A Synthetic Leucine Zipper-Like Domain of the HIV-1 Envelope gp41, Attracts and Activates Human Phagocytes by Using G-Protein-Coupled Formyl Peptide Receptors. *Journal of Immunology*, 162: 5924-5930.

Su, S. B., Gao, J.-L., Gong, W., Dunlop, N. M., Murphy, P. M., Oppenheim, J. J., and Wang, J. M. 1999. T21/DP107, A Synthetic Leucine Zipper-Like Domain of the HIV-1 Envelope gp41, Attracts and Activates Human Phagocytes by Using G-Protein-Coupled Formyl Peptide Receptors. *J. Immunol.* 162, 5924-5930.

Uguccioni, M., M. D'Apuzzo, M. Loetscher, B. Dewald, and M. Baggiolini. 1995. Actions of the chemotactic cytokines MCP-1, MCP-2, MCP-3, RANTES, MIP-1 alpha and MIP-1 beta on human monocytes. *Eur J Immunol* 25:64.

Ulmer et al., (1993) *Science* 259:1745-1749

Verdijk et al., 1999, *J Immunol.* 1:57-61

Weber, C., K. U. Belge, P. von Hundelshausen, G. Draude, B. Steppich, M. Mack, M. Frankenberger, K. S. Weber, and H. W. Ziegler-Heitbrock. 2000. Differential chemokine receptor expression and function in human monocyte subpopulations. *J Leukoc Biol* 67:699.

Wells, J. A., M. Vasser, and D. B. Powers. 1985. Cassette mutagenesis: an efficient method for generation of multiple mutations at defined sites. *Gene*. 34:315-23.

Ye, R. D., Cavanagh, S. L., Quehenberger, O., Prossnitz, E. R., and Cochrane, C. G. 1992. Isolation of a cDNA that encodes a novel granulocyte N-formyl peptide receptor. *Biochem. Biophys. Res. Commun.* 184, 582-589.

Youn, B. S., S. M. Zhang, H. E. Broxmeyer, S. Cooper, K. Antol, M. Fraser, Jr., and B. S. Kwon. 1998. Characterization of CKbeta8 and CKbeta8-1: two alternatively spliced forms of human beta-chemokine, chemoattractants for neutrophils, monocytes, and lymphocytes, and potent agonists at CC chemokine receptor 1. *Blood* 91:3118.

Zoller, M. J., and M. Smith. 1987. Oligonucleotide-directed mutagenesis: a simple method using two oligonucleotide primers and a single-stranded DNA template. *Methods Enzymol.* 154:329-50.

Zuckermann, R. N., E. J. Martin, D. C. Spellmeyer, G. B. Stauber, et al. 1994. Discovery of nanomolar ligands for 7-transmembrane G-protein-coupled receptors from a diverse N-(substituted)glycine peptoid library. *J Med Chem.* 37:2678-85.

Bacon, K. B., R. D. Camp, F. M. Cunningham, and P. M. Woollard. 1988. Contrasting in vitro lymphocyte chemotactic activity of the hydroxyl enantiomers of 12-hydroxy-5,8,10,14-eicosatetraenoic acid. *Br J Pharmacol.* 95:966-74.

Bender, A., M. Sapp, G. Schuler, R. M. Steinman, et al. 1996. Improved methods for the generation of dendritic cells from nonproliferating progenitors in human blood. *J Immunol Methods*. 196:121-35.

Goodwin, J., R H. U.S. Pat. No. 5,284,753. 1994. Multiple-site chemotactic test apparatus and method.

Kraal, G., M. Breel, M. Janse, and G. Bruin. 1986. Langerhans' cells, veiled cells, and interdigitating cells in the mouse recognized by a monoclonal antibody. *J Exp Med.* 163:981-97.

Meikle, J. 2002. Pioneering gene treatment gives frail toddler a new lease of life. In The Guardian, London.

Nabel, E. G., and G. J. Nabel. U.S. Pat. No. 5,328,470. 1994. Treatment of diseases by site-specific instillation of cells or site-specific transformation of cells and kits therefor.

Penfold, M. E., D. J. Dairaghi, G. M. Duke, N. Saederup, et al. 1999. Cytomegalovirus encodes a potent alpha chemokine. *Proc Natl Acad Sci USA.* 96:9839-44.

Rossi, D., and A. Zlotnik. 2000. The Biology of Chemokines and their Receptors. *Annu. Rev. Immunol.* 18:217-242.

Shilo, B. Z., and R. A. Weinberg. 1981. DNA sequences homologous to vertebrate oncogenes are conserved in *Drosophila melanogaster. Proc Natl Acad Sci USA.* 78:6789-92.

Tice, T., R. Gilley, J. Eldridge, and J. Staas. U.S. Pat. No. 5,942,252. 1999. Method for delivering bioactive agents into and through the mucosally-associated lymphoid tissues and controlling their release.

The invention claimed is:

1. A composition for enhancing an immune response to one or more antigens, comprising an isolated polypeptide consisting of an amino acid sequence having at least about 90% sequence identity to a sequence selected from the group consisting of SEQ ID NOS: 1, 3, 5, 6, 8, and 11; and at least one antigen, wherein the polypeptide enhances the immune response to the antigen and provided that the polypeptide and the antigen are different.

2. The composition of claim 1, wherein the polypeptide consists of an amino acid sequence selected from the group consisting of SEQ ID NOS: 1, 3, 5, 6, 8, and 11.

3. The composition of claim 1, wherein the composition is formulated for sustained release.

4. The composition of claim 1, wherein the composition further comprises an adjuvant.

5. The composition of claim 1, wherein the pathogen is bacteria or virus.

6. The composition of claim 5, wherein the pathogen is selected from the group consisting of Bordetella pertussis, Neisseria meningitidis, Borrelia burgdorferi, Haemophilus influenza B, Streptococcs pneumonia, Salmonella typhi, Influenza virus; Hepatitis A; Hepatitis B; Hepatitis C; Measles; Rubella virus; Mumps; Rabies; Poliovirus; Japanese Encephalitis virus; Rotavirus; Varicella, Corynebacterium diphtheria and Clostridium tetani.

7. The composition of claim 1, wherein the pathogen is a tumor.

8. The composition of claim 1, wherein the antigen is covalently associated with the polypeptide.

9. The composition of claim 1, wherein the antigen is non-covalently associated with the polypeptide.

10. A composition for enhancing an immune response to one or more antigens, comprising an isolated polypeptide consisting of an amino acid sequence having at least about 90% sequence identity to a sequence selected from the group consisting of SEQ ID NOS: 1, 5, 6, 8, and 11; and at least one antigen, wherein the polypeptide enhances the immune response to the antigen, and wherein the polypeptide is physically linked to the antigen.

11. The composition of claim 10, wherein the polypeptide consists of an amino acid sequence selected from the group consisting of SEQ ID NOs: 1, 3, 5, 6, 8 and 11.

* * * * *